US010793641B2

(12) United States Patent
Wang et al.

(10) Patent No.: US 10,793,641 B2
(45) Date of Patent: Oct. 6, 2020

(54) FULLY HUMAN ANTI-MESOTHELIN ANTIBODIES AND IMMUNE EFFECTOR CELLS TARGETING MESOTHELIN

(71) Applicant: CARSGEN THERAPEUTICS CO., LTD, Shanghai (CN)

(72) Inventors: Huamao Wang, Shanghai (CN); Bo Song, Shanghai (CN); Peng Wang, Shanghai (CN)

(73) Assignee: CARSGEN THERAPEUTICS CO., LTD., Shanghai (CN)

( * ) Notice: Subject to any disclaimer, the term of this patent is extended or adjusted under 35 U.S.C. 154(b) by 67 days.

(21) Appl. No.: 15/754,076

(22) PCT Filed: Aug. 22, 2016

(86) PCT No.: PCT/CN2016/096292
§ 371 (c)(1),
(2) Date: Feb. 21, 2018

(87) PCT Pub. No.: WO2017/032293
PCT Pub. Date: Mar. 2, 2017

(65) Prior Publication Data
US 2018/0244796 A1     Aug. 30, 2018

(30) Foreign Application Priority Data
Aug. 21, 2015 (CN) .......................... 2015 1 0519214

(51) Int. Cl.
*C07K 16/30* (2006.01)
*A61P 35/00* (2006.01)
*A61K 39/395* (2006.01)
*C07K 14/725* (2006.01)
*C07K 14/705* (2006.01)

(52) U.S. Cl.
CPC ............ *C07K 16/30* (2013.01); *A61K 39/395* (2013.01); *A61P 35/00* (2018.01); *C07K 14/7051* (2013.01); *C07K 14/70517* (2013.01); *C07K 14/70521* (2013.01); *C07K 14/70578* (2013.01); *C07K 2317/21* (2013.01); *C07K 2317/24* (2013.01); *C07K 2317/56* (2013.01); *C07K 2317/565* (2013.01); *C07K 2317/622* (2013.01); *C07K 2317/73* (2013.01); *C07K 2319/02* (2013.01); *C07K 2319/03* (2013.01)

(58) Field of Classification Search
CPC ........ C07K 16/30; A61P 35/00; A61K 39/395
USPC .............. 424/133.1, 136.1, 178.1; 530/387.3
See application file for complete search history.

(56) References Cited

FOREIGN PATENT DOCUMENTS

| CN | 102458477 | 5/2012 |
|---|---|---|
| CN | 102458477 A | 5/2012 |
| CN | 103347897 | 10/2013 |
| CN | 103347897 A | 10/2013 |
| CN | 104151429 | 11/2014 |
| CN | 104151429 A | 11/2014 |
| WO | 2014031476 | 2/2014 |
| WO | 2014031476 A1 | 2/2014 |
| WO | 2014052064 | 4/2014 |
| WO | 2014052064 A1 | 4/2014 |
| WO | 2015090230 | 6/2015 |
| WO | 2015090230 A1 | 6/2015 |

OTHER PUBLICATIONS

Grupp et al., "Adoptive Cellular Therapy", cited from Current Topics in Microbiology and Immunology 344, Springer-Verlag Berlin Heidelberg 2011, published online Aug. 11, 2010; pp. 149-172 provided.
Davies et al., "Combining CD19 redirection and alloanergization to generate tumor-specific human T cells for allogeneic cell therapy of B-cell malignancies", cited from American Association from Cancer Research; pubished online first Apr. 27, 2010, pp. 3915-3924 provided.
Beatty et al., "Mesothelin-specific chimeric antigen receptor mRNA-engineered T cells induce anti-tumor activity in solid malignancies", cited from American Association for Cancer Research; published online first Dec. 19, 2013; 9 pages provided.
Maus et al., "T cells expressing chimeric antigen receptors can cause anaphylaxis in humans", cited from American Association for Cancer Research; published online first Apr. 7, 2013; pp. 26-31 provided.
International Search Report and Written Opinion (in Chinese and English) issued in PCT/CN2016/096292, dated Dec. 1, 2016, 21 pages provided.
International Search Report for international appl. No. PCT/CN2016/096292, dated Dec. 1, 2016 (8 pages including English translation).

*Primary Examiner* — Lynn A Bristol
(74) *Attorney, Agent, or Firm* — Hamre, Schumann, Mueller & Larson, P.C.

(57) ABSTRACT

The present invention provides fully human anti-mesothelin antibodies and immune effector cells targeting mesothelin.

30 Claims, 3 Drawing Sheets
Specification includes a Sequence Listing.

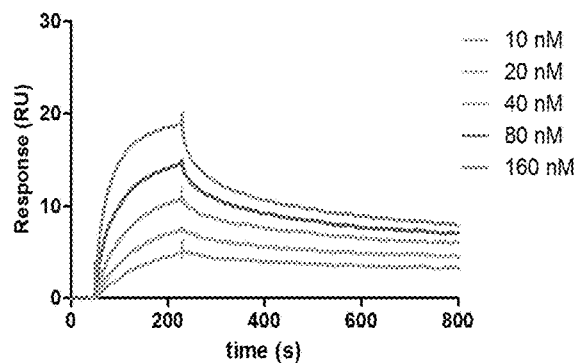
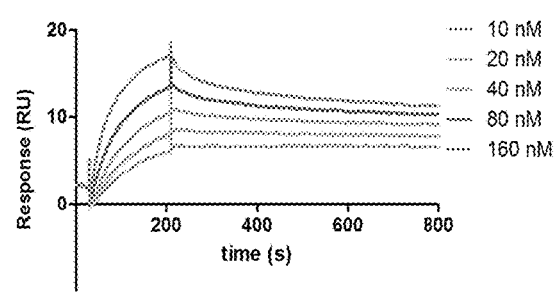
Fig. 5  Fig. 6
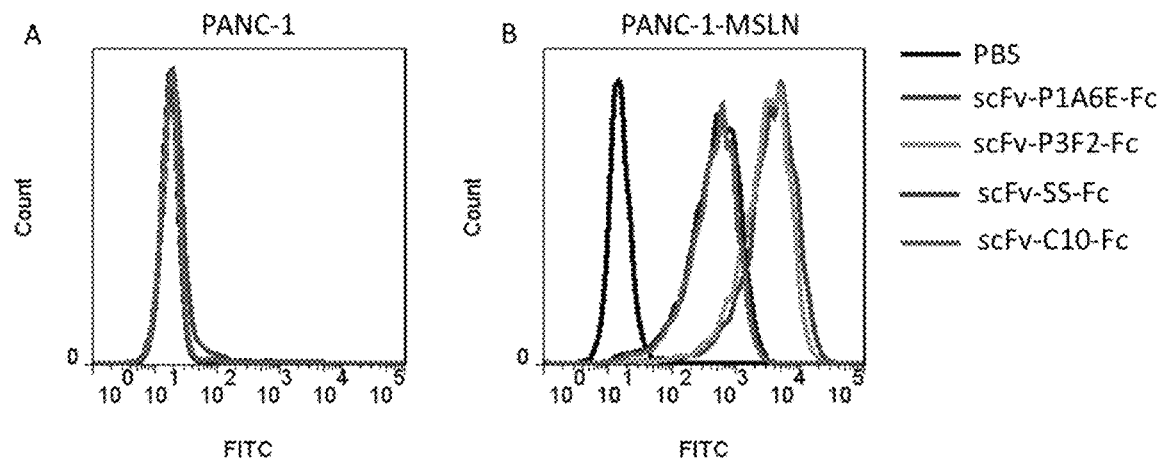
Fig. 7
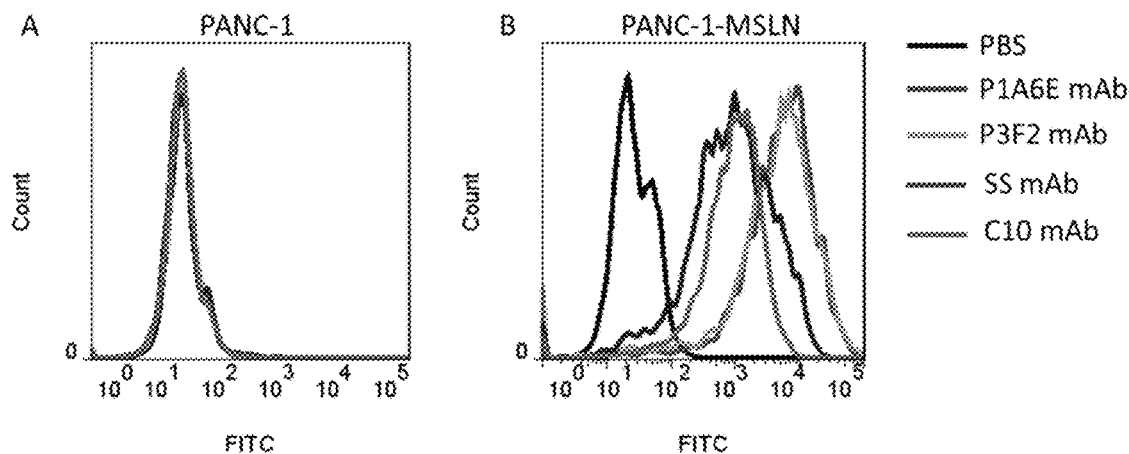
Fig. 8

SEQUENCE LISTING

<160> NUMBER OF SEQ ID NOS: 75

<210> SEQ ID NO 1
<211> LENGTH: 1068
<212> TYPE: DNA
<213> ORGANISM: Homo Sapiens

<400> SEQUENCE: 1

```
atgagggcct ggatcttctt tctcctttgc ctggccggga gggctctggc agccccgcta    60
gcagattaca aagacgatga cgacaaggaa gtggagaaga cagcctgtcc ttcaggcaag   120
aaggcccgcg agatagacga gagcctcatc ttctacaaga gtgggagct ggaagcctgc   180 gtggatgcgg ccctgctggc cacccagatg gaccgcgtga acgccatccc cttcacctac   240
gagcagctgg acgtcctaaa gcataaactg gatgagctct acccacaagg ttaccccgag   300
tctgtgatcc agcacctggg ctacctcttc ctcaagatga gccctgagga cattcgcaag   360
tggaatgtga cgtccctgga gaccctgaag gctttgcttg aagtcaacaa agggcacgaa   420
atgagtcctc aggtggccac cctgatcgac cgctttgtga agggaagggg ccagctagac   480
aaagacaccc tagacaccct gaccgccttc taccctgggt acctgtgctc cctcagcccc   540
```

```
gaggagctga gctccgtgcc ccccagcagc atctgggcgg tcaggcccca ggacctggac    600
acgtgtgacc caaggcagct ggacgtcctc tatcccaagg cccgccttgc tttccagaac    660
atgaacgggt ccgaatactt cgtgaagatc cagtccttcc tgggtggggc ccccacggag    720
gatttgaagg cgctcagtca gcagaatgtg agcatggact ggccacgtt catgaagctg     780 cggacggatg cggtgctgcc gttgactgtg gctgaggtgc agaaacttct gggaccccac    840
gtggagggcc tgaaggcgga ggagcggcac cgcccggtgc gggactggat cctacggcag    900
cggcaggacg acctggacac gctggggctg gggctacagg gcggcatccc caacggctac    960
ctggtcctag acctcagcat gcaagaggcc ctctcgggga cgccctgcct cctaggacct    1020
ggacctgttc tcaccgtcct ggcactgctc ctagcctcca ccctggcc                 1068
```

<210> SEQ ID NO 2
<211> LENGTH: 356
<212> TYPE: PRT
<213> ORGANISM: Homo Sapiens

<400> SEQUENCE: 2

```
Met Arg Ala Trp Ile Phe Phe Leu Leu Cys Leu Ala Gly Arg Ala Leu
1               5                   10                  15

Ala Ala Pro Leu Ala Asp Tyr Lys Asp Asp Asp Lys Glu Val Glu
            20                  25                  30

Lys Thr Ala Cys Pro Ser Gly Lys Ala Arg Glu Ile Asp Glu Ser
            35                  40                  45

Leu Ile Phe Tyr Lys Lys Trp Glu Leu Glu Ala Cys Val Asp Ala Ala
50                  55                  60

Leu Leu Ala Thr Gln Met Asp Arg Val Asn Ala Ile Pro Phe Thr Tyr
65                  70                  75                  80

Glu Gln Leu Asp Val Leu Lys His Lys Leu Asp Glu Leu Tyr Pro Gln
                85                  90                  95

Gly Tyr Pro Glu Ser Val Ile Gln His Leu Gly Tyr Leu Phe Leu Lys
            100                 105                 110

Met Ser Pro Glu Asp Ile Arg Lys Trp Asn Val Thr Ser Leu Glu Thr
        115                 120                 125

Leu Lys Ala Leu Leu Glu Val Asn Lys Gly His Glu Met Ser Pro Gln
130                 135                 140

Val Ala Thr Leu Ile Asp Arg Phe Val Lys Gly Arg Gly Gln Leu Asp
145                 150                 155                 160

Lys Asp Thr Leu Asp Thr Leu Thr Ala Phe Tyr Pro Gly Tyr Leu Cys
                165                 170                 175

Ser Leu Ser Pro Glu Glu Leu Ser Ser Val Pro Pro Ser Ser Ile Trp
            180                 185                 190

Ala Val Arg Pro Gln Asp Leu Asp Thr Cys Asp Pro Arg Gln Leu Asp
        195                 200                 205

Val Leu Tyr Pro Lys Ala Arg Leu Ala Phe Gln Asn Met Asn Gly Ser
210                 215                 220

Glu Tyr Phe Val Lys Ile Gln Ser Phe Leu Gly Gly Ala Pro Thr Glu
225                 230                 235                 240

Asp Leu Lys Ala Leu Ser Gln Gln Asn Val Ser Met Asp Leu Ala Thr
                245                 250                 255

Phe Met Lys Leu Arg Thr Asp Ala Val Leu Pro Leu Thr Val Ala Glu
            260                 265                 270

Val Gln Lys Leu Leu Gly Pro His Val Glu Gly Leu Lys Ala Glu Glu
```

```
                275                 280                 285
Arg His Arg Pro Val Arg Asp Trp Ile Leu Arg Gln Arg Gln Asp Asp
    290                 295                 300

Leu Asp Thr Leu Gly Leu Gly Leu Gln Gly Gly Ile Pro Asn Gly Tyr
305                 310                 315                 320

Leu Val Leu Asp Leu Ser Met Gln Glu Ala Leu Ser Gly Thr Pro Cys
                325                 330                 335

Leu Leu Gly Pro Gly Pro Val Leu Thr Val Leu Ala Leu Leu Leu Ala
            340                 345                 350

Ser Thr Leu Ala
        355

<210> SEQ ID NO 3
<211> LENGTH: 47
<212> TYPE: DNA
<213> ORGANISM: Artificial sequence
<220> FEATURE:
<221> NAME/KEY: misc_feature
<223> OTHER INFORMATION: primer

<400> SEQUENCE: 3
gcttacgcgt cctagcgcta ccggtcgcca ccatgagggc ctggatc                47

<210> SEQ ID NO 4
<211> LENGTH: 48
<212> TYPE: DNA
<213> ORGANISM: Artificial sequence
<220> FEATURE:
<221> NAME/KEY: misc_feature
<223> OTHER INFORMATION: primer

<400> SEQUENCE: 4
cgaggtcgac ctaggccagg gtggaggcta ggagcagtgc caggacgg             48

<210> SEQ ID NO 5
<211> LENGTH: 762
<212> TYPE: DNA
<213> ORGANISM: Homo Sapiens

<400> SEQUENCE: 5
caggtacagc tggaacagtc aggtctagga ctggtgaagc cctcgcagac cctctctctc     60
acctgtgcca tctccgggga cactgtctct agcgacagtg ctgcttggaa ctggatcagg    120
cagtccccat cgagaggcct tgagtggctg ggaaggacat actacaggtc caagtggttt    180
aatgattatg cagtatctgt gaaaggtcga ataaccatca actcagacac atccaagaac    240
cagttctccc tgcagttgaa ctctgtgact cccgaggaca cggctgtgta ttattgtgca    300
agaagtaata gttactacta ctacgctatg gacgtctggg gccaaggcac cctggtcacc    360
gtctcgagtg gtggaggcgg ttcaggcgga ggtggttctg gcggtggcgg atcgcaggct    420
gtgctgactc agccgtcttc cctctctgca tctcctggag catcagccag tctcacctgc    480
accttgcgca gtggcatcaa tgttggtatc tacaggatat actggtacca acagaggcca    540
gggagtcctc cccagattct cctgacttac aaatcagact cagataagta ccagggctct    600
ggagtcccca gtcgcttctc tggatccaaa gatgcttcgg ccaatgcagg gattttactc    660
atctctgggc tccagtctga agatgaggct gactattact gcatgatttg gcacagcggc    720
ggttgggtgt cggcggagg gaccaaggtc accgtcctag gt                         762

<210> SEQ ID NO 6
```

<211> LENGTH: 254
<212> TYPE: PRT
<213> ORGANISM: Homo Sapiens
<220> FEATURE:
<221> NAME/KEY: MISC_FEATURE
<223> OTHER INFORMATION: primer

<400> SEQUENCE: 6

```
Gln Val Gln Leu Glu Gln Ser Gly Leu Gly Leu Val Lys Pro Ser Gln
1               5                   10                  15

Thr Leu Ser Leu Thr Cys Ala Ile Ser Gly Asp Thr Val Ser Ser Asp
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Phe Asn Asp Tyr Ala
    50                  55                  60

Val Ser Val Lys Gly Arg Ile Thr Ile Asn Ser Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Ser Asn Ser Tyr Tyr Tyr Ala Met Asp Val
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Ser Gln Ala Val Leu Thr Gln
    130                 135                 140

Pro Ser Ser Leu Ser Ala Ser Pro Gly Ala Ser Ala Ser Leu Thr Cys
145                 150                 155                 160

Thr Leu Arg Ser Gly Ile Asn Val Gly Ile Tyr Arg Ile Tyr Trp Tyr
                165                 170                 175

Gln Gln Arg Pro Gly Ser Pro Pro Gln Ile Leu Leu Thr Tyr Lys Ser
            180                 185                 190

Asp Ser Asp Lys Tyr Gln Gly Ser Gly Val Pro Ser Arg Phe Ser Gly
        195                 200                 205

Ser Lys Asp Ala Ser Ala Asn Ala Gly Ile Leu Leu Ile Ser Gly Leu
    210                 215                 220

Gln Ser Glu Asp Glu Ala Asp Tyr Tyr Cys Met Ile Trp His Ser Gly
225                 230                 235                 240

Gly Trp Val Phe Gly Gly Gly Thr Lys Val Thr Val Leu Gly
                245                 250
```

<210> SEQ ID NO 7
<211> LENGTH: 741
<212> TYPE: DNA
<213> ORGANISM: Homo Sapiens

<400> SEQUENCE: 7

```
cagatgcagc tagtgcagtc tgggctgag gtgaagaagc ctggggcctc agtgaaggtt      60
tcctgcaagg catctggata caccttcacc agctactata tgcactgggt gcgacaggcc    120
cctggacaag gcttgagtg gatgggaata atcaaccta gtggtggtag cacaagctac      180
gcacagaagt tccagggcag agtcaccatg accagggaca cgtccacgag cacagtctac    240
atggagctga gcagcctgag atctgaggac acggccgtgt attactgtgc gagtagtcgg    300
agtgggacta cggtggtaaa tcatgatgct tttgatatct ggggaaagg gaccacggtc     360 accgtctcga gtggtggagg cggttcaggc ggaggtggtt ctggcggtgg cggatcggac    420
```

```
atccagttga cccagtctcc atcctccctg tctgcgtctg taggagacag agtcaccatc    480
acttgccggg caagccaggt cattagccgt gctttagcct ggtatcaaca aacaccaggg    540
aaacctccta aactcctgat ctatgatgcc tccaatttgc agagtggggt cccatcaagg    600
ttcagcggca gtggatctgg gacagatttc actctcacca tcagccgcct gcagcctgaa    660
gattttgcaa cttattactg tcaacagttt aatagttacc ctctcacttt cggcggaggg    720
accaagctgg agatcaaacg t                                              741
```

```
<210> SEQ ID NO 8
<211> LENGTH: 247
<212> TYPE: PRT
<213> ORGANISM: Homo Sapiens

<400> SEQUENCE: 8
```

Gln Met Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Ser Arg Ser Gly Thr Val Val Asn His Asp Ala Phe Asp
            100                 105                 110

Ile Trp Gly Lys Gly Thr Thr Val Thr Val Ser Gly Gly Gly
        115                 120                 125

Ser Gly Gly Gly Gly Ser Gly Gly Gly Gly Ser Asp Ile Gln Leu Thr
    130                 135                 140

Gln Ser Pro Ser Ser Leu Ser Ala Ser Val Gly Asp Arg Val Thr Ile
145                 150                 155                 160

Thr Cys Arg Ala Ser Gln Val Ile Ser Arg Ala Leu Ala Trp Tyr Gln
                165                 170                 175

Gln Thr Pro Gly Lys Pro Pro Lys Leu Leu Ile Tyr Asp Ala Ser Asn
            180                 185                 190

Leu Gln Ser Gly Val Pro Ser Arg Phe Ser Gly Ser Gly Ser Gly Thr
        195                 200                 205

Asp Phe Thr Leu Thr Ile Ser Arg Leu Gln Pro Glu Asp Phe Ala Thr
    210                 215                 220

Tyr Tyr Cys Gln Gln Phe Asn Ser Tyr Pro Leu Thr Phe Gly Gly Gly
225                 230                 235                 240

Thr Lys Leu Glu Ile Lys Arg
                245

```
<210> SEQ ID NO 9
<211> LENGTH: 30
<212> TYPE: DNA
<213> ORGANISM: Artificial sequence
<220> FEATURE:
<221> NAME/KEY: misc_feature
<223> OTHER INFORMATION: primer

<400> SEQUENCE: 9
```
acagtgctag cacaggtaca gctggaacag                                    30

<210> SEQ ID NO 10
<211> LENGTH: 27
<212> TYPE: DNA
<213> ORGANISM: Artificial sequence
<220> FEATURE:
<221> NAME/KEY: misc_feature
<223> OTHER INFORMATION: primer

<400> SEQUENCE: 10
ttgtcggatc cacctaggac ggtgacc                                       27

<210> SEQ ID NO 11
<211> LENGTH: 28
<212> TYPE: DNA
<213> ORGANISM: Artificial sequence
<220> FEATURE:
<221> NAME/KEY: misc_feature
<223> OTHER INFORMATION: primer

<400> SEQUENCE: 11
acagtgctag cacagatgca gctagtgc                                      28

<210> SEQ ID NO 12
<211> LENGTH: 27
<212> TYPE: DNA
<213> ORGANISM: Artificial sequence
<220> FEATURE:
<221> NAME/KEY: misc_feature
<223> OTHER INFORMATION: primer

<400> SEQUENCE: 12
ttgtcggatc cacgtttgat ctccagc                                       27

<210> SEQ ID NO 13
<211> LENGTH: 41
<212> TYPE: DNA
<213> ORGANISM: Artificial sequence
<220> FEATURE:
<221> NAME/KEY: misc_feature
<223> OTHER INFORMATION: primer

<400> SEQUENCE: 13
gcctttcctg gtttcctgtc tcaggtacag ctggaacagt c                       41

<210> SEQ ID NO 14
<211> LENGTH: 38
<212> TYPE: DNA
<213> ORGANISM: Artificial sequence
<220> FEATURE:
<221> NAME/KEY: misc_feature
<223> OTHER INFORMATION: primer

<400> SEQUENCE: 14
gatgggccct tggtggaggc actcgagacg gtgaccag                           38

<210> SEQ ID NO 15
<211> LENGTH: 22
<212> TYPE: DNA
<213> ORGANISM: Artificial sequence
<220> FEATURE:
<221> NAME/KEY: misc_feature
<223> OTHER INFORMATION: primer

<400> SEQUENCE: 15
ggctaactag agaacccact gc                                            22

```
<210> SEQ ID NO 16
<211> LENGTH: 21
<212> TYPE: DNA
<213> ORGANISM: Artificial sequence
<220> FEATURE:
<221> NAME/KEY: misc_feature
<223> OTHER INFORMATION: primer

<400> SEQUENCE: 16
agacaggaaa ccaggaaagg c                                              21

<210> SEQ ID NO 17
<211> LENGTH: 20
<212> TYPE: DNA
<213> ORGANISM: Artificial sequence
<220> FEATURE:
<221> NAME/KEY: misc_feature
<223> OTHER INFORMATION: primer

<400> SEQUENCE: 17
gcctccacca agggcccatc                                                20

<210> SEQ ID NO 18
<211> LENGTH: 21
<212> TYPE: DNA
<213> ORGANISM: Artificial sequence
<220> FEATURE:
<221> NAME/KEY: misc_feature
<223> OTHER INFORMATION: primer

<400> SEQUENCE: 18
gacaatctta gcgcagaagt c                                              21

<210> SEQ ID NO 19
<211> LENGTH: 42
<212> TYPE: DNA
<213> ORGANISM: Artificial sequence
<220> FEATURE:
<221> NAME/KEY: misc_feature
<223> OTHER INFORMATION: primer

<400> SEQUENCE: 19
ctttggtttc caggtgcaag atgtcaggct gtgctgactc ag                       42

<210> SEQ ID NO 20
<211> LENGTH: 43
<212> TYPE: DNA
<213> ORGANISM: Artificial sequence
<220> FEATURE:
<221> NAME/KEY: misc_feature
<223> OTHER INFORMATION: primer

<400> SEQUENCE: 20
gaagacagat ggtgcagcca ccgtacctag gacggtgacc ttg                      43

<210> SEQ ID NO 21
<211> LENGTH: 22
<212> TYPE: DNA
<213> ORGANISM: Artificial sequence
<220> FEATURE:
<221> NAME/KEY: misc_feature
<223> OTHER INFORMATION: primer

<400> SEQUENCE: 21
ggctaactag agaacccact gc                                             22
```

<210> SEQ ID NO 22
<211> LENGTH: 24
<212> TYPE: DNA
<213> ORGANISM: Artificial sequence
<220> FEATURE:
<221> NAME/KEY: misc_feature
<223> OTHER INFORMATION: primer

<400> SEQUENCE: 22
acatcttgca cctggaaacc aaag                                          24

<210> SEQ ID NO 23
<211> LENGTH: 24
<212> TYPE: DNA
<213> ORGANISM: Artificial sequence
<220> FEATURE:
<221> NAME/KEY: misc_feature
<223> OTHER INFORMATION: primer

<400> SEQUENCE: 23
acggtggctg caccatctgt cttc                                          24

<210> SEQ ID NO 24
<211> LENGTH: 21
<212> TYPE: DNA
<213> ORGANISM: Artificial sequence
<220> FEATURE:
<221> NAME/KEY: misc_feature
<223> OTHER INFORMATION: primer

<400> SEQUENCE: 24
gacaatctta gcgcagaagt c                                             21

<210> SEQ ID NO 25
<211> LENGTH: 22
<212> TYPE: DNA
<213> ORGANISM: Artificial sequence
<220> FEATURE:
<221> NAME/KEY: misc_feature
<223> OTHER INFORMATION: primer

<400> SEQUENCE: 25
gcaggggaaa gaatagtaga ca                                            22

<210> SEQ ID NO 26
<211> LENGTH: 56
<212> TYPE: DNA
<213> ORGANISM: Artificial sequence
<220> FEATURE:
<221> NAME/KEY: misc_feature
<223> OTHER INFORMATION: primer

<400> SEQUENCE: 26
aggccagcgg caggagcaag gcggtcactg gtaaggccat ggtggcgacc ggtagc       56

<210> SEQ ID NO 27
<211> LENGTH: 56
<212> TYPE: DNA
<213> ORGANISM: Artificial sequence
<220> FEATURE:
<221> NAME/KEY: misc_feature
<223> OTHER INFORMATION: primer

<400> SEQUENCE: 27
ctcctgccgc tggccttgct gctccacgcc gccaggccgc aggtacagct ggaaca       56

-continued

```
<210> SEQ ID NO 28
<211> LENGTH: 35
<212> TYPE: DNA
<213> ORGANISM: Artificial sequence
<220> FEATURE:
<221> NAME/KEY: misc_feature
<223> OTHER INFORMATION: primer

<400> SEQUENCE: 28
gcggcgctgg cgtcgtggta cctaggacgg tgacc                               35

<210> SEQ ID NO 29
<211> LENGTH: 56
<212> TYPE: DNA
<213> ORGANISM: Artificial sequence
<220> FEATURE:
<221> NAME/KEY: misc_feature
<223> OTHER INFORMATION: primer

<400> SEQUENCE: 29
ctcctgccgc tggccttgct gctccacgcc gccaggccgc agatgcagct agtgca        56

<210> SEQ ID NO 30
<211> LENGTH: 34
<212> TYPE: DNA
<213> ORGANISM: Artificial sequence
<220> FEATURE:
<221> NAME/KEY: misc_feature
<223> OTHER INFORMATION: primer

<400> SEQUENCE: 30
gcggcgctgg cgtcgtggta cgtttgatct ccag                                34

<210> SEQ ID NO 31
<211> LENGTH: 1566
<212> TYPE: DNA
<213> ORGANISM: Artificial sequence
<220> FEATURE:
<221> NAME/KEY: misc_feature
<223> OTHER INFORMATION: P1A6E-delta Z polynucleotide

<400> SEQUENCE: 31 gcagggaaa gaatagtaga cataatagca acagacatac aaactaaaga attacaaaaa     60
caaattacaa aaattcaaaa ttttccgatc acgagactag cctcgagaag cttgatcgat   120
ggctccggtg cccgtcagtg ggcagagcgc acatcgccca cagtcccga gaagttgggg    180 ggaggggtcg gcaattgaac cggtgcctag agaaggtggc gcggggtaaa ctgggaaagt   240
gatgtcgtgt actggctccg ccttttttccc gagggtgggg gagaaccgta tataagtgca  300
gtagtcgccg tgaacgttct ttttcgcaac gggtttgccg ccagaacaca ggtgtcgtga   360
cgcggatcca ggcctaagct tacgcgtcct agcgctaccg gtcgccacca tggccttacc   420
agtgaccgcc ttgctcctgc cgctggcctt gctgctccac gccgccaggc cgcaggtaca   480
gctggaacag tcaggtctag gactggtgaa gccctcgcag accctctctc tcacctgtgc   540
catctccggg gacactgtct ctagcgacag tgctgcttgg aactggatca ggcagtcccc   600
atcgagaggc cttgagtggc tgggaaggac atactacagg tccaagtggt ttaatgatta   660
tgcagtatct gtgaaaggtc gaataaccat caactcagac acatccaaga accagttctc   720
cctgcagttg aactctgtga ctcccgagga cacggctgtg tattattgtg caagaagtaa   780
tagttactac tactacgcta tggacgtctg gggccaaggc accctggtca ccgtctcgag   840
tggtggaggc ggttcaggcg gaggtggttc tggcggtggc ggatcgcagg ctgtgctgac  900
```

```
tcagccgtct tccctctctg catctcctgg agcatcagcc agtctcacct gcaccttgcg      960
cagtggcatc aatgttggta tctacaggat atactggtac caacagaggc cagggagtcc     1020
tccccagatt ctcctgactt acaaatcaga ctcagataag taccagggct ctggagtccc     1080
cagtcgcttc tctggatcca agatgcttc ggccaatgca gggattttac tcatctctgg      1140
gctccagtct gaagatgagg ctgactatta ctgcatgatt tggcacagcg gcggttgggt     1200
gttcggcgga gggaccaagg tcaccgtcct aggtaccacg acgccagcgc cgcgaccacc     1260
aacaccggcg cccaccatcg cgtcgcagcc cctgtccctg cgcccagagg cgtgccggcc     1320
agcggcgggg ggcgcagtgc acacgagggg gctggacttc gcctgtgata tctacatctg     1380
ggcgcccttg gccgggactt gtggggtcct tctcctgtca ctggttatca ccagagtgaa     1440
gttcagcagg agcgcagacg cccccgcgta ggtcgacctc gagggaattc cgataatcaa     1500
cctctggatt acaaaatttg tgaaagattg actggtattc ttaactatgt tgctccttt      1560 acgcta                                                                1566
```

<210> SEQ ID NO 32
<211> LENGTH: 1869
<212> TYPE: DNA
<213> ORGANISM: Artificial sequence
<220> FEATURE:
<221> NAME/KEY: misc_feature
<223> OTHER INFORMATION: P1A6E-Z polynucleotide

<400> SEQUENCE: 32

```
gcaggggaaa gaatagtaga cataatagca acagacatac aaactaaaga attacaaaaa       60
caaattacaa aaattcaaaa ttttccgatc acgagactag cctcgagaag cttgatcgat      120
ggctccggtg cccgtcagtg gcagagcgc acatcgccca cagtcccga gaagttgggg        180 ggaggggtcg gcaattgaac cggtgcctag agaaggtggc gcggggtaaa ctgggaaagt      240
gatgtcgtgt actggctccg ccttttttcc gagggtgggg gagaaccgta tataagtgca      300
gtagtcgccg tgaacgttct ttttcgcaac gggtttgccg ccagaacaca ggtgtcgtga      360
cgcggatcca ggcctaagct tacgcgtcct agcgctaccg gtcgccacca tggccttacc     420
agtgaccgcc ttgctcctgc cgctggcctt gctgctccac gccgccaggc cgcaggtaca      480
gctggaacag tcaggtctag gactggtgaa gccctcgcag accctctctc tcacctgtgc     540
catctccggg gacactgtct ctagcgacag tgctgcttgg aactggatca ggcagtcccc      600
atcgagaggc cttgagtggc tgggaaggac atactacagg tccaagtggt ttaatgatta     660
tgcagtatct gtgaaaggtc gaataaccat caactcagac acatccaaga ccagttctc      720 cctgcagttg aactctgtga ctcccgagga cacggctgtg tattattgtg caagaagtaa     780
tagttactac tactacgcta tggacgtctg gggccaaggc accctggtca ccgtctcgag      840
tggtggaggc ggttcaggcg gaggtggttc tggcggtggc ggatcgcagg ctgtgctgac     900
tcagccgtct tccctctctg catctcctgg agcatcagcc agtctcacct gcaccttgcg      960
cagtggcatc aatgttggta tctacaggat atactggtac caacagaggc cagggagtcc     1020
tccccagatt ctcctgactt acaaatcaga ctcagataag taccagggct ctggagtccc     1080
cagtcgcttc tctggatcca agatgcttc ggccaatgca gggattttac tcatctctgg      1140
gctccagtct gaagatgagg ctgactatta ctgcatgatt tggcacagcg gcggttgggt     1200
gttcggcgga gggaccaagg tcaccgtcct aggtaccacg acgccagcgc cgcgaccacc     1260
aacaccggcg cccaccatcg cgtcgcagcc cctgtccctg cgcccagagg cgtgccggcc     1320
```

-continued

| | |
|---|---|
| agcggcgggg ggcgcagtgc acacgagggg gctggacttc gcctgtgata tctacatctg | 1380 |
| ggcgcccttg gccgggactt gtggggtcct tctcctgtca ctggttatca ccagagtgaa | 1440 |
| gttcagcagg agcgcagacg ccccgcgta ccagcagggc cagaaccagc tctataacga | 1500 |
| gctcaatcta ggacgaagag aggagtacga tgttttggac aagagacgtg gccgggaccc | 1560 |
| tgagatgggg ggaaagccgc agagaaggaa gaaccctcag gaaggcctgt acaatgaact | 1620 |
| gcagaaagat aagatggcgg aggcctacag tgagattggg atgaaaggcg agcgccggag | 1680 |
| gggcaagggg cacgatggcc tttaccaggg tctcagtaca gccaccaagg acacctacga | 1740 |
| cgcccttcac atgcaggccc tgccccctcg ctaggtcgac ctcgagggaa ttccgataat | 1800 |
| caacctctgg attacaaaat ttgtgaaaga ttgactggta ttcttaacta tgttgctcct | 1860 |
| tttacgcta | 1869 |

<210> SEQ ID NO 33
<211> LENGTH: 2001
<212> TYPE: DNA
<213> ORGANISM: Artificial sequence
<220> FEATURE:
<221> NAME/KEY: misc_feature
<223> OTHER INFORMATION: P1A6E-BBZ polynucleotide

<400> SEQUENCE: 33

| | |
|---|---|
| gcagggaaaa gaatagtaga cataatagca acagacatac aaactaaaga attacaaaaa | 60 |
| caaattacaa aaattcaaaa ttttccgatc acgagactag cctcgagaag cttgatcgat | 120 |
| ggctccggtg cccgtcagtg ggcagagcgc acatcgccca cagtccccga gaagttgggg | 180 |
| ggaggggtcg gcaattgaac cggtgcctag agaaggtggc gcggggtaaa ctgggaaagt | 240 |
| gatgtcgtgt actggctccg cctttttccc gagggtgggg gagaaccgta tataagtgca | 300 |
| gtagtcgccg tgaacgttct ttttcgcaac gggtttgccg ccagaacaca ggtgtcgtga | 360 |
| cgcggatcca ggcctaagct tacgcgtcct agcgctaccg gtcgccacca tggccttacc | 420 |
| agtgaccgcc ttgctcctgc cgctggcctt gctgctccac gccgccaggc cgcaggtaca | 480 |
| gctggaacag tcaggtctag gactggtgaa gccctgcag accctctctc tcacctgtgc | 540 |
| catctccggg gacactgtct ctagcgacag tgctgcttgg aactggatca ggcagtcccc | 600 |
| atcgagaggc cttgagtggc tgggaaggac atactacagg tccaagtggt ttaatgatta | 660 |
| tgcagtatct gtgaaaggtc gaataaccat caactcagac acatccaaga accagttctc | 720 |
| cctgcagttg aactctgtga ctcccgagga cacggctgtg tattattgtg caagaagtaa | 780 |
| tagttactac tactacgcta tggacgtctg gggccaaggc accctggtca ccgtctcgag | 840 |
| tggtggaggc ggttcaggcg gaggtggttc tggcggtggc ggatcgcagg ctgtgctgac | 900 |
| tcagccgtct tccctctctg catctcctgg agcatcagcc agtctcacct gcaccttgcg | 960 |
| cagtggcatc aatgttggta tctacaggat atactggtac aacagagggc agggagtcc | 1020 |
| tcccagatt ctcctgactt acaaatcaga ctcagataag taccagggct ctggagtccc | 1080 |
| cagtcgcttc tctggatcca agatgcttc ggccaatgca gggattttac tcatctctgg | 1140 |
| gctccagtct gaagatgagg ctgactatta ctgcatgatt tggcacagcg gcggttgggt | 1200 |
| gttcggcgga gggaccaagg tcaccgtcct aggtaccacg acgccagcgc gcgaccacc | 1260 |
| aacaccggcg cccaccatcg cgtcgcagcc cctgtccctg cgcccagagg cgtgccggcc | 1320 |
| agcggcgggg ggcgcagtgc acacgagggg gctggacttc gcctgtgata tctacatctg | 1380 |
| ggcgcccttg gccgggactt gtggggtcct tctcctgtca ctggttatca cccttactg | 1440 |

```
caaacggggc agaaagaaac tcctgtatat attcaaacaa ccatttatga gaccagtaca    1500
aactactcaa gaggaagatg gctgtagctg ccgatttcca gaagaagaag aaggaggatg    1560
tgaactgaga gtgaagttca gcaggagcgc agacgccccc gcgtacaagc agggccagaa    1620
ccagctctat aacagctca atctaggacg aagagaggag tacgatgttt tggacaagag    1680
acgtggccgg gaccctgaga tgggggaaa gccgagaagg aagaaccctc aggaaggcct     1740
gtacaatgaa ctgcagaaag ataagatggc ggaggcctac agtgagattg ggatgaaagg    1800
cgagcgccgg aggggcaagg gcacgatgg cctttaccag ggtctcagta cagccaccaa    1860
ggacacctac gacgcccttc acatgcaggc cctgccccct cgctaggtcg acctcgaggg    1920
aattccgata atcaacctct ggattacaaa atttgtgaaa gattgactgg tattcttaac    1980
tatgttgctc cttttacgct a                                               2001
```

<210> SEQ ID NO 34
<211> LENGTH: 2010
<212> TYPE: DNA
<213> ORGANISM: Artificial sequence
<220> FEATURE:
<221> NAME/KEY: misc_feature
<223> OTHER INFORMATION: P1A6E-28Z polynucleotide

<400> SEQUENCE: 34

```
gcaggggaaa gaatagtaga cataatagca acagacatac aaactaaaga attacaaaaa    60
caaattacaa aaattcaaaa tttccgatc acgagactag cctcgagaag cttgatcgat    120
ggctccggtg cccgtcagtg ggcagagcgc acatcgccca cagtccccga gaagttgggg    180
ggaggggtcg gcaattgaac cggtgcctag agaaggtggc gcggggtaaa ctgggaaagt    240
gatgtcgtgt actggctccg cctttttccc gagggtgggg gagaaccgta tataagtgca    300
gtagtcgccg tgaacgttct ttttcgcaac gggtttgccg ccagaacaca ggtgtcgtga    360
cgcggatcca ggcctaagct tacgcgtcct agcgctaccg gtcgccacca tggccttacc    420
agtgaccgcc ttgctcctgc cgctggcctt gctgctccac gccgccaggc cgcaggtaca    480
gctggaacag tcaggtctag gactggtgaa gccctcgcag accctctctc tcacctgtgc    540
catctccggg gacactgtct ctagcgacag tgctgcttgg aactggatca ggcagtcccc    600
atcgagaggc cttgagtggc tgggaaggac atactacagg tccaagtggt ttaatgatta    660
tgcagtatct gtgaaaggtc gaataaccat caactcagac acatccaaga accagttctc    720
cctgcagttg aactctgtga ctcccgagga cacggctgtg tattattgtg caagaagtaa    780
tagttactac tactacgcta tggacgtctg ggccaaggc accctggtca ccgtctcgag    840
tggtggaggc ggttcaggcg gaggtggttc tggcggtggc ggatcgcagg ctgtgctgac    900
tcagccgtct ccctctctg catctcctgg agcatcagcc agtctcacct gcaccttgcg    960
cagtggcatc aatgttggta tctacaggat atactggtac caacagaggc agggagtcc    1020 tcccagatt ctcctgactt acaaatcaga ctcagataag taccagggct ctggagtccc    1080
cagtcgcttc tctggatcca agatgcttc ggccaatgca gggattttac tcatctctgg    1140
gctccagtct gaagatgagg ctgactatta ctgcatgatt tggcacagcg gcggttgggt    1200
gttcggcgga gggaccaagg tcaccgtcct aggtaccacg acgccagcgc cgcgaccacc    1260
aacaccggcg cccaccatcg cgtcgcagcc cctgtccctg cgcccagagg cgtgccggcc    1320
agcggcgggg ggcgcagtgc acacgagggg gctggacttc gcctgtgatt tttgggtgct    1380
ggtggtggtt ggtggagtcc tggcttgcta tagcttgcta gtaacagtgg cctttattat    1440
```

```
tttctgggtg aggagtaaga ggagcaggct cctgcacagt gactacatga acatgactcc    1500
ccgccgcccc gggccaaccc gcaagcatta ccagccctat gccccaccac gcgacttcgc    1560
agcctatcgc tccagagtga agttcagcag gagcgcagac gcccccgcgt accagcaggg    1620
ccagaaccag ctctataacg agctcaatct aggacgaaga gaggagtacg atgttttgga    1680
caagagacgt ggccgggacc ctgagatggg gggaaagccg cagagaagga agaaccctca    1740
ggaaggcctg tacaatgaac tgcagaaaga taagatggcg gaggcctaca gtgagattgg    1800
gatgaaaggc gagcgccgga ggggcaaggg gcacgatggc ctttaccagg gtctcagtac    1860
agccaccaag gacacctacg acgcccttca catgcaggcc ctgccccctc gctaggtcga    1920
cctcgaggga attccgataa tcaacctctg gattacaaaa tttgtgaaag attgactggt    1980
attcttaact atgttgctcc ttttacgcta                                     2010

<210> SEQ ID NO 35
<211> LENGTH: 2136
<212> TYPE: DNA
<213> ORGANISM: Artificial sequence
<220> FEATURE:
<221> NAME/KEY: misc_feature
<223> OTHER INFORMATION: P1A6E-28BBZ polynucleotide

<400> SEQUENCE: 35 gcagggaaa gaatagtaga cataatagca acagacatac aaactaaaga attacaaaaa      60
caaattacaa aaattcaaaa ttttccgatc acgagactag cctcgagaag cttgatcgat    120
ggctccggtg cccgtcagtg ggcagagcgc acatcgccca cagtccccga gaagttgggg    180
ggaggggtcg gcaattgaac cggtgcctag agaaggtggc gcggggtaaa ctgggaaagt    240
gatgtcgtgt actggctccg cctttttccc gagggtgggg gagaaccgta tataagtgca    300
gtagtcgccg tgaacgttct ttttcgcaac gggtttgccg ccagaacaca ggtgtcgtga    360
cgcggatcca ggcctaagct tacgcgtcct agcgctaccg gtcgccacca tggccttacc    420
agtgaccgcc ttgctcctgc cgctggcctt gctgctccac gccgccaggc cgcaggtaca    480
gctggaacag tcaggtctag gactggtgaa gccctcgcag accctctctc tcacctgtgc    540
catctccggg gacactgtct ctagcgacag tgctgcttgg aactggatca ggcagtcccc    600
atcgagaggc cttgagtggc tgggaaggac atactacagg tccaagtggt ttaatgatta    660
tgcagtatct gtgaaaggtc gaataaccat caactcagac acatccaaga accagttctc    720
cctgcagttg aactctgtga ctcccgagga cacggctgtg tattattgtg caagaagtaa    780
tagttactac tactacgcta tggacgtctg gggccaaggc accctggtca ccgtctcgag    840
tggtggaggc ggttcaggcg gaggtggttc tggcggtggc ggatcgcagg ctgtgctgac    900
tcagccgtct ccctctctg catctcctgg agcatcagcc agtctcacct gcaccttgcg    960
cagtggcatc aatgttggta tctacaggat atactggtac aacagaggc agggagtcc    1020 tcccagatt ctcctgactt acaaatcaga ctcagataag taccagggct ctggagtccc    1080
cagtcgcttc tctggatcca agatgcttc ggccaatgca gggattttac tcatctctgg    1140
gctccagtct gaagatgagg ctgactatta ctgcatgatt tggcacagcg gcggttgggt    1200
gttcggcgga gggaccaagg tcaccgtcct aggtaccacg acgccagcgc cgcgaccacc    1260
aacaccggcg cccaccatcg cgtcgcagcc cctgtccctg cgcccagagg cgtgccggcc    1320
agcggcgggg ggcgcagtgc acacgagggg gctggacttc gcctgtgatt tttggtgcct    1380
ggtggtggtt ggtggagtcc tggcttgcta tagcttgcta gtaacagtgg cctttattat    1440
```

| | |
|---|---|
| tttctgggtg aggagtaaga ggagcaggct cctgcacagt gactacatga acatgactcc | 1500 |
| ccgccgcccc gggccaaccc gcaagcatta ccagccctat gccccaccac gcgacttcgc | 1560 |
| agcctatcgc tccaaacggg gcagaaagaa actcctgtat atattcaaac aaccatttat | 1620 |
| gagaccagta caaactactc aagaggaaga tggctgtagc tgccgatttc cagaagaaga | 1680 |
| agaaggagga tgtgaactga gagtgaagtt cagcaggagc gcagacgccc ccgcgtacca | 1740 |
| gcagggccag aaccagctct ataacgagct caatctagga cgaagagagg agtacgatgt | 1800 |
| tttggacaag agacgtggcc gggaccctga gatgggggga aagccgcaga aaggaagaa | 1860 |
| ccctcaggaa ggcctgtaca atgaactgca gaaagataag atggcggagg cctacagtga | 1920 |
| gattgggatg aaaggcgagc gccggagggg caaggggcac gatggccttt accagggtct | 1980 |
| cagtacagcc accaaggaca cctacgacgc ccttcacatg caggcctgc cccctcgcta | 2040 |
| ggtcgacctc gagggaattc cgataatcaa cctctggatt acaaaatttg tgaaagattg | 2100 |
| actggtattc ttaactatgt tgctcctttt acgcta | 2136 |

<210> SEQ ID NO 36
<211> LENGTH: 1545
<212> TYPE: DNA
<213> ORGANISM: Artificial sequence
<220> FEATURE:
<221> NAME/KEY: misc_feature
<223> OTHER INFORMATION: P3F2-delta Z polynucleotide

<400> SEQUENCE: 36

| | |
|---|---|
| gcagggaaa gaatagtaga cataatagca acagacatac aaactaaaga attacaaaaa | 60 |
| caaattacaa aaattcaaaa ttttccgatc acgagactag cctcgagaag cttgatcgat | 120 |
| ggctccggtg cccgtcagtg ggcagagcgc acatcgccca cagtcccga gaagttgggg | 180 |
| ggaggggtcg gcaattgaac cggtgcctag agaaggtggc gcggggtaaa ctgggaaagt | 240 |
| gatgtcgtgt actggctccg ccttttttccc gagggtgggg gagaaccgta tataagtgca | 300 |
| gtagtcgccg tgaacgttct ttttcgcaac gggtttgccg ccagaacaca ggtgtcgtga | 360 |
| cgcggatcca ggcctaagct tacgcgtcct agcgctaccg gtcgccacca tggccttacc | 420 |
| agtgaccgcc ttgctcctgc cgctggcctt gctgctccac gccgccaggc cgcagatgca | 480 |
| gctagtgcag tctggggctg aggtgaagaa gcctggggcc tcagtgaagg tttcctgcaa | 540 |
| ggcatctgga tacaccttca ccagctacta tatgcactgg gtgcgacagg cccctggaca | 600 |
| agggcttgag tggatgggaa taatcaaccc tagtggtggt agcacaagct acgcacagaa | 660 |
| gttccagggc agagtcacca tgaccaggga cacgtccacg agcacagtct acatggagct | 720 |
| gagcagcctg agatctgagg acacggccgt gtattactgt gcgagtagtc ggagtgggac | 780 |
| tacggtggta aatcatgatg ctttttgatat ctggggaaaa gggaccacgg tcaccgtctc | 840 |
| gagtggtgga ggcggttcag gcggaggtgg ttctggcggt ggcggatcgg acatccagtt | 900 |
| gacccagtct ccatcctccc tgtctgcgtc tgtaggagac agagtcacca tcacttgccg | 960 |
| ggcaagccag gtcattagcc gtgctttagc ctggtatcaa caaacaccag ggaaacctcc | 1020 |
| taaactcctg atctatgatg cctccaattt gcagagtggg gtcccatcaa ggttcagcgg | 1080 |
| cagtggatct gggacagatt tcactctcac catcagccgc ctgcagcctg aagattttgc | 1140 |
| aacttattac tgtcaacagt ttaatagtta ccctctcact ttcggcggag ggaccaagct | 1200 |
| ggagatcaaa cgtaccacga cgccagcgcc gcgaccacca caccggcgc ccaccatcgc | 1260 |
| gtcgcagccc ctgtccctgc gcccagaggc gtgccggcca gcggcggggg gcgcagtgca | 1320 |

```
cacgagggg  ctggacttcg  cctgtgatat  ctacatctgg  gcgcccttgg  ccgggacttg    1380
tggggtcctt  ctcctgtcac  tggttatcac  cagagtgaag  ttcagcagga  gcgcagacgc    1440
ccccgcgtag  gtcgacctcg  agggaattcc  gataatcaac  ctctggatta  caaaatttgt    1500
gaaagattga  ctggtattct  taactatgtt  gctccttta  cgcta                      1545

<210> SEQ ID NO 37
<211> LENGTH: 1848
<212> TYPE: DNA
<213> ORGANISM: Artificial sequence
<220> FEATURE:
<221> NAME/KEY: misc_feature
<223> OTHER INFORMATION: P3F2-Z polynucleotide

<400> SEQUENCE: 37 gcagggaaa   gaatagtaga  cataatagca  acagacatac  aaactaaaga  attacaaaaa     60
caaattacaa  aaattcaaaa  ttttccgatc  acgagactag  cctcgagaag  cttgatcgat    120
ggctccggtg  cccgtcagtg  ggcagagcgc  acatcgccca  cagtcccga   gaagttgggg    180 ggaggggtcg  gcaattgaac  cggtgcctag  agaaggtggc  gcggggtaaa  ctgggaaagt    240
gatgtcgtgt  actggctccg  cctttttccc  gagggtgggg  gagaaccgta  tataagtgca    300
gtagtcgccg  tgaacgttct  ttttcgcaac  gggtttgccg  ccagaacaca  ggtgtcgtga    360
cgcggatcca  ggcctaagct  tacgcgtcct  agcgctaccg  gtcgccacca  tggccttacc    420
agtgaccgcc  ttgctcctgc  cgctggcctt  gctgctccac  gccgccaggc  cgcagatgca    480
gctagtgcag  tctggggctg  aggtgaagaa  gcctggggcc  tcagtgaagg  tttcctgcaa    540
ggcatctgga  tacaccttca  ccagctacta  tatgcactgg  gtgcgacagg  cccctggaca    600
agggcttgag  tggatgggaa  taatcaaccc  tagtggtggt  agcacaagct  acgcacagaa    660
gttccagggc  agagtcacca  tgaccaggga  cacgtccacg  agcacagtct  acatggagct    720
gagcagcctg  agatctgagg  acacggccgt  gtattactgt  gcgagtagtc  ggagtgggac    780
tacggtggta  aatcatgatg  cttttgatat  ctggggaaaa  gggaccacgg  tcaccgtctc    840
gagtggtgga  ggcggttcag  gcggaggtgg  ttctggcggt  ggcggatcgg  acatccagtt    900
gacccagtct  ccatcctccc  tgtctgcgtc  tgtaggagac  agagtcacca  tcacttgccg    960
ggcaagccag  gtcattagcc  gtgctttagc  ctggtatcaa  caaacaccag  ggaaacctcc    1020
taaactcctg  atctatgatg  cctccaattt  gcagagtggg  gtcccatcaa  ggttcagcgg    1080
cagtggatct  gggacagatt  tcactctcac  catcagccgc  ctgcagcctg  aagattttgc    1140
aacttattac  tgtcaacagt  ttaatagtta  ccctctcact  ttcggcggag  ggaccaagct    1200
ggagatcaaa  cgtaccacga  cgccagcgcc  gcgaccacca  acaccggcgc  ccaccatcgc    1260
gtcgcagccc  ctgtccctgc  gcccagaggc  gtgccggcca  gcggcggggg  gcgcagtgca    1320 cacgagggg   ctggacttcg  cctgtgatat  ctacatctgg  gcgcccttgg  ccgggacttg    1380
tggggtcctt  ctcctgtcac  tggttatcac  cagagtgaag  ttcagcagga  gcgcagacgc    1440
ccccgcgtac  cagcagggcc  agaaccagct  ctataacgag  ctcaatctag  gacgaagaga    1500
ggagtacgat  gttttggaca  agagacgtgg  ccgggaccct  gagatggggg  gaaagccgca    1560
gagaaggaag  aaccctcagg  aaggcctgta  caatgaactg  cagaaagata  agatggcgga    1620
ggcctacagt  gagattggga  tgaaaggcga  gcgccggagg  ggcaaggggc  acgatggcct    1680
ttaccagggt  ctcagtacag  ccaccaagga  cacctacgac  gcccttcaca  tgcaggccct    1740
gccccctcgc  taggtcgacc  tcgagggaat  tccgataatc  aaccctctgga  ttacaaaatt    1800
```

| | |
|---|---|
| tgtgaaagat tgactggtat tcttaactat gttgctcctt ttacgcta | 1848 |

<210> SEQ ID NO 38
<211> LENGTH: 1980
<212> TYPE: DNA
<213> ORGANISM: Artificial sequence
<220> FEATURE:
<221> NAME/KEY: misc_feature
<223> OTHER INFORMATION: P3F2-BBZ

<400> SEQUENCE: 38

| | |
|---|---|
| gcagggaaa gaatagtaga cataatagca acagacatac aaactaaaga attacaaaaa | 60 |
| caaattacaa aaattcaaaa ttttccgatc acgagactag cctcgagaag cttgatcgat | 120 |
| ggctccggtg cccgtcagtg ggcagagcgc acatcgccca cagtccccga gaagttgggg | 180 |
| ggaggggtcg gcaattgaac cggtgcctag agaaggtggc gcggggtaaa ctgggaaagt | 240 |
| gatgtcgtgt actggctccg cctttttccc gagggtgggg gagaaccgta tataagtgca | 300 |
| gtagtcgccg tgaacgttct ttttcgcaac gggtttgccg ccagaacaca ggtgtcgtga | 360 |
| cgcggatcca ggcctaagct tacgcgtcct agcgctaccg gtcgccacca tggccttacc | 420 |
| agtgaccgcc ttgctcctgc cgctggcctt gctgctccac gccgcaggc cgcagatgca | 480 |
| gctagtgcag tctggggctg aggtgaagaa gcctgggcc tcagtgaagg tttcctgcaa | 540 |
| ggcatctgga tacaccttca ccagctacta tatgcactgg gtgcgacagg cccctggaca | 600 |
| agggcttgag tggatgggaa taatcaaccc tagtggtggt agcacaagct acgcacagaa | 660 |
| gttccaggc agagtcacca tgaccaggga cacgtccacg agcacagtct acatggagct | 720 |
| gagcagcctg agatctgagg acacggccgt gtattactgt gcgagtagtc ggagtgggac | 780 |
| tacggtggta aatcatgatg cttttgatat ctgggggaaa gggaccacgg tcaccgtctc | 840 |
| gagtggtgga ggcggttcag gcggaggtgg ttctggcggt ggcggatcgg acatccagtt | 900 |
| gacccagtct ccatcctccc tgtctgcgtc tgtaggagac agagtcacca tcacttgccg | 960 |
| ggcaagccag gtcattagcc gtgctttagc ctggtatcaa caaacaccag ggaaacctcc | 1020 |
| taaactcctg atctatgatg cctccaatttt gcagagtggg gtcccatcaa ggttcagcgg | 1080 |
| cagtggatct gggacagatt tcactctcac catcagccgc ctgcagcctg aagattttgc | 1140 |
| aacttattac tgtcaacagt ttaatagtta ccctctcact ttcggcggag ggaccaagct | 1200 |
| ggagatcaaa cgtaccacga cgccagcgcc gcgaccacca caccggcgc ccaccatcgc | 1260 |
| gtcgcagccc ctgtccctgc gcccagaggc gtgccggcca gcggcggggg gcgcagtgca | 1320 |
| cacgaggggg ctggacttcg cctgtgatat ctacatctgg gcgcccttgg ccgggacttg | 1380 |
| tggggtcctt ctcctgtcac tggttatcac cctttactgc aaacgggca gaaagaaact | 1440 |
| cctgtatata ttcaaacaac catttatgag accagtacaa actactcaag gaagatgg | 1500 |
| ctgtagctgc cgatttccag aagaagaaga aggaggatgt gaactgagag tgaagttcag | 1560 |
| caggagcgca gacgcccccg cgtacaagca gggccagaac cagctctata cgagctcaa | 1620 |
| tctaggacga agagaggagt acgatgtttt ggacaagaga cgtggccggg accctgagat | 1680 |
| gggggaaag ccgagaagga agaaccctca ggaaggcctg tacaatgaac tgcagaaaga | 1740 |
| taagatggcg gaggcctaca gtgagattgg gatgaaaggc gagcgccgga ggggcaaggg | 1800 |
| gcacgatggc ctttaccagg gtctcagtac agccaccaag gacacctacg acgcccttca | 1860 |
| catgcaggcc ctgccccctc gctaggtcga cctcgaggga attccgataa tcaacctctg | 1920 |
| gattacaaaa tttgtgaaag attgactggt attcttaact atgttgctcc ttttacgcta | 1980 |

<210> SEQ ID NO 39
<211> LENGTH: 1989
<212> TYPE: DNA
<213> ORGANISM: Artificial sequence
<220> FEATURE:
<221> NAME/KEY: misc_feature
<223> OTHER INFORMATION: P3F2-28Z polynucleotide

<400> SEQUENCE: 39

| | | | | | |
|---|---|---|---|---|---|
| gcagggggaaa | gaatagtaga | cataatagca | acagacatac | aaactaaaga | attacaaaaa | 60 |
| caaattacaa | aaattcaaaa | ttttccgatc | acgagactag | cctcgagaag | cttgatcgat | 120 |
| ggctccggtg | cccgtcagtg | ggcagagcgc | acatcgccca | cagtcccga | gaagttgggg | 180 |
| ggaggggtcg | gcaattgaac | cggtgcctag | agaaggtggc | gcggggtaaa | ctgggaaagt | 240 |
| gatgtcgtgt | actggctccg | cctttttccc | gagggtgggg | gagaaccgta | tataagtgca | 300 |
| gtagtcgccg | tgaacgttct | ttttcgcaac | gggtttgccg | ccagaacaca | ggtgtcgtga | 360 |
| cgcggatcca | ggcctaagct | tacgcgtcct | agcgctaccg | gtcgccacca | tggccttacc | 420 |
| agtgaccgcc | ttgctcctgc | cgctggcctt | gctgctccac | gccgccaggc | cgcagatgca | 480 |
| gctagtgcag | tctggggctg | aggtgaagaa | gcctggggcc | tcagtgaagg | tttcctgcaa | 540 |
| ggcatctgga | tacaccttca | ccagctacta | tatgcactgg | gtgcgacagg | cccctggaca | 600 |
| agggcttgag | tggatgggaa | taatcaaccc | tagtggtggt | agcacaagct | acgcacagaa | 660 |
| gttccagggc | agagtcacca | tgaccaggga | cacgtccacg | agcacagtct | acatggagct | 720 |
| gagcagcctg | agatctgagg | acacggccgt | gtattactgt | gcgagtagtc | ggagtgggac | 780 |
| tacggtggta | aatcatgatg | cttttgatat | ctggggggaaa | gggaccacgg | tcaccgtctc | 840 |
| gagtggtgga | ggcggttcag | gcggaggtgg | ttctggcggt | ggcggatcgg | acatccagtt | 900 |
| gacccagtct | ccatcctccc | tgtctgcgtc | tgtaggagac | agagtcacca | tcacttgccg | 960 |
| ggcaagccag | gtcattagcc | gtgctttagc | ctggtatcaa | caaacaccag | ggaaacctcc | 1020 |
| taaactcctg | atctatgatg | cctccaattt | gcagagtggg | gtcccatcaa | ggttcagcgg | 1080 |
| cagtggatct | gggacagatt | tcactctcac | catcagccgc | ctgcagcctg | aagattttgc | 1140 |
| aacttattac | tgtcaacagt | ttaatagtta | ccctctcact | ttcggcggag | ggaccaagct | 1200 |
| ggagatcaaa | cgtaccacga | cgccagcgcc | gcgaccacca | acaccggcgc | ccaccatcgc | 1260 |
| gtcgcagccc | ctgtccctgc | gcccagaggc | gtgccggcca | gcggcggggg | gcgcagtgca | 1320 |
| cacgaggggg | ctggacttcg | cctgtgattt | ttgggtgctg | gtggtggttg | gtggagtcct | 1380 |
| ggcttgctat | agcttgctag | taacagtggc | ctttattatt | ttctgggtga | ggagtaagag | 1440 |
| gagcaggctc | ctgcacagtg | actacatgaa | catgactccc | cgccgccccg | ggccaacccg | 1500 |
| caagcattac | cagccctatg | ccccaccacg | cgacttcgca | gcctatcgct | ccagagtgaa | 1560 |
| gttcagcagg | agcgcagacg | cccccgcgta | ccagcagggc | cagaaccagc | tctataacga | 1620 |
| gctcaatcta | ggacgaagag | aggagtacga | tgttttggac | aagagacgtg | gccgggaccc | 1680 |
| tgagatgggg | ggaaagccgc | agagaaggaa | gaaccctcag | gaaggcctgt | acaatgaact | 1740 |
| gcagaaagat | aagatggcgg | aggcctacag | tgagattggg | atgaaaggcg | agcgccggag | 1800 |
| gggcaagggg | cacgatggcc | tttaccaggg | tctcagtaca | gccaccaagg | acacctacga | 1860 |
| cgcccttcac | atgcaggccc | tgccccctcg | ctaggtcgac | ctcgagggaa | ttccgataat | 1920 |
| caacctctgg | attacaaaat | ttgtgaaaga | ttgactggta | ttcttaacta | tgttgctcct | 1980 |
| tttacgcta | | | | | 1989 |

<210> SEQ ID NO 40
<211> LENGTH: 2115
<212> TYPE: DNA
<213> ORGANISM: Artificial sequence
<220> FEATURE:
<221> NAME/KEY: misc_feature
<223> OTHER INFORMATION: P3F2-28BBZ polynucleotide

<400> SEQUENCE: 40

| | | | | | |
|---|---|---|---|---|---|
| gcaggggaaa | gaatagtaga | cataatagca | acagacatac | aaactaaaga | attacaaaaa   60 |
| caaattacaa | aaattcaaaa | ttttccgatc | acgagactag | cctcgagaag | cttgatcgat  120 |
| ggctccggtg | cccgtcagtg | ggcagagcgc | acatcgccca | cagtcccga  | gaagttgggg  180 |
| ggaggggtcg | gcaattgaac | cggtgcctag | agaaggtggc | gcggggtaaa | ctgggaaagt  240 |
| gatgtcgtgt | actggctccg | cctttttccc | gaggtgggg  | gagaaccgta | tataagtgca  300 |
| gtagtcgccg | tgaacgttct | ttttcgcaac | gggtttgccg | ccagaacaca | ggtgtcgtga  360 |
| cgcggatcca | ggcctaagct | tacgcgtcct | agcgctaccg | gtcgccacca | tggccttacc  420 |
| agtgaccgcc | ttgctcctgc | cgctggcctt | gctgctccac | gccgccaggc | cgcagatgca  480 |
| gctagtgcag | tctggggctg | aggtgaagaa | gcctggggcc | tcagtgaagg | tttcctgcaa  540 |
| ggcatctgga | tacaccttca | ccagctacta | tatgcactgg | gtgcgacagg | cccctggaca  600 |
| agggcttgag | tggatgggaa | taatcaaccc | tagtggtggt | agcacaagct | acgcacagaa  660 |
| gttccagggc | agagtcacca | tgaccaggga | cacgtccacg | agcacagtct | acatggagct  720 |
| gagcagcctg | agatctgagg | acacggccgt | gtattactgt | gcgagtagtc | ggagtgggac  780 |
| tacggtggta | aatcatgatg | cttttgatat | ctgggggaaa | gggaccacgg | tcaccgtctc  840 |
| gagtggtgga | ggcggttcag | gcggaggtgg | ttctggcggt | ggcggatcgg | acatccagtt  900 |
| gacccagtct | ccatcctccc | tgtctgcgtc | tgtaggagac | agagtcacca | tcacttgccg  960 |
| ggcaagccag | gtcattagcc | gtgctttagc | ctggtatcaa | caaacaccag | ggaaacctcc 1020 |
| taaactcctg | atctatgatg | cctccaattt | gcagagtggg | gtcccatcaa | ggttcagcgg 1080 |
| cagtggatct | gggacagatt | tcactctcac | catcagccgc | ctgcagcctg | aagattttgc 1140 |
| aacttattac | tgtcaacagt | ttaatagtta | ccctctcact | ttcggcggag | ggaccaagct 1200 |
| ggagatcaaa | cgtaccacga | cgccagcgcc | gcgaccacca | acaccggcgc | ccaccatcgc 1260 |
| gtcgcagccc | ctgtccctgc | gcccagaggc | gtgccggcca | gcggcggggg | gcgcagtgca 1320 |
| cacgaggggg | ctggacttcg | cctgtgattt | ttgggtgctg | gtggtggttg | gtggagtcct 1380 |
| ggcttgctat | agcttgctag | taacagtggc | ctttattatt | ttctgggtga | ggagtaagag 1440 |
| gagcaggctc | ctgcacagtg | actacatgaa | catgactccc | cgccgccccg | gccaacccg  1500 |
| caagcattac | cagccctatg | ccccaccacg | cgacttcgca | gcctatcgct | ccaaacgggg 1560 |
| cagaaagaaa | ctcctgtata | tattcaaaca | accatttatg | agaccagtac | aaactactca 1620 |
| agaggaagat | ggctgtagct | gccgatttcc | agaagaagaa | gaaggaggat | gtgaactgag 1680 |
| agtgaagttc | agcaggagcg | cagacgcccc | cgcgtaccag | cagggccaga | accagctcta 1740 |
| taacgagctc | aatctaggac | gaagagagga | gtacgatgtt | ttggacaaga | gacgtggccg 1800 |
| ggaccctgag | atggggggaa | agccgcagag | aaggaagaac | cctcaggaag | gcctgtacaa 1860 |
| tgaactgcag | aaagataaga | tggcggaggc | ctacagtgag | attgggatga | aggcgagcg  1920 |
| ccggaggggc | aaggggcacg | atggccttta | ccagggtctc | agtacagcca | ccaaggacac 1980 |
| ctacgacgcc | cttcacatgc | aggccctgcc | ccctcgctag | gtcgacctcg | agggaattcc 2040 |

```
gataatcaac ctctggatta caaaatttgt gaaagattga ctggtattct taactatgtt    2100 gctccttta cgcta                                                      2115
```

<210> SEQ ID NO 41
<211> LENGTH: 353
<212> TYPE: PRT
<213> ORGANISM: Artificial sequence
<220> FEATURE:
<221> NAME/KEY: MISC_FEATURE
<223> OTHER INFORMATION: P1A6E-delta Z amino acid sequence

<400> SEQUENCE: 41

```
Met Ala Leu Pro Val Thr Ala Leu Leu Pro Leu Ala Leu Leu Leu
1               5                   10                  15

His Ala Ala Arg Pro Gln Val Gln Leu Glu Gln Ser Gly Leu Gly Leu
            20                  25                  30

Val Lys Pro Ser Gln Thr Leu Ser Leu Thr Cys Ala Ile Ser Gly Asp
        35                  40                  45

Thr Val Ser Ser Asp Ser Ala Ala Trp Asn Trp Ile Arg Gln Ser Pro
    50                  55                  60

Ser Arg Gly Leu Glu Trp Leu Gly Arg Thr Tyr Tyr Arg Ser Lys Trp
65                  70                  75                  80

Phe Asn Asp Tyr Ala Val Ser Val Lys Gly Arg Ile Thr Ile Asn Ser
                85                  90                  95

Asp Thr Ser Lys Asn Gln Phe Ser Leu Gln Leu Asn Ser Val Thr Pro
            100                 105                 110

Glu Asp Thr Ala Val Tyr Tyr Cys Ala Arg Ser Asn Ser Tyr Tyr Tyr
        115                 120                 125

Tyr Ala Met Asp Val Trp Gly Gln Gly Thr Leu Val Thr Val Ser Ser
    130                 135                 140

Gly Gly Gly Gly Ser Gly Gly Gly Ser Gly Gly Gly Ser Gln
145                 150                 155                 160

Ala Val Leu Thr Gln Pro Ser Ser Leu Ser Ala Ser Pro Gly Ala Ser
                165                 170                 175

Ala Ser Leu Thr Cys Thr Leu Arg Ser Gly Ile Asn Val Gly Ile Tyr
            180                 185                 190

Arg Ile Tyr Trp Tyr Gln Gln Arg Pro Gly Ser Pro Pro Gln Ile Leu
        195                 200                 205

Leu Thr Tyr Lys Ser Asp Ser Asp Lys Tyr Gln Gly Ser Gly Val Pro
    210                 215                 220

Ser Arg Phe Ser Gly Ser Lys Asp Ala Ser Ala Asn Ala Gly Ile Leu
225                 230                 235                 240

Leu Ile Ser Gly Leu Gln Ser Glu Asp Glu Ala Asp Tyr Tyr Cys Met
                245                 250                 255

Ile Trp His Ser Gly Gly Trp Val Phe Gly Gly Gly Thr Lys Val Thr
            260                 265                 270

Val Leu Gly Thr Thr Thr Pro Ala Pro Arg Pro Pro Thr Pro Ala Pro
        275                 280                 285

Thr Ile Ala Ser Gln Pro Leu Ser Leu Arg Pro Glu Ala Cys Arg Pro
    290                 295                 300

Ala Ala Gly Gly Ala Val His Thr Arg Gly Leu Asp Phe Ala Cys Asp
305                 310                 315                 320

Ile Tyr Ile Trp Ala Pro Leu Ala Gly Thr Cys Gly Val Leu Leu Leu
                325                 330                 335

Ser Leu Val Ile Thr Arg Val Lys Phe Ser Arg Ser Ala Asp Ala Pro
```

Ala

<210> SEQ ID NO 42
<211> LENGTH: 454
<212> TYPE: PRT
<213> ORGANISM: Artificial sequence
<220> FEATURE:
<221> NAME/KEY: MISC_FEATURE
<223> OTHER INFORMATION: P1A6E-Z amino acid sequence

<400> SEQUENCE: 42

```
Met Ala Leu Pro Val Thr Ala Leu Leu Pro Leu Ala Leu Leu Leu
1               5                   10                  15

His Ala Ala Arg Pro Gln Val Gln Leu Glu Gln Ser Gly Leu Gly Leu
            20                  25                  30

Val Lys Pro Ser Gln Thr Leu Ser Leu Thr Cys Ala Ile Ser Gly Asp
        35                  40                  45

Thr Val Ser Ser Asp Ser Ala Ala Trp Asn Trp Ile Arg Gln Ser Pro
    50                  55                  60

Ser Arg Gly Leu Glu Trp Leu Gly Arg Thr Tyr Tyr Arg Ser Lys Trp
65                  70                  75                  80

Phe Asn Asp Tyr Ala Val Ser Val Lys Gly Arg Ile Thr Ile Asn Ser
                85                  90                  95

Asp Thr Ser Lys Asn Gln Phe Ser Leu Gln Leu Asn Ser Val Thr Pro
            100                 105                 110

Glu Asp Thr Ala Val Tyr Tyr Cys Ala Arg Ser Asn Ser Tyr Tyr Tyr
        115                 120                 125

Tyr Ala Met Asp Val Trp Gly Gln Gly Thr Leu Val Thr Val Ser Ser
    130                 135                 140

Gly Gly Gly Gly Ser Gly Gly Gly Ser Gly Gly Gly Gly Ser Gln
145                 150                 155                 160

Ala Val Leu Thr Gln Pro Ser Ser Leu Ser Ala Ser Pro Gly Ala Ser
                165                 170                 175

Ala Ser Leu Thr Cys Thr Leu Arg Ser Gly Ile Asn Val Gly Ile Tyr
            180                 185                 190

Arg Ile Tyr Trp Tyr Gln Gln Arg Pro Gly Ser Pro Pro Gln Ile Leu
        195                 200                 205

Leu Thr Tyr Lys Ser Asp Ser Asp Lys Tyr Gln Gly Ser Gly Val Pro
    210                 215                 220

Ser Arg Phe Ser Gly Ser Lys Asp Ala Ser Ala Asn Ala Gly Ile Leu
225                 230                 235                 240

Leu Ile Ser Gly Leu Gln Ser Glu Asp Glu Ala Asp Tyr Tyr Cys Met
                245                 250                 255

Ile Trp His Ser Gly Gly Trp Val Phe Gly Gly Gly Thr Lys Val Thr
            260                 265                 270

Val Leu Gly Thr Thr Thr Pro Ala Pro Arg Pro Pro Thr Pro Ala Pro
        275                 280                 285

Thr Ile Ala Ser Gln Pro Leu Ser Leu Arg Pro Glu Ala Cys Arg Pro
    290                 295                 300

Ala Ala Gly Gly Ala Val His Thr Arg Gly Leu Asp Phe Ala Cys Asp
305                 310                 315                 320

Ile Tyr Ile Trp Ala Pro Leu Ala Gly Thr Cys Gly Val Leu Leu Leu
                325                 330                 335

Ser Leu Val Ile Thr Arg Val Lys Phe Ser Arg Ser Ala Asp Ala Pro
```

```
                    340                 345                 350
Ala Tyr Gln Gln Gly Gln Asn Gln Leu Tyr Asn Glu Leu Asn Leu Gly
                355                 360                 365

Arg Arg Glu Glu Tyr Asp Val Leu Asp Lys Arg Arg Gly Arg Asp Pro
            370                 375                 380

Glu Met Gly Gly Lys Pro Gln Arg Arg Lys Asn Pro Gln Glu Gly Leu
385                 390                 395                 400

Tyr Asn Glu Leu Gln Lys Asp Lys Met Ala Glu Ala Tyr Ser Glu Ile
                405                 410                 415

Gly Met Lys Gly Glu Arg Arg Arg Gly Lys Gly His Asp Gly Leu Tyr
            420                 425                 430

Gln Gly Leu Ser Thr Ala Thr Lys Asp Thr Tyr Asp Ala Leu His Met
        435                 440                 445

Gln Ala Leu Pro Pro Arg
    450

<210> SEQ ID NO 43
<211> LENGTH: 498
<212> TYPE: PRT
<213> ORGANISM: Artificial sequence
<220> FEATURE:
<221> NAME/KEY: MISC_FEATURE
<223> OTHER INFORMATION: P1A6E-BBZ amino acid sequence

<400> SEQUENCE: 43

Met Ala Leu Pro Val Thr Ala Leu Leu Leu Pro Leu Ala Leu Leu Leu
1               5                   10                  15

His Ala Ala Arg Pro Gln Val Gln Leu Glu Gln Ser Gly Leu Gly Leu
            20                  25                  30

Val Lys Pro Ser Gln Thr Leu Ser Leu Thr Cys Ala Ile Ser Gly Asp
        35                  40                  45

Thr Val Ser Ser Asp Ser Ala Ala Trp Asn Trp Ile Arg Gln Ser Pro
    50                  55                  60

Ser Arg Gly Leu Glu Trp Leu Gly Arg Thr Tyr Tyr Arg Ser Lys Trp
65                  70                  75                  80

Phe Asn Asp Tyr Ala Val Ser Val Lys Gly Arg Ile Thr Ile Asn Ser
                85                  90                  95

Asp Thr Ser Lys Asn Gln Phe Ser Leu Gln Leu Asn Ser Val Thr Pro
            100                 105                 110

Glu Asp Thr Ala Val Tyr Tyr Cys Ala Arg Ser Asn Ser Tyr Tyr Tyr
        115                 120                 125

Tyr Ala Met Asp Val Trp Gly Gln Gly Thr Leu Val Thr Val Ser Ser
    130                 135                 140

Gly Gly Gly Gly Ser Gly Gly Gly Gly Ser Gly Gly Gly Gly Ser Gln
145                 150                 155                 160

Ala Val Leu Thr Gln Pro Ser Ser Leu Ser Ala Ser Pro Gly Ala Ser
                165                 170                 175

Ala Ser Leu Thr Cys Thr Leu Arg Ser Gly Ile Asn Val Gly Ile Tyr
            180                 185                 190

Arg Ile Tyr Trp Tyr Gln Gln Arg Pro Gly Ser Pro Gln Ile Leu
        195                 200                 205

Leu Thr Tyr Lys Ser Asp Ser Asp Lys Tyr Gln Gly Ser Gly Val Pro
    210                 215                 220

Ser Arg Phe Ser Gly Ser Lys Asp Ala Ser Ala Asn Ala Gly Ile Leu
225                 230                 235                 240
```

```
Leu Ile Ser Gly Leu Gln Ser Glu Asp Glu Ala Asp Tyr Tyr Cys Met
                245                 250                 255

Ile Trp His Ser Gly Gly Trp Val Phe Gly Gly Gly Thr Lys Val Thr
            260                 265                 270

Val Leu Gly Thr Thr Thr Pro Ala Pro Arg Pro Pro Thr Pro Ala Pro
        275                 280                 285

Thr Ile Ala Ser Gln Pro Leu Ser Leu Arg Pro Glu Ala Cys Arg Pro
    290                 295                 300

Ala Ala Gly Gly Ala Val His Thr Arg Gly Leu Asp Phe Ala Cys Asp
305                 310                 315                 320

Ile Tyr Ile Trp Ala Pro Leu Ala Gly Thr Cys Gly Val Leu Leu Leu
                325                 330                 335

Ser Leu Val Ile Thr Leu Tyr Cys Lys Arg Gly Arg Lys Lys Leu Leu
            340                 345                 350

Tyr Ile Phe Lys Gln Pro Phe Met Arg Pro Val Gln Thr Thr Gln Glu
        355                 360                 365

Glu Asp Gly Cys Ser Cys Arg Phe Pro Glu Glu Glu Glu Gly Gly Cys
    370                 375                 380

Glu Leu Arg Val Lys Phe Ser Arg Ser Ala Asp Ala Pro Ala Tyr Lys
385                 390                 395                 400

Gln Gly Gln Asn Gln Leu Tyr Asn Glu Leu Asn Leu Gly Arg Arg Glu
                405                 410                 415

Glu Tyr Asp Val Leu Asp Lys Arg Arg Gly Arg Asp Pro Glu Met Gly
            420                 425                 430

Gly Lys Pro Arg Arg Lys Asn Pro Gln Glu Gly Leu Tyr Asn Glu Leu
        435                 440                 445

Gln Lys Asp Lys Met Ala Glu Ala Tyr Ser Glu Ile Gly Met Lys Gly
    450                 455                 460

Glu Arg Arg Arg Gly Lys Gly His Asp Gly Leu Tyr Gln Gly Leu Ser
465                 470                 475                 480

Thr Ala Thr Lys Asp Thr Tyr Asp Ala Leu His Met Gln Ala Leu Pro
                485                 490                 495

Pro Arg

<210> SEQ ID NO 44
<211> LENGTH: 501
<212> TYPE: PRT
<213> ORGANISM: Artificial sequence
<220> FEATURE:
<221> NAME/KEY: MISC_FEATURE
<223> OTHER INFORMATION: P1A6E-28Z amino acid sequence

<400> SEQUENCE: 44

Met Ala Leu Pro Val Thr Ala Leu Leu Leu Pro Leu Ala Leu Leu Leu
1               5                   10                  15

His Ala Ala Arg Pro Gln Val Gln Leu Glu Gln Ser Gly Leu Gly Leu
            20                  25                  30

Val Lys Pro Ser Gln Thr Leu Ser Leu Thr Cys Ala Ile Ser Gly Asp
        35                  40                  45

Thr Val Ser Ser Asp Ser Ala Ala Trp Asn Trp Ile Arg Gln Ser Pro
    50                  55                  60

Ser Arg Gly Leu Glu Trp Leu Gly Arg Thr Tyr Tyr Arg Ser Lys Trp
65                  70                  75                  80

Phe Asn Asp Tyr Ala Val Ser Val Lys Gly Arg Ile Thr Ile Asn Ser
                85                  90                  95
```

```
Asp Thr Ser Lys Asn Gln Phe Ser Leu Gln Leu Asn Ser Val Thr Pro
                100                 105                 110

Glu Asp Thr Ala Val Tyr Tyr Cys Ala Arg Ser Asn Ser Tyr Tyr Tyr
            115                 120                 125

Tyr Ala Met Asp Val Trp Gly Gln Gly Thr Leu Val Thr Val Ser Ser
        130                 135                 140

Gly Gly Gly Gly Ser Gly Gly Gly Ser Gly Gly Gly Gly Ser Gln
145                 150                 155                 160

Ala Val Leu Thr Gln Pro Ser Ser Leu Ser Ala Ser Pro Gly Ala Ser
                165                 170                 175

Ala Ser Leu Thr Cys Thr Leu Arg Ser Gly Ile Asn Val Gly Ile Tyr
                180                 185                 190

Arg Ile Tyr Trp Tyr Gln Gln Arg Pro Gly Ser Pro Pro Gln Ile Leu
            195                 200                 205

Leu Thr Tyr Lys Ser Asp Ser Asp Lys Tyr Gln Gly Ser Gly Val Pro
        210                 215                 220

Ser Arg Phe Ser Gly Ser Lys Asp Ala Ser Ala Asn Ala Gly Ile Leu
225                 230                 235                 240

Leu Ile Ser Gly Leu Gln Ser Glu Asp Glu Ala Asp Tyr Tyr Cys Met
                245                 250                 255

Ile Trp His Ser Gly Gly Trp Val Phe Gly Gly Gly Thr Lys Val Thr
                260                 265                 270

Val Leu Gly Thr Thr Thr Pro Ala Pro Arg Pro Pro Thr Pro Ala Pro
            275                 280                 285

Thr Ile Ala Ser Gln Pro Leu Ser Leu Arg Pro Glu Ala Cys Arg Pro
        290                 295                 300

Ala Ala Gly Gly Ala Val His Thr Arg Gly Leu Asp Phe Ala Cys Asp
305                 310                 315                 320

Phe Trp Val Leu Val Val Val Gly Gly Val Leu Ala Cys Tyr Ser Leu
                325                 330                 335

Leu Val Thr Val Ala Phe Ile Ile Phe Trp Val Arg Ser Lys Arg Ser
            340                 345                 350

Arg Leu Leu His Ser Asp Tyr Met Asn Met Thr Pro Arg Arg Pro Gly
        355                 360                 365

Pro Thr Arg Lys His Tyr Gln Pro Tyr Ala Pro Pro Arg Asp Phe Ala
370                 375                 380

Ala Tyr Arg Ser Arg Val Lys Phe Ser Arg Ser Ala Asp Ala Pro Ala
385                 390                 395                 400

Tyr Gln Gln Gly Gln Asn Gln Leu Tyr Asn Glu Leu Asn Leu Gly Arg
                405                 410                 415

Arg Glu Glu Tyr Asp Val Leu Asp Lys Arg Arg Gly Arg Asp Pro Glu
            420                 425                 430

Met Gly Gly Lys Pro Gln Arg Arg Lys Asn Pro Gln Glu Gly Leu Tyr
        435                 440                 445

Asn Glu Leu Gln Lys Asp Lys Met Ala Glu Ala Tyr Ser Glu Ile Gly
450                 455                 460

Met Lys Gly Glu Arg Arg Arg Gly Lys Gly His Asp Gly Leu Tyr Gln
465                 470                 475                 480

Gly Leu Ser Thr Ala Thr Lys Asp Thr Tyr Asp Ala Leu His Met Gln
                485                 490                 495

Ala Leu Pro Pro Arg
                500
```

<210> SEQ ID NO 45
<211> LENGTH: 543
<212> TYPE: PRT
<213> ORGANISM: Artificial sequence
<220> FEATURE:
<221> NAME/KEY: MISC_FEATURE
<223> OTHER INFORMATION: P1A6E-28BBZ amino acid sequence

<400> SEQUENCE: 45

```
Met Ala Leu Pro Val Thr Ala Leu Leu Leu Pro Leu Ala Leu Leu Leu
1               5                   10                  15

His Ala Ala Arg Pro Gln Val Gln Leu Glu Gln Ser Gly Leu Gly Leu
            20                  25                  30

Val Lys Pro Ser Gln Thr Leu Ser Leu Thr Cys Ala Ile Ser Gly Asp
        35                  40                  45

Thr Val Ser Ser Asp Ser Ala Ala Trp Asn Trp Ile Arg Gln Ser Pro
    50                  55                  60

Ser Arg Gly Leu Glu Trp Leu Gly Arg Thr Tyr Tyr Arg Ser Lys Trp
65                  70                  75                  80

Phe Asn Asp Tyr Ala Val Ser Val Lys Gly Arg Ile Thr Ile Asn Ser
                85                  90                  95

Asp Thr Ser Lys Asn Gln Phe Ser Leu Gln Leu Asn Ser Val Thr Pro
            100                 105                 110

Glu Asp Thr Ala Val Tyr Tyr Cys Ala Arg Ser Asn Ser Tyr Tyr Tyr
        115                 120                 125

Tyr Ala Met Asp Val Trp Gly Gln Gly Thr Leu Val Thr Val Ser Ser
    130                 135                 140

Gly Gly Gly Gly Ser Gly Gly Gly Ser Gly Gly Gly Gly Ser Gln
145                 150                 155                 160

Ala Val Leu Thr Gln Pro Ser Ser Leu Ser Ala Ser Pro Gly Ala Ser
                165                 170                 175

Ala Ser Leu Thr Cys Thr Leu Arg Ser Gly Ile Asn Val Gly Ile Tyr
            180                 185                 190

Arg Ile Tyr Trp Tyr Gln Gln Arg Pro Gly Ser Pro Pro Gln Ile Leu
        195                 200                 205

Leu Thr Tyr Lys Ser Asp Ser Asp Lys Tyr Gln Gly Ser Gly Val Pro
    210                 215                 220

Ser Arg Phe Ser Gly Ser Lys Asp Ala Ser Ala Asn Ala Gly Ile Leu
225                 230                 235                 240

Leu Ile Ser Gly Leu Gln Ser Glu Asp Glu Ala Asp Tyr Tyr Cys Met
                245                 250                 255

Ile Trp His Ser Gly Gly Trp Val Phe Gly Gly Gly Thr Lys Val Thr
            260                 265                 270

Val Leu Gly Thr Thr Thr Pro Ala Pro Arg Pro Pro Thr Pro Ala Pro
        275                 280                 285

Thr Ile Ala Ser Gln Pro Leu Ser Leu Arg Pro Glu Ala Cys Arg Pro
    290                 295                 300

Ala Ala Gly Gly Ala Val His Thr Arg Gly Leu Asp Phe Ala Cys Asp
305                 310                 315                 320

Phe Trp Val Leu Val Val Val Gly Gly Val Leu Ala Cys Tyr Ser Leu
                325                 330                 335

Leu Val Thr Val Ala Phe Ile Ile Phe Trp Val Arg Ser Lys Arg Ser
            340                 345                 350

Arg Leu Leu His Ser Asp Tyr Met Asn Met Thr Pro Arg Arg Pro Gly
        355                 360                 365
```

Pro Thr Arg Lys His Tyr Gln Pro Tyr Ala Pro Pro Arg Asp Phe Ala
370                 375                 380

Ala Tyr Arg Ser Lys Arg Gly Arg Lys Leu Leu Tyr Ile Phe Lys
385                 390                 395                 400

Gln Pro Phe Met Arg Pro Val Gln Thr Thr Gln Glu Glu Asp Gly Cys
                405                 410                 415

Ser Cys Arg Phe Pro Glu Glu Glu Gly Gly Cys Glu Leu Arg Val
            420                 425                 430

Lys Phe Ser Arg Ser Ala Asp Ala Pro Ala Tyr Gln Gln Gly Gln Asn
        435                 440                 445

Gln Leu Tyr Asn Glu Leu Asn Leu Gly Arg Arg Glu Glu Tyr Asp Val
450                 455                 460

Leu Asp Lys Arg Arg Gly Arg Asp Pro Glu Met Gly Gly Lys Pro Gln
465                 470                 475                 480

Arg Arg Lys Asn Pro Gln Glu Gly Leu Tyr Asn Glu Leu Gln Lys Asp
                485                 490                 495

Lys Met Ala Glu Ala Tyr Ser Glu Ile Gly Met Lys Gly Glu Arg Arg
            500                 505                 510

Arg Gly Lys Gly His Asp Gly Leu Tyr Gln Gly Leu Ser Thr Ala Thr
        515                 520                 525

Lys Asp Thr Tyr Asp Ala Leu His Met Gln Ala Leu Pro Pro Arg
530                 535                 540

<210> SEQ ID NO 46
<211> LENGTH: 346
<212> TYPE: PRT
<213> ORGANISM: Artificial sequence
<220> FEATURE:
<221> NAME/KEY: MISC_FEATURE
<223> OTHER INFORMATION: P3F2-delta Z amino acid sequence

<400> SEQUENCE: 46

Met Ala Leu Pro Val Thr Ala Leu Leu Leu Pro Leu Ala Leu Leu Leu
1               5                   10                  15

His Ala Ala Arg Pro Gln Met Gln Leu Val Gln Ser Gly Ala Glu Val
            20                  25                  30

Lys Lys Pro Gly Ala Ser Val Lys Val Ser Cys Lys Ala Ser Gly Tyr
        35                  40                  45

Thr Phe Thr Ser Tyr Tyr Met His Trp Val Arg Gln Ala Pro Gly Gln
    50                  55                  60

Gly Leu Glu Trp Met Gly Ile Ile Asn Pro Ser Gly Gly Ser Thr Ser
65                  70                  75                  80

Tyr Ala Gln Lys Phe Gln Gly Arg Val Thr Met Thr Arg Asp Thr Ser
                85                  90                  95

Thr Ser Thr Val Tyr Met Glu Leu Ser Ser Leu Arg Ser Glu Asp Thr
            100                 105                 110

Ala Val Tyr Tyr Cys Ala Ser Ser Arg Ser Gly Thr Thr Val Val Asn
        115                 120                 125

His Asp Ala Phe Asp Ile Trp Gly Lys Gly Thr Thr Val Thr Val Ser
    130                 135                 140

Ser Gly Gly Gly Gly Ser Gly Gly Gly Ser Gly Gly Gly Gly Ser
145                 150                 155                 160

Asp Ile Gln Leu Thr Gln Ser Pro Ser Ser Leu Ser Ala Ser Val Gly
                165                 170                 175

Asp Arg Val Thr Ile Thr Cys Arg Ala Ser Gln Val Ile Ser Arg Ala
            180                 185                 190

Leu Ala Trp Tyr Gln Gln Thr Pro Gly Lys Pro Pro Lys Leu Leu Ile
            195                 200                 205

Tyr Asp Ala Ser Asn Leu Gln Ser Gly Val Pro Ser Arg Phe Ser Gly
        210                 215                 220

Ser Gly Ser Gly Thr Asp Phe Thr Leu Thr Ile Ser Arg Leu Gln Pro
225                 230                 235                 240

Glu Asp Phe Ala Thr Tyr Tyr Cys Gln Gln Phe Asn Ser Tyr Pro Leu
                245                 250                 255

Thr Phe Gly Gly Gly Thr Lys Leu Glu Ile Lys Arg Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Arg Val
                325                 330                 335

Lys Phe Ser Arg Ser Ala Asp Ala Pro Ala
            340                 345

<210> SEQ ID NO 47
<211> LENGTH: 447
<212> TYPE: PRT
<213> ORGANISM: Artificial sequence
<220> FEATURE:
<221> NAME/KEY: MISC_FEATURE
<223> OTHER INFORMATION: P3F2-Z amino acid sequence

<400> SEQUENCE: 47

Met Ala Leu Pro Val Thr Ala Leu Leu Leu Pro Leu Ala Leu Leu Leu
1               5                   10                  15

His Ala Ala Arg Pro Gln Met Gln Leu Val Gln Ser Gly Ala Glu Val
            20                  25                  30

Lys Lys Pro Gly Ala Ser Val Lys Val Ser Cys Lys Ala Ser Gly Tyr
        35                  40                  45

Thr Phe Thr Ser Tyr Tyr Met His Trp Val Arg Gln Ala Pro Gly Gln
    50                  55                  60

Gly Leu Glu Trp Met Gly Ile Ile Asn Pro Ser Gly Gly Ser Thr Ser
65                  70                  75                  80

Tyr Ala Gln Lys Phe Gln Gly Arg Val Thr Met Thr Arg Asp Thr Ser
                85                  90                  95

Thr Ser Thr Val Tyr Met Glu Leu Ser Ser Leu Arg Ser Glu Asp Thr
            100                 105                 110

Ala Val Tyr Tyr Cys Ala Ser Ser Arg Ser Gly Thr Thr Val Val Asn
        115                 120                 125

His Asp Ala Phe Asp Ile Trp Gly Lys Gly Thr Thr Val Thr Val Ser
    130                 135                 140

Ser Gly Gly Gly Gly Ser Gly Gly Gly Gly Ser Gly Gly Gly Gly Ser
145                 150                 155                 160

Asp Ile Gln Leu Thr Gln Ser Pro Ser Ser Leu Ser Ala Ser Val Gly
                165                 170                 175

Asp Arg Val Thr Ile Thr Cys Arg Ala Ser Gln Val Ile Ser Arg Ala
            180                 185                 190

Leu Ala Trp Tyr Gln Gln Thr Pro Gly Lys Pro Pro Lys Leu Leu Ile

```
            195                 200                 205
Tyr Asp Ala Ser Asn Leu Gln Ser Gly Val Pro Ser Arg Phe Ser Gly
        210                 215                 220

Ser Gly Ser Gly Thr Asp Phe Thr Leu Thr Ile Ser Arg Leu Gln Pro
225                 230                 235                 240

Glu Asp Phe Ala Thr Tyr Tyr Cys Gln Gln Phe Asn Ser Tyr Pro Leu
                245                 250                 255

Thr Phe Gly Gly Gly Thr Lys Leu Glu Ile Lys Arg Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Arg Val
                325                 330                 335

Lys Phe Ser Arg Ser Ala Asp Ala Pro Ala Tyr Gln Gln Gly Gln Asn
            340                 345                 350

Gln Leu Tyr Asn Glu Leu Asn Leu Gly Arg Arg Glu Glu Tyr Asp Val
        355                 360                 365

Leu Asp Lys Arg Arg Gly Arg Asp Pro Glu Met Gly Gly Lys Pro Gln
370                 375                 380

Arg Arg Lys Asn Pro Gln Glu Gly Leu Tyr Asn Glu Leu Gln Lys Asp
385                 390                 395                 400

Lys Met Ala Glu Ala Tyr Ser Glu Ile Gly Met Lys Gly Glu Arg Arg
                405                 410                 415

Arg Gly Lys Gly His Asp Gly Leu Tyr Gln Gly Leu Ser Thr Ala Thr
            420                 425                 430

Lys Asp Thr Tyr Asp Ala Leu His Met Gln Ala Leu Pro Pro Arg
        435                 440                 445

<210> SEQ ID NO 48
<211> LENGTH: 491
<212> TYPE: PRT
<213> ORGANISM: Artificial sequence
<220> FEATURE:
<221> NAME/KEY: MISC_FEATURE
<223> OTHER INFORMATION: P3F2-BBZ amino acid sequence

<400> SEQUENCE: 48

Met Ala Leu Pro Val Thr Ala Leu Leu Leu Pro Leu Ala Leu Leu Leu
1               5                   10                  15

His Ala Ala Arg Pro Gln Met Gln Leu Val Gln Ser Gly Ala Glu Val
            20                  25                  30

Lys Lys Pro Gly Ala Ser Val Lys Val Ser Cys Lys Ala Ser Gly Tyr
        35                  40                  45

Thr Phe Thr Ser Tyr Tyr Met His Trp Val Arg Gln Ala Pro Gly Gln
    50                  55                  60

Gly Leu Glu Trp Met Gly Ile Ile Asn Pro Ser Gly Gly Ser Thr Ser
65                  70                  75                  80

Tyr Ala Gln Lys Phe Gln Gly Arg Val Thr Met Thr Arg Asp Thr Ser
                85                  90                  95

Thr Ser Thr Val Tyr Met Glu Leu Ser Ser Leu Arg Ser Glu Asp Thr
            100                 105                 110
```

Ala Val Tyr Tyr Cys Ala Ser Ser Arg Ser Gly Thr Thr Val Val Asn
            115                 120                 125

His Asp Ala Phe Asp Ile Trp Gly Lys Gly Thr Thr Val Thr Val Ser
130                 135                 140

Ser Gly Gly Gly Ser Gly Gly Gly Ser Gly Gly Gly Gly Ser
145                 150                 155                 160

Asp Ile Gln Leu Thr Gln Ser Pro Ser Ser Leu Ser Ala Ser Val Gly
                165                 170                 175

Asp Arg Val Thr Ile Thr Cys Arg Ala Ser Gln Val Ile Ser Arg Ala
            180                 185                 190

Leu Ala Trp Tyr Gln Gln Thr Pro Gly Lys Pro Lys Leu Leu Ile
        195                 200                 205

Tyr Asp Ala Ser Asn Leu Gln Ser Gly Val Pro Ser Arg Phe Ser Gly
210                 215                 220

Ser Gly Ser Gly Thr Asp Phe Thr Leu Thr Ile Ser Arg Leu Gln Pro
225                 230                 235                 240

Glu Asp Phe Ala Thr Tyr Tyr Cys Gln Gln Phe Asn Ser Tyr Pro Leu
                245                 250                 255

Thr Phe Gly Gly Gly Thr Lys Leu Glu Ile Lys Arg Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
370                 375                 380

Arg Ser Ala Asp Ala Pro Ala Tyr Lys Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490

<210> SEQ ID NO 49
<211> LENGTH: 494
<212> TYPE: PRT
<213> ORGANISM: Artificial sequence
<220> FEATURE:
<221> NAME/KEY: MISC_FEATURE
<223> OTHER INFORMATION: P3F2-28Z amino acid sequence

<400> SEQUENCE: 49

```
Met Ala Leu Pro Val Thr Ala Leu Leu Leu Pro Leu Ala Leu Leu Leu
1               5                   10                  15

His Ala Ala Arg Pro Gln Met Gln Leu Val Gln Ser Gly Ala Glu Val
            20                  25                  30

Lys Lys Pro Gly Ala Ser Val Lys Val Ser Cys Lys Ala Ser Gly Tyr
        35                  40                  45

Thr Phe Thr Ser Tyr Tyr Met His Trp Val Arg Gln Ala Pro Gly Gln
    50                  55                  60

Gly Leu Glu Trp Met Gly Ile Ile Asn Pro Ser Gly Gly Ser Thr Ser
65                  70                  75                  80

Tyr Ala Gln Lys Phe Gln Gly Arg Val Thr Met Thr Arg Asp Thr Ser
                85                  90                  95

Thr Ser Thr Val Tyr Met Glu Leu Ser Ser Leu Arg Ser Glu Asp Thr
            100                 105                 110

Ala Val Tyr Tyr Cys Ala Ser Ser Arg Ser Gly Thr Thr Val Val Asn
        115                 120                 125

His Asp Ala Phe Asp Ile Trp Gly Lys Gly Thr Thr Val Thr Val Ser
    130                 135                 140

Ser Gly Gly Gly Gly Ser Gly Gly Gly Gly Ser Gly Gly Gly Gly Ser
145                 150                 155                 160

Asp Ile Gln Leu Thr Gln Ser Pro Ser Ser Leu Ser Ala Ser Val Gly
                165                 170                 175

Asp Arg Val Thr Ile Thr Cys Arg Ala Ser Gln Val Ile Ser Arg Ala
            180                 185                 190

Leu Ala Trp Tyr Gln Gln Thr Pro Gly Lys Pro Pro Lys Leu Leu Ile
        195                 200                 205

Tyr Asp Ala Ser Asn Leu Gln Ser Gly Val Pro Ser Arg Phe Ser Gly
    210                 215                 220

Ser Gly Ser Gly Thr Asp Phe Thr Leu Thr Ile Ser Arg Leu Gln Pro
225                 230                 235                 240

Glu Asp Phe Ala Thr Tyr Tyr Cys Gln Gln Phe Asn Ser Tyr Pro Leu
                245                 250                 255

Thr Phe Gly Gly Gly Thr Lys Leu Glu Ile Lys Arg Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Phe Trp Val Leu Val Val Val
305                 310                 315                 320

Gly Gly Val Leu Ala Cys Tyr Ser Leu Leu Val Thr Val Ala Phe Ile
                325                 330                 335

Ile Phe Trp Val Arg Ser Lys Arg Ser Arg Leu Leu His Ser Asp Tyr
            340                 345                 350

Met Asn Met Thr Pro Arg Arg Pro Gly Pro Thr Arg Lys His Tyr Gln
        355                 360                 365

Pro Tyr Ala Pro Pro Arg Asp Phe Ala Ala Tyr Arg Ser Arg Val Lys
    370                 375                 380

Phe Ser Arg Ser Ala Asp Ala Pro Ala Tyr Gln Gln Gly Gln Asn Gln
385                 390                 395                 400
```

```
Leu Tyr Asn Glu Leu Asn Leu Gly Arg Arg Glu Tyr Asp Val Leu
                405                 410                 415

Asp Lys Arg Arg Gly Arg Asp Pro Glu Met Gly Gly Lys Pro Gln Arg
            420                 425                 430

Arg Lys Asn Pro Gln Glu Gly Leu Tyr Asn Glu Leu Gln Lys Asp Lys
            435                 440                 445

Met Ala Glu Ala Tyr Ser Glu Ile Gly Met Lys Gly Glu Arg Arg Arg
450                 455                 460

Gly Lys Gly His Asp Gly Leu Tyr Gln Gly Leu Ser Thr Ala Thr Lys
465                 470                 475                 480

Asp Thr Tyr Asp Ala Leu His Met Gln Ala Leu Pro Pro Arg
                485                 490
```

<210> SEQ ID NO 50
<211> LENGTH: 536
<212> TYPE: PRT
<213> ORGANISM: Artificial sequence
<220> FEATURE:
<221> NAME/KEY: MISC_FEATURE
<223> OTHER INFORMATION: P3F2-28BBZ amino acid sequence

<400> SEQUENCE: 50

```
Met Ala Leu Pro Val Thr Ala Leu Leu Leu Pro Leu Ala Leu Leu Leu
1               5                   10                  15

His Ala Ala Arg Pro Gln Met Gln Leu Val Gln Ser Gly Ala Glu Val
            20                  25                  30

Lys Lys Pro Gly Ala Ser Val Lys Val Ser Cys Lys Ala Ser Gly Tyr
        35                  40                  45

Thr Phe Thr Ser Tyr Tyr Met His Trp Val Arg Gln Ala Pro Gly Gln
    50                  55                  60

Gly Leu Glu Trp Met Gly Ile Ile Asn Pro Ser Gly Gly Ser Thr Ser
65                  70                  75                  80

Tyr Ala Gln Lys Phe Gln Gly Arg Val Thr Met Thr Arg Asp Thr Ser
                85                  90                  95

Thr Ser Thr Val Tyr Met Glu Leu Ser Ser Leu Arg Ser Glu Asp Thr
            100                 105                 110

Ala Val Tyr Tyr Cys Ala Ser Ser Arg Ser Gly Thr Val Val Asn
        115                 120                 125

His Asp Ala Phe Asp Ile Trp Gly Lys Gly Thr Thr Val Thr Val Ser
    130                 135                 140

Ser Gly Gly Gly Gly Ser Gly Gly Gly Ser Gly Gly Gly Gly Ser
145                 150                 155                 160

Asp Ile Gln Leu Thr Gln Ser Pro Ser Ser Leu Ser Ala Ser Val Gly
                165                 170                 175

Asp Arg Val Thr Ile Thr Cys Arg Ala Ser Gln Val Ile Ser Arg Ala
            180                 185                 190

Leu Ala Trp Tyr Gln Gln Thr Pro Gly Lys Pro Pro Lys Leu Leu Ile
        195                 200                 205

Tyr Asp Ala Ser Asn Leu Gln Ser Gly Val Pro Ser Arg Phe Ser Gly
    210                 215                 220

Ser Gly Ser Gly Thr Asp Phe Thr Leu Thr Ile Ser Arg Leu Gln Pro
225                 230                 235                 240

Glu Asp Phe Ala Thr Tyr Tyr Cys Gln Gln Phe Asn Ser Tyr Pro Leu
                245                 250                 255

Thr Phe Gly Gly Gly Thr Lys Leu Glu Ile Lys Arg Thr Thr Thr Pro
            260                 265                 270
```

Ala Pro Arg Pro Pro Thr Pro Ala Pro Thr Ile Ala Ser Gln Pro Leu
            275                 280                 285

Ser Leu Arg Pro Glu Ala Cys Arg Pro Ala Ala Gly Gly Ala Val His
        290                 295                 300

Thr Arg Gly Leu Asp Phe Ala Cys Asp Phe Trp Val Leu Val Val Val
305                 310                 315                 320

Gly Gly Val Leu Ala Cys Tyr Ser Leu Leu Val Thr Val Ala Phe Ile
                325                 330                 335

Ile Phe Trp Val Arg Ser Lys Arg Ser Arg Leu Leu His Ser Asp Tyr
            340                 345                 350

Met Asn Met Thr Pro Arg Arg Pro Gly Pro Thr Arg Lys His Tyr Gln
            355                 360                 365

Pro Tyr Ala Pro Pro Arg Asp Phe Ala Ala Tyr Arg Ser Lys Arg Gly
        370                 375                 380

Arg Lys Lys Leu Leu Tyr Ile Phe Lys Gln Pro Phe Met Arg Pro Val
385                 390                 395                 400

Gln Thr Thr Gln Glu Glu Asp Gly Cys Ser Cys Arg Phe Pro Glu Glu
                405                 410                 415

Glu Glu Gly Gly Cys Glu Leu Arg Val Lys Phe Ser Arg Ser Ala Asp
            420                 425                 430

Ala Pro Ala Tyr Gln Gln Gly Gln Asn Gln Leu Tyr Asn Glu Leu Asn
            435                 440                 445

Leu Gly Arg Arg Glu Glu Tyr Asp Val Leu Asp Lys Arg Arg Gly Arg
        450                 455                 460

Asp Pro Glu Met Gly Gly Lys Pro Gln Arg Arg Lys Asn Pro Gln Glu
465                 470                 475                 480

Gly Leu Tyr Asn Glu Leu Gln Lys Asp Lys Met Ala Glu Ala Tyr Ser
                485                 490                 495

Glu Ile Gly Met Lys Gly Glu Arg Arg Arg Gly Lys Gly His Asp Gly
            500                 505                 510

Leu Tyr Gln Gly Leu Ser Thr Ala Thr Lys Asp Thr Tyr Asp Ala Leu
        515                 520                 525

His Met Gln Ala Leu Pro Pro Arg
            530                 535

<210> SEQ ID NO 51
<211> LENGTH: 14
<212> TYPE: PRT
<213> ORGANISM: Homo Sapiens

<400> SEQUENCE: 51

Thr Leu Arg Ser Gly Ile Asn Val Gly Ile Tyr Arg Ile Tyr
1               5                   10

<210> SEQ ID NO 52
<211> LENGTH: 11
<212> TYPE: PRT
<213> ORGANISM: Homo Sapiens

<400> SEQUENCE: 52

Tyr Lys Ser Asp Ser Asp Lys Tyr Gln Gly Ser
1               5                   10

<210> SEQ ID NO 53
<211> LENGTH: 9
<212> TYPE: PRT
<213> ORGANISM: Homo Sapiens

```
<400> SEQUENCE: 53

Met Ile Trp His Ser Gly Gly Trp Val
1               5

<210> SEQ ID NO 54
<211> LENGTH: 12
<212> TYPE: PRT
<213> ORGANISM: Homo Sapiens

<400> SEQUENCE: 54

Gly Asp Thr Val Ser Ser Asp Ser Ala Ala Trp Asn
1               5                   10

<210> SEQ ID NO 55
<211> LENGTH: 18
<212> TYPE: PRT
<213> ORGANISM: Homo Sapiens

<400> SEQUENCE: 55

Arg Thr Tyr Tyr Arg Ser Lys Trp Phe Asn Asp Tyr Ala Val Ser Val
1               5                   10                  15

Lys Gly

<210> SEQ ID NO 56
<211> LENGTH: 11
<212> TYPE: PRT
<213> ORGANISM: Homo Sapiens

<400> SEQUENCE: 56

Ser Asn Ser Tyr Tyr Tyr Tyr Ala Met Asp Val
1               5                   10

<210> SEQ ID NO 57
<211> LENGTH: 11
<212> TYPE: PRT
<213> ORGANISM: Homo Sapiens

<400> SEQUENCE: 57

Arg Ala Ser Gln Val Ile Ser Arg Ala Leu Ala
1               5                   10

<210> SEQ ID NO 58
<211> LENGTH: 7
<212> TYPE: PRT
<213> ORGANISM: Homo Sapiens

<400> SEQUENCE: 58

Asp Ala Ser Asn Leu Gln Ser
1               5

<210> SEQ ID NO 59
<211> LENGTH: 9
<212> TYPE: PRT
<213> ORGANISM: Homo Sapiens

<400> SEQUENCE: 59

Gln Gln Phe Asn Ser Tyr Pro Leu Thr
1               5

<210> SEQ ID NO 60
<211> LENGTH: 10
<212> TYPE: PRT
<213> ORGANISM: Homo Sapiens
```

<400> SEQUENCE: 60

Gly Tyr Thr Phe Thr Ser Tyr Tyr Met His
1               5                   10

<210> SEQ ID NO 61
<211> LENGTH: 17
<212> TYPE: PRT
<213> ORGANISM: Homo Sapiens

<400> SEQUENCE: 61

Ile Ile Asn Pro Ser Gly Gly Ser Thr Ser Tyr Ala Gln Lys Phe Gln
1               5                   10                  15

Gly

<210> SEQ ID NO 62
<211> LENGTH: 15
<212> TYPE: PRT
<213> ORGANISM: Homo Sapiens

<400> SEQUENCE: 62

Ser Arg Ser Gly Thr Thr Val Val Asn His Asp Ala Phe Asp Ile
1               5                   10                  15

<210> SEQ ID NO 63
<211> LENGTH: 25
<212> TYPE: DNA
<213> ORGANISM: Artificial sequence
<220> FEATURE:
<221> NAME/KEY: misc_feature
<223> OTHER INFORMATION: primer

<400> SEQUENCE: 63
accacgacgc cagcgccgcg accac                                          25

<210> SEQ ID NO 64
<211> LENGTH: 22
<212> TYPE: DNA
<213> ORGANISM: Artificial sequence
<220> FEATURE:
<221> NAME/KEY: misc_feature
<223> OTHER INFORMATION: primer

<400> SEQUENCE: 64
tagcgtaaaa ggagcaacat ag                                             22

<210> SEQ ID NO 65
<211> LENGTH: 622
<212> TYPE: PRT
<213> ORGANISM: Homo Sapiens

<400> SEQUENCE: 65

Met Ala Leu Pro Thr Ala Arg Pro Leu Leu Gly Ser Cys Gly Thr Pro
1               5                   10                  15

Ala Leu Gly Ser Leu Leu Phe Leu Leu Phe Ser Leu Gly Trp Val Gln
                20                  25                  30

Pro Ser Arg Thr Leu Ala Gly Glu Thr Gly Gln Glu Ala Ala Pro Leu
            35                  40                  45

Asp Gly Val Leu Ala Asn Pro Pro Asn Ile Ser Ser Leu Ser Pro Arg
        50                  55                  60

Gln Leu Leu Gly Phe Pro Cys Ala Glu Val Ser Gly Leu Ser Thr Glu
65                  70                  75                  80

```
Arg Val Arg Glu Leu Ala Val Ala Leu Ala Gln Lys Asn Val Lys Leu
             85                  90                  95

Ser Thr Glu Gln Leu Arg Cys Leu Ala His Arg Leu Ser Glu Pro Pro
        100                 105                 110

Glu Asp Leu Asp Ala Leu Pro Leu Asp Leu Leu Phe Leu Asn Pro
        115                 120                 125

Asp Ala Phe Ser Gly Pro Gln Ala Cys Thr Arg Phe Phe Ser Arg Ile
130                 135                 140

Thr Lys Ala Asn Val Asp Leu Leu Pro Arg Gly Ala Pro Glu Arg Gln
145                 150                 155                 160

Arg Leu Leu Pro Ala Ala Leu Ala Cys Trp Gly Val Arg Gly Ser Leu
                165                 170                 175

Leu Ser Glu Ala Asp Val Arg Ala Leu Gly Gly Leu Ala Cys Asp Leu
            180                 185                 190

Pro Gly Arg Phe Val Ala Glu Ser Ala Glu Val Leu Leu Pro Arg Leu
        195                 200                 205

Val Ser Cys Pro Gly Pro Leu Asp Gln Asp Gln Glu Ala Ala Arg
    210                 215                 220

Ala Ala Leu Gln Gly Gly Pro Pro Tyr Gly Pro Pro Ser Thr Trp
225                 230                 235                 240

Ser Val Ser Thr Met Asp Ala Leu Arg Gly Leu Leu Pro Val Leu Gly
                245                 250                 255

Gln Pro Ile Ile Arg Ser Ile Pro Gln Gly Ile Val Ala Ala Trp Arg
            260                 265                 270

Gln Arg Ser Ser Arg Asp Pro Ser Trp Arg Gln Pro Glu Arg Thr Ile
        275                 280                 285

Leu Arg Pro Arg Phe Arg Arg Glu Val Glu Lys Thr Ala Cys Pro Ser
    290                 295                 300

Gly Lys Lys Ala Arg Glu Ile Asp Glu Ser Leu Ile Phe Tyr Lys Lys
305                 310                 315                 320

Trp Glu Leu Glu Ala Cys Val Asp Ala Ala Leu Leu Ala Thr Gln Met
                325                 330                 335

Asp Arg Val Asn Ala Ile Pro Phe Thr Tyr Glu Gln Leu Asp Val Leu
            340                 345                 350

Lys His Lys Leu Asp Glu Leu Tyr Pro Gln Gly Tyr Pro Glu Ser Val
        355                 360                 365

Ile Gln His Leu Gly Tyr Leu Phe Leu Lys Met Ser Pro Glu Asp Ile
    370                 375                 380

Arg Lys Trp Asn Val Thr Ser Leu Glu Thr Leu Lys Ala Leu Leu Glu
385                 390                 395                 400

Val Asn Lys Gly His Glu Met Ser Pro Gln Val Ala Thr Leu Ile Asp
                405                 410                 415

Arg Phe Val Lys Gly Arg Gly Gln Leu Asp Lys Asp Thr Leu Asp Thr
            420                 425                 430

Leu Thr Ala Phe Tyr Pro Gly Tyr Leu Cys Ser Leu Ser Pro Glu Glu
        435                 440                 445

Leu Ser Ser Val Pro Pro Ser Ser Ile Trp Ala Val Arg Pro Gln Asp
    450                 455                 460

Leu Asp Thr Cys Asp Pro Arg Gln Leu Asp Val Leu Tyr Pro Lys Ala
465                 470                 475                 480

Arg Leu Ala Phe Gln Asn Met Asn Gly Ser Glu Tyr Phe Val Lys Ile
                485                 490                 495

Gln Ser Phe Leu Gly Gly Ala Pro Thr Glu Asp Leu Lys Ala Leu Ser
```

```
                500                 505                 510
Gln Gln Asn Val Ser Met Asp Leu Ala Thr Phe Met Lys Leu Arg Thr
            515                 520                 525

Asp Ala Val Leu Pro Leu Thr Val Ala Glu Val Gln Lys Leu Leu Gly
        530                 535                 540

Pro His Val Glu Gly Leu Lys Ala Glu Glu His Arg Pro Val Arg
545                 550                 555                 560

Asp Trp Ile Leu Arg Gln Arg Gln Asp Leu Asp Thr Leu Gly Leu
                565                 570                 575

Gly Leu Gln Gly Gly Ile Pro Asn Gly Tyr Leu Val Leu Asp Leu Ser
            580                 585                 590

Met Gln Glu Ala Leu Ser Gly Thr Pro Cys Leu Leu Gly Pro Gly Pro
        595                 600                 605

Val Leu Thr Val Leu Ala Leu Leu Leu Ala Ser Thr Leu Ala
        610                 615                 620

<210> SEQ ID NO 66
<211> LENGTH: 95
<212> TYPE: PRT
<213> ORGANISM: Artificial sequence
<220> FEATURE:
<223> OTHER INFORMATION: human mesothelin fragment

<400> SEQUENCE: 66

Glu Val Glu Lys Thr Ala Cys Pro Ser Gly Lys Lys Ala Arg Glu Ile
1               5                   10                  15

Asp Glu Ser Leu Ile Phe Tyr Lys Lys Trp Glu Leu Glu Ala Cys Val
            20                  25                  30

Asp Ala Ala Leu Leu Ala Thr Gln Met Asp Arg Val Asn Ala Ile Pro
        35                  40                  45

Phe Thr Tyr Glu Gln Leu Asp Val Leu Lys His Lys Leu Asp Glu Leu
    50                  55                  60

Tyr Pro Gln Gly Tyr Pro Glu Ser Val Ile Gln His Leu Gly Tyr Leu
65                  70                  75                  80

Phe Leu Lys Met Ser Pro Glu Asp Ile Arg Lys Trp Asn Val Thr
                85                  90                  95

<210> SEQ ID NO 67
<211> LENGTH: 95
<212> TYPE: PRT
<213> ORGANISM: Artificial sequence
<220> FEATURE:
<223> OTHER INFORMATION: human mesothelin fragment

<400> SEQUENCE: 67

Ser Leu Glu Thr Leu Lys Ala Leu Leu Glu Val Asn Lys Gly His Glu
1               5                   10                  15

Met Ser Pro Gln Val Ala Thr Leu Ile Asp Arg Phe Val Lys Gly Arg
            20                  25                  30

Gly Gln Leu Asp Lys Asp Thr Leu Asp Thr Leu Thr Ala Phe Tyr Pro
        35                  40                  45

Gly Tyr Leu Cys Ser Leu Ser Pro Glu Glu Leu Ser Ser Val Pro Pro
    50                  55                  60

Ser Ser Ile Trp Ala Val Arg Pro Gln Asp Leu Asp Thr Cys Asp Pro
65                  70                  75                  80

Arg Gln Leu Asp Val Leu Tyr Pro Lys Ala Arg Leu Ala Phe Gln
                85                  90                  95
```

<210> SEQ ID NO 68
<211> LENGTH: 95
<212> TYPE: PRT
<213> ORGANISM: Artificial sequence
<220> FEATURE:
<223> OTHER INFORMATION: human mesothelin fragment

<400> SEQUENCE: 68

Asn Met Asn Gly Ser Glu Tyr Phe Val Lys Ile Gln Ser Phe Leu Gly
1               5                   10                  15

Gly Ala Pro Thr Glu Asp Leu Lys Ala Leu Ser Gln Gln Asn Val Ser
            20                  25                  30

Met Asp Leu Ala Thr Phe Met Lys Leu Arg Thr Asp Ala Val Leu Pro
        35                  40                  45

Leu Thr Val Ala Glu Val Gln Lys Leu Leu Gly Pro His Val Glu Gly
    50                  55                  60

Leu Lys Ala Glu Glu Arg His Arg Pro Val Arg Asp Trp Ile Leu Arg
65                  70                  75                  80

Gln Arg Gln Asp Asp Leu Asp Thr Leu Gly Leu Gly Leu Gln Gly
                85                  90                  95

<210> SEQ ID NO 69
<211> LENGTH: 42
<212> TYPE: PRT
<213> ORGANISM: Artificial sequence
<220> FEATURE:
<223> OTHER INFORMATION: human mesothelin fragment

<400> SEQUENCE: 69

Glu Val Glu Lys Thr Ala Cys Pro Ser Gly Lys Lys Ala Arg Glu Ile
1               5                   10                  15

Asp Glu Ser Leu Ile Phe Tyr Lys Lys Trp Glu Leu Glu Ala Cys Val
            20                  25                  30

Asp Ala Ala Leu Leu Ala Thr Gln Met Asp
        35                  40

<210> SEQ ID NO 70
<211> LENGTH: 42
<212> TYPE: PRT
<213> ORGANISM: Artificial sequence
<220> FEATURE:
<223> OTHER INFORMATION: human mesothelin fragment

<400> SEQUENCE: 70

Asp Ala Ala Leu Leu Ala Thr Gln Met Asp Arg Val Asn Ala Ile Pro
1               5                   10                  15

Phe Thr Tyr Glu Gln Leu Asp Val Leu Lys His Lys Leu Asp Glu Leu
            20                  25                  30

Tyr Pro Gln Gly Tyr Pro Glu Ser Val Ile
        35                  40

<210> SEQ ID NO 71
<211> LENGTH: 31
<212> TYPE: PRT
<213> ORGANISM: Artificial sequence
<220> FEATURE:
<223> OTHER INFORMATION: human mesothelin fragment

<400> SEQUENCE: 71

Tyr Pro Gln Gly Tyr Pro Glu Ser Val Ile Gln His Leu Gly Tyr Leu
1               5                   10                  15

```
Phe Leu Lys Met Ser Pro Glu Asp Ile Arg Lys Trp Asn Val Thr
            20                  25                  30
```

<210> SEQ ID NO 72
<211> LENGTH: 64
<212> TYPE: PRT
<213> ORGANISM: Artificial sequence
<220> FEATURE:
<223> OTHER INFORMATION: human mesothelin fragment

<400> SEQUENCE: 72

```
Glu Val Glu Lys Thr Ala Cys Pro Ser Gly Lys Lys Ala Arg Glu Ile
1               5                   10                  15

Asp Glu Ser Leu Ile Phe Tyr Lys Lys Trp Glu Leu Glu Ala Cys Val
            20                  25                  30

Asp Ala Ala Leu Leu Ala Thr Gln Met Asp Arg Val Asn Ala Ile Pro
        35                  40                  45

Phe Thr Tyr Glu Gln Leu Asp Val Leu Lys His Lys Leu Asp Glu Leu
    50                  55                  60
```

<210> SEQ ID NO 73
<211> LENGTH: 63
<212> TYPE: PRT
<213> ORGANISM: Artificial sequence
<220> FEATURE:
<223> OTHER INFORMATION: human mesothelin fragment

<400> SEQUENCE: 73

```
Asp Ala Ala Leu Leu Ala Thr Gln Met Asp Arg Val Asn Ala Ile Pro
1               5                   10                  15

Phe Thr Tyr Glu Gln Leu Asp Val Leu Lys His Lys Leu Asp Glu Leu
            20                  25                  30

Tyr Pro Gln Gly Tyr Pro Glu Ser Val Ile Gln His Leu Gly Tyr Leu
        35                  40                  45

Phe Leu Lys Met Ser Pro Glu Asp Ile Arg Lys Trp Asn Val Thr
    50                  55                  60
```

<210> SEQ ID NO 74
<211> LENGTH: 30
<212> TYPE: PRT
<213> ORGANISM: Artificial sequence
<220> FEATURE:
<223> OTHER INFORMATION: human mesothelin fragment

<400> SEQUENCE: 74

```
Tyr Lys Lys Trp Glu Leu Glu Ala Cys Val Asp Ala Ala Leu Leu Ala
1               5                   10                  15

Thr Gln Met Asp Arg Val Asn Ala Ile Pro Phe Thr Tyr Glu
            20                  25                  30
```

<210> SEQ ID NO 75
<211> LENGTH: 20
<212> TYPE: PRT
<213> ORGANISM: Artificial sequence
<220> FEATURE:
<223> OTHER INFORMATION: human mesothelin fragment

<400> SEQUENCE: 75

```
Leu Glu Ala Cys Val Asp Ala Ala Leu Leu Ala Thr Gln Met Asp Arg
1               5                   10                  15

Val Asn Ala Ile
            20
```

FULLY HUMAN ANTI-MESOTHELIN ANTIBODIES AND IMMUNE EFFECTOR CELLS TARGETING MESOTHELIN

TECHNICAL FIELD

The present invention relates to the field of immunotherapy or diagnosis of tumor, and in particular, to fully human anti-mesothelin antibodies and immune effector cells targeting mesothelin.

BACKGROUND

The role of immune effector cells in the tumor immune response is gaining more and more attention. Adoptive immunotherapy based on immune effector cells has achieved some effects in some tumors, and this immunotherapy method can overcome the defects of antibody treatment, however the therapeutic effects in most tumors are still unsatisfactory [Grupp S A, et al. Adoptive cellular therapy. Curr Top Microbiol Immunol., 2011; 344: 149-72.]. In recent years, it was discovered that the recognition specificity of cytotoxic lymphocytes (CTLs) to target cells depends on T cell receptors (TCRs), scFv of antibodies against tumor cell associated antigens and intracellular signal-activating motifs of T lymphocyte receptor CD3ζ or FcεRIγ were fused to a chimeric antigen receptor (CAR), and T lymphocyte was genetically modified by the chimeric antigen receptors on its surface by means of, for example, lentivirus infection. Such CAR T lymphocytes are capable of selectively targeting T lymphocytes to tumor cells and specifically killing the tumor in a non-limiting manner by Major Histocompatibility Complex (MHC). CAR T lymphocyte is a new immunotherapy strategy in the field of tumor immunotherapy. CAR modified NK cells or NKT cells also exhibit antitumor activities in preclinical studies.

When designing CAR-modified immune effector cells, especially T cells, the targeted antigen genes are in fact a crucial choice. Given the complexity of gene expressions in vivo and various uncontrollable factors, selection for suitable genes for a CAR is very difficult. Moreover, for many tumor-specific antigens, it is difficult to find a specific molecule directed against them and suitable for constructing CAR-modified immune effector cells.

Mesothelin is a cell surface glycoprotein, molecular weight of which is 40-kDa. It is highly expressed in a variety of tumors, such as pancreatic cancer, ovarian cancer, and thymus mesothelioma. In normal tissues, it is expressed only on the normal mesothelial cells of the pleura, pericardium and peritoneum. Mesothelin is synthesized as a 71 kDa precursor protein, the mature portion of which is expressed on the cell surface. The precursor protein is proteolytically cleaved by furin into a 31 kDa shedding part (termed megakaryocyte chimeric factor, or MPF) and a 40 kDa mesothelin fraction). The latter component may remain bound to the cell surface via GPI linkage and may also shed off via the proteolytic enzyme mechanism.

Antibodies against mesothelin or other targeted therapies have been reported. CAR-T has also been reported in clinical studies (Maus M V, Haas A R, Beatty G L, Albelda S M, Levine B L, Liu X, Zhao Y, Kalos M, June C H. T cells expressing chimeric antigen receptors can cause anaphylaxis in humans. Cancer Immunol Res. 2013; 1 (1): 26-31; Beatty G L, Haas A R, Maus M V, Torigian D A, Soulen M C, Plesa G, Chew A, Zhao Y, Levine B L, Albelda S M, Kalos M, June C H. Mesothelin-specific chimeric antigen receptor mRNA-engineered T cells induce anti-tumor activity in solid malignancies. Cancer Immunol Res. 2014 February; 2 (2): 112-20). However, it has also been found that CAR-T constructed with mouse anti-human mesothelin antibody clinically shows side effects, such as anti-mouse antibody and allergy, indicating that mesothelin may be a potential therapeutic target, but the properties of the antibody itself may affect its efficacy and side effects. Therefore, there is still a need in the art to find solutions that can overcome problems caused by antibodies that are not ideal or have toxic side effects.

SUMMARY OF THE INVENTION

It is an object of the present invention to provide fully human anti-mesothelin antibodies as well as immune effector cells targeting mesothelin.

In the first aspect of the invention, a fully human antibody that specifically binds to mesothelin is provided, which is selected from a group consisting of:

(a) an antibody comprising a heavy chain variable region having CDR1 comprising the amino acid sequence of SEQ ID NO: 54, CDR2 comprising the amino acid sequence of SEQ ID NO: 55, CDR3 comprising the amino acid sequence of SEQ ID NO: 56;

(b) an antibody comprising a light chain variable region having CDR1 comprising the amino acid sequence of SEQ ID NO: 51, CDR2 comprising the amino acid sequence of SEQ ID NO: 52, CDR3 comprising the amino acid sequence of SEQ ID NO: 53;

(c) an antibody comprising a heavy chain variable region of said antibody of (a) and a light chain variable region of said antibody of (b);

(d) an antibody comprising a heavy chain variable region having CDR1 comprising the amino acid sequence of SEQ ID NO: 60, CDR2 comprising the amino acid sequence of SEQ ID NO: 61, CDR3 of the amino acid sequence of ID NO: 62;

(e) an antibody comprising a light chain variable region having CDR1 comprising the amino acid sequence of SEQ ID NO: 57, CDR2 comprising the amino acid sequence of SEQ ID NO: 58, CDR3 of the amino acid of ID NO: 59;

(f) an antibody comprising a heavy chain variable region of said antibody of (d) and a light chain variable region of said antibody of (e);

(g) an antibody which recognizes the same antigenic determinant as that recognized by the antibody according to any one of (a) to (f).

In a preferred embodiment, the fully human antibody comprises a heavy chain variable region and a light chain variable region, the amino acid sequence of the heavy chain variable region is shown in positions 1 to 123 of SEQ ID NO: 6; and the amino acid sequence of the light chain variable region is shown in positions 139-254 of SEQ ID NO: 6; or
the fully human antibody comprises a heavy chain variable region and a light chain variable region, the amino acid sequence of the heavy chain variable region is shown in positions 1 to 124 of SEQ ID NO: 8; and the amino acid sequence of the light chain variable region is shown in positions 140-247 of SEQ ID NO: 8.

In another preferred embodiment, the fully human antibody that specifically binds to mesothelin may be single chain antibody (scFV), monoclonal antibody, domain antibody, Fab fragment, Fd fragment, Fv fragment, F (ab')$_2$ fragment and a derivative thereof, or other forms of antibody; preferably single chain antibody.

In another aspect of the invention, a nucleic acid encoding the antibody is provided.

In another aspect of the invention, an expression vector comprising the nucleic acid is provided.

In another aspect of the invention, a host cell is provided, which comprises the expression vector or has the nucleic acid integrated into the genome.

In another aspect of the present invention, use of the antibodies described above is provided for the preparation of a targeted drug, antibody-drug conjugate, or a polyfunctional antibody that specifically targets tumor cells expressing mesothelin; or for the preparation of a reagent for diagnosing a tumor expressing mesothelin; or for the preparation of chimeric antigen receptor-modified immune cells.

In another aspect of the present invention, a chimeric antigen receptor (CAR) of the antibody is provided, and said chimeric antigen receptor comprises sequentially linked: the antibody of the present invention, a transmembrane region and intracellular signal region.

In a preferred embodiment, the intracellular signal region is selected from a group consisting of intracellular signal region sequences of CD3ζ, FcεRIγ, CD27, CD28, CD137, CD134, MyD88, CD40 or a combination thereof.

In another preferred embodiment, the transmembrane region comprises a transmembrane region of CD8 or CD28.

In another preferred embodiment, the chimeric antigen receptor comprises the following sequentially linked antibody, transmembrane region and intracellular signal region:

The antibody, CD8 and CD3ζ;

The antibody, CD8, CD137 and CD3ζ;

The antibody, the transmembrane region of CD28 molecule, the intracellular signal region of CD28 molecule and CD3ζ; or The antibody, the transmembrane region of CD28 molecule, the intracellular signal region of CD28 molecule, CD137 and CD3ζ.

In another preferred embodiment, the antibody is a single chain antibody or domain antibody.

In another preferred embodiment, the chimeric antigen receptor has:

SEQ ID NO: 41 or the amino acid sequence shown in positions 22-353 thereof;

SEQ ID NO: 42 or the amino acid sequence shown in positions 22-454 thereof;

SEQ ID NO: 43 or the amino acid sequence shown in positions 22-498 thereof;

SEQ ID NO: 44 or the amino acid sequence shown in positions 22-501 thereof;

SEQ ID NO: 45 or the amino acid sequence shown in positions 22-543 thereof;

SEQ ID NO: 46 or the amino acid sequence shown in positions 22-346 thereof;

SEQ ID NO: 47 or the amino acid sequence shown in positions 22-447 thereof;

SEQ ID NO: 48 or the amino acid sequence shown in positions 22-491 thereof;

SEQ ID NO: 49 or the amino acid sequence shown in positions 22-494 thereof; or

SEQ ID NO: 50 or the amino acid sequence shown in positions 22-536 thereof.

In another aspect of the invention, a nucleic acid encoding the chimeric antigen receptor is provided.

In another preferred embodiment, the nucleic acid encoding the chimeric antigen receptor has:

SEQ ID NO: 31 or the nucleotide sequence set forth in positions 473-1468 thereof;

SEQ ID NO: 32 or the nucleotide sequence set forth in positions 473-1771 thereof;

SEQ ID NO: 33 or the nucleotide sequence set forth in positions 473-1903 thereof;

SEQ ID NO: 34 or the nucleotide sequence set forth in positions 473-1912 thereof;

SEQ ID NO: 35 or the nucleotide sequence set forth in positions 473-2038 thereof;

SEQ ID NO: 36 or the nucleotide sequence set forth in positions 473-1447 thereof;

SEQ ID NO: 37 or the nucleotide sequence set forth in positions 473-1750 thereof;

SEQ ID NO: 38 or the nucleotide sequence set forth in positions 473-1882 thereof;

SEQ ID NO: 39 or the nucleotide sequence set forth in positions 473-1891 thereof;

SEQ ID NO: 40 or the nucleotide sequence set forth in positions 473 to 2017 thereof.

In another aspect of the present invention, an expression vector comprising the nucleic acid is provided.

In another preferred embodiment, the expression vector is derived from lentiviral plasmid pWPT (or pWPT-eGFP).

In another aspect of the present invention, a virus comprising said vector is provided.

In another aspect of the invention, use of the chimeric antigen receptor, or the nucleic acid, or the expression vector, or the virus is provided for the preparation of genetically modified immune cells targeting tumor cells expressing mesothelin.

In a preferred embodiment, the mesothelin-expressing tumor includes, but is not limited to pancreatic cancer, ovarian cancer and thymus mesothelioma.

In another aspect of the present invention, a genetically modified immune cell is provided, which is transduced with the nucleic acid, or the expression vector or the virus; or expresses the chimeric antigen receptor on its surface-expressed.

In a preferred embodiment, the immune cell further carries an encoding sequence of an exogenous cytokine; and preferably, the cytokine includes: IL-12, IL-15 or IL-21.

In another preferred embodiment, the immune cell also expresses another chimeric antigen receptor which does not contain CD3ζ but contains the intracellular signaling domain of CD28, the intracellular signaling domain of CD137, or a combination of both.

In another preferred embodiment, the immune cell further expresses a chemokine receptor; and preferably, the chemokine receptor includes: CCR2.

In another preferred embodiment, the immune cell further expresses siRNA which can reduce expression of PD-1 or a protein which blocks PD-L1.

In another preferred embodiment, the immune cell further expresses a safety switch; and preferably, the safety switch includes iCaspase-9, Truncated EGFR or RQR8.

In another preferred embodiment, the immune cells include T lymphocytes, NK cells or NKT cells.

In another aspect of the invention, use of the genetically modified immune cells is provided for the preparation of a tumor-inhibiting drug, and the tumor is a tumor expressing mesothelin.

In another aspect of the present invention, a multi-functional immunoconjugate is provided, comprising: any one of the above described antibodies; and a functional molecule linked thereto (including covalently linked, conjugated, attached, adsorbed); the functional molecule is selected from a group consisting of a molecule that targets a tumor surface marker, a tumor-suppressing molecule, a molecule that targets a surface marker of an immune cell, or a detectable label.

In a preferred embodiment, in the multifunctional immunoconjugate, the molecule that targets the tumor surface marker is an antibody or ligand that binds to a tumor surface marker; or the tumor-suppressing molecule is an anti-tumor cytokine or an anti-tumor toxin; and preferably, the cytokines include but are not limited to: IL-12, IL-15, IFN-beta, TNF-alpha.

In another preferred embodiment, in the multi-functional immunoconjugate, the detectable label includes a fluorescent label or a chromogenic label.

In another preferred embodiment, in the multifunctional immunoconjugate, the antibody that binds to a tumor surface marker refers to an antibody that recognizes an antigen other than mesothelin, and the other antigen includes EGFR EGFRvIII, mesothelin, HER2, EphA2, Her3, EpCAM, MUC1, MUC16, CEA, Claudin 18.2, folate receptor, Claudin 6, CD3, WT1, NY-ESO-1, MAGE 3, ASGPR1 or CDH16.

In another preferred embodiment, in the multifunctional immunoconjugate, the molecule that targets the surface marker of the immune cell is an antibody that binds to T cell surface marker and forms a T-cell-engaging bifunctional antibody with the above described antibody (bispecific T cell engager, BiTE).

In another preferred embodiment, in the multifunctional immunoconjugate, the antibody that binds to T cell surface marker is an anti-CD3 antibody.

In another preferred embodiment, the anti-CD3 antibody is a single chain antibody (scFV), a monoclonal antibody, a Fab fragment, an Fd fragment, an Fv fragment, an F(ab')$_2$ fragment and a derivative thereof, antibody; preferably single chain antibody.

In another preferred embodiment, the anti-CD3 antibody is humanized, fully human, chimeric or murine antibody.

In another preferred embodiment, the multifunctional immunoconjugate is a fusion polypeptide, and further comprises a linker peptide (linker) between the above described antibody of the invention and the functional molecule linked thereto.

In another preferred embodiment, the linker peptide has the sequence (GlyGlyGlyGlySer)n, wherein n is an integer from 1 to 5; more preferably, n=3.

In another preferred embodiment, the multi-functional immunoconjugate is administered in a form of polypeptide or in the manner of gene administration.

In another aspect of the invention, a nucleic acid encoding the multi-functional immunoconjugate is provided.

In another aspect of the present invention, use of the multi-functional immunoconjugate is provided, for the preparation of an antineoplastic agent or an agent for diagnosis of tumors that express mesothelin; or for the preparation of chimeric antigen receptor modified immune cells; and preferably, the immune cells include T lymphocyte, NK cell or NKT lymphocyte.

In another aspect of the invention, a pharmaceutical composition (including medicament or diagnostic reagent) is provided, comprising:

the antibody or a nucleic acid encoding the antibody; or the immunoconjugate or a nucleic acid encoding the conjugate; or the chimeric antigen receptor or a nucleic acid encoding the chimeric antigen receptor; or the genetically modified immune cell.

In another aspect of the invention, an antibody is provided, which is capable of competing for binding to mesothelin with the antibody of the invention.

In another aspect of the invention, an antibody is provided, which is capable of binding to mesothelin epitope as shown in SEQ ID NO: 66. In a preferred embodiment, an antibody that binds to mesothelin epitope as shown in SEQ ID NO: 72 is also provided.

Other aspects of the invention will be apparent to a skilled person in the art from the disclosure herein.

DESCRIPTION OF DRAWINGS

FIG. 5. Binding curves of monoclonal antibody P1A6E to different concentrations of human mesothelin in Biacore.

FIG. 6. Binding curve of the monoclonal antibody P3F2 to different concentrations of human mesothelin in Biacore.

FIG. 7. Assay of specific binding of four single-chain antibodies (P1A6E, P3F2 and control antibodies SS, C10) to PANC-1-MSLN cells as shown by Fluorescence Activated Cell Sorter (FACS).

FIG. 8. Assay of specific binding of four monoclonal antibodies (P1A6E, P3F2 and control antibody SS, C10) to PANC-1-MSLN cells as shown by Fluorescence Activated Cell Sorter (FACS).

MODE FOR CARRYING OUT THE INVENTION

Figure 1:
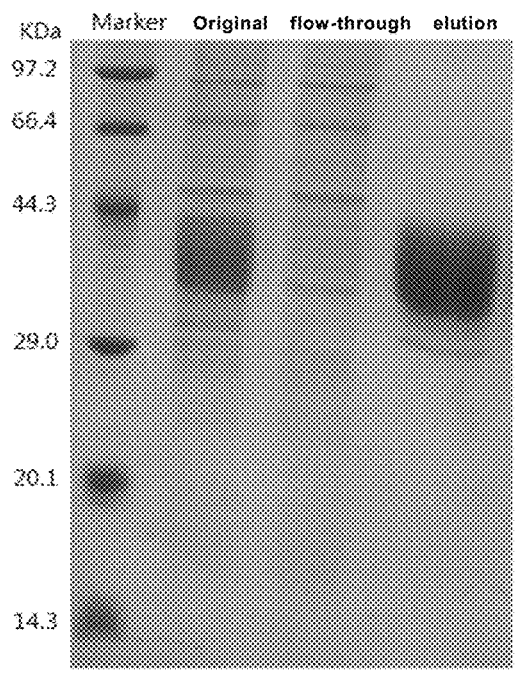
FIG. 1. Binding of antibodies P1A6E and P3F2 to hu-mesothelin and control BSA in a single-phage ELISA assay. The values of antibodies P1A6E and P3F2 against human mesothelin and negative control BSA demonstrated that the two selected antibodies could specifically bind to human mesothelin.

The present inventors investigated many kinds of tumor-specific genes in the early stage and found that a significant proportion of these genes were also expressed in normal cells of some tissues and were relatively difficult to be applied to immune effector cell technology of chimeric antigen receptor modification. Some tumor specific genes exhibit better tumor-specific expression characteristics, however, the CAR-modified immune effector cells based on them have no tumor cell killing activity or low activity, because the target can induce secretion of immune effect cell-inhibiting factors, such as PD-L1 by tumor cells.

After repeated investigation and screening, the present inventors found mesothelin from many candidate molecules as a target for designing CAR. The present inventors have demonstrated that CAR-modified T cells prepared based on antibodies against mesothelin do selectively target mesothelin-positive tumor cells and are highly cytotoxic to tumor cells. The inventors believe that the corresponding CAR-modified immune effector cells, particularly T cells, should be useful for the treatment of human tumors.

Antibodies Against Mesothelin

Specific antibodies which have good binding properties to mesothelin and are suitable for preparing genetically modified immune effector cells, were screened and obtained in all-human natural antibody libraries by the present inventors, and key CDR regions for them to exert their binding properties were also found by the inventors.

Antibodies of the invention may be intact immunoglobulin molecules or antigen-binding fragments, including but not limited to Fab fragments, Fd fragments, Fv fragments, F(ab')$_2$ fragments, complementarity determining region (CDR) fragments, single-chain antibody (scFv), domain antibody, bivalent single chain antibody, single chain phage antibody, bispecific diabody, triple chain antibody, quadruple chain antibody.

The antigen-binding properties of an antibody can be described by three specific regions located in variable regions of the heavy and light chains, termed complementarity determining regions (CDRs), which divide the variable regions into four framework regions (FR), and the amino acid sequences of four FRs are relatively conservative, not directly involved in binding reaction. These CDRs form a loop structure, in which β-folds formed by the FRs are located close to each other in space and the antigen binding site of the antibody is constituted by CDRs on the heavy chain and CDRs on the corresponding light chain. It is possible to determine which amino acids make up FR or CDR regions by comparing the amino acid sequences of the same type of antibody. The CDR regions are sequences of immunologically interesting proteins and the CDR regions of the antibodies of the invention are brand new. The antibody may comprise two, three, four, five, or all six of the CDR regions disclosed herein.

Another aspect of the invention includes functional variants of the antibodies described herein. If the variant is capable of competing with the parental antibody for specific binding to mesothelin 1 and its ability to recognize mesothelin expressed by tumor cells is close to that of the specific antibodies provided in Examples of the present invention. The functional variants may have conservative sequence modifications, including nucleotide and amino acid substitutions, additions and deletions. These modifications can be introduced by standard techniques known in the art, such as directed mutagenesis and random PCR-mediated mutagenesis, and can include both natural and non-natural nucleotides and amino acids. Preferably, modification of the sequence occurs on a region outside the CDR region of the antibody.

The antibodies of the present invention can be applied to prepare various targeted antitumor drugs and drugs for diagnosing tumors, and in particular to prepare immune effector cells targeting mesothelin.

Chimeric Antigen Receptor and Genetically Modified Immune Cell

In the present invention, a chimeric antigen receptor expressed on the surface of an immune effector cell (immune cell) is provided, wherein the chimeric antigen receptor comprises sequentially linked: extracellular binding region, transmembrane region and intracellular signal region, and the extracellular binding region comprises the antibody of the invention. By expressing the chimeric antigen receptor on the surface of immune effector cells, immune effector cells can have a highly specific cytotoxic effect on tumor cells expressing mesothelin.

As used herein, "immune cells" and "immune effector cells" are used interchangeably and include: T lymphocytes, NK cells or NKT cells, and the like.

As a preferred embodiment of the present invention, the antibody contained in the chimeric antigen receptor is a single chain antibody, which is connected to CD8 or the transmembrane region of CD28 through the hinge region of CD8, and the transmembrane region is immediately followed by the intracellular signal region.

The invention also includes nucleic acids encoding the chimeric antigen receptors. The present invention also relates to variants of the above described polynucleotides, which encode a polypeptide, or a fragment, analog and derivative of the polypeptide having the same amino acid sequence as the present invention.

The transmembrane region of the chimeric antigen receptor may be selected from the transmembrane region of a protein such as CD8 or CD28. The human CD8 protein is a heterodimer composed of two chains, αβ or γδ. In one embodiment of the invention, the transmembrane region is selected from the transmembrane region of CD8a or CD28. In addition, the CD8α hinge is a flexible region so that CD8 or CD28 and the transmembrane region as well as the hinge region are used to connect the target recognition domain scFv of the chimeric antigen receptor CAR to the intracellular signal region.

The intracellular signal region may be selected from a group consisting of intracellular signal region of CD3ζ, FcεRIγ, CD27, CD28, CD137, CD134, MyD88, CD4 protein, and combinations thereof. The CD3 molecule consists of five subunits, in which CD3ζ subunit (also known as CD3 zeta, abbreviated as Z) contains 3 ITAM motifs that are important signal transduction regions in TCR-CD3 complex. CD3δZ is a truncated CD3ζ sequence without ITAM motif and is generally constructed in the present invention as a negative control. FcεRIγ is mainly distributed on the surface of mast cells and basophils, which contains an ITAM motif, which is similar to CD3ζ in structure, distribution and function. In addition, as mentioned above, CD28, CD137 and CD134 are co-stimulatory signaling molecules. The co-stimulatory effect of their intracellular signaling segments upon binding to the respective ligands results in the continued proliferation of immune effector cells, primarily T lymphocytes, and increase in the level of cytokines such as IL-2 and IFN-γ secreted by immune effector cells, and the survival period and anti-tumor effect of CAR immune effector cells in vivo are increased.

The chimeric antigen receptor of the present invention can be sequentially linked as follows:

The antibody of the invention, CD8 and CD3ζ;

The antibody of the invention, CD8, CD137 and CD3ζ;

The antibody of the invention, the transmembrane region of CD28 molecule, the intracellular signal region of CD28 molecule and CD3ζ; or The antibodies of the invention, the transmembrane region of CD28 molecule, the intracellular signal region of CD28 molecule, CD137 and CD3.

And combinations thereof, wherein CD28a in the relevant chimeric antigen receptor protein represents the transmembrane region of CD28 molecule and CD28b represents the intracellular signal region of CD28 molecule. The various chimeric antigen receptors described above are collectively referred to as scFv (mesothelin)-CAR.

The present invention also provides a vector comprising the above-mentioned nucleic acid encoding a chimeric antigen receptor protein expressed on the surface of an immune effector cell. In a specific embodiment, the vector used in the present invention is a lentiviral plasmid vector pWPT-eGFP. This plasmid belongs to the third generation of self-inactivating lentiviral vector system. The system has three plasmids, packaging plasmid psPAX2 encoding protein Gag/Pol, encoding Rev protein; envelope plasmid PMD2.G encoding VSV-G protein; and empty vector pWPT-eGFP, which can be used for recombinant introduction of a nucleic acid sequence of interest, i.e., a nucleic acid encoding CAR. In the empty vector pWPT-eGFP, the expression of enhanced green fluorescent protein (eGFP) is regulated by elongation factor-1α (EF-1α) promoter. While in the recombinant expression vector pWPT-eGFP-F2A-CAR containing the nucleic acid sequence encoding CAR, co-expression of eGFP and CAR is achieved by ribosomal skipping sequence 2A (abbreviated as F2A) from food-and-mouth disease virus (FMDV). It is to be understood that other expression vectors are also useful.

The invention also includes viruses comprising the vectors described above. The viruses of the invention include packaged infectious viruses as well as viruses to be packaged that contain the necessary components for packaging into infectious viruses. Other viruses known in the art that can be used to transduce exogenous genes into immune effector cells and their corresponding plasmid vectors are also useful in the present invention.

The present invention further includes a genetically modified T lymphocyte, which is transduced with a nucleic acid of the present invention or transduced with the above-mentioned recombinant plasmid containing the nucleic acid of the present invention or a viral system containing the plasmid. Conventional nucleic acid transduction methods in the art, including non-viral and viral transduction methods, can be used in the present invention. Non-viral transduction methods include electroporation and transposon methods. Recently, nucleofector nuclear transfection instrument developed by Amaxa can directly introduce foreign genes into nucleus to achieve highly efficient transduction of target genes. In addition, compared with conventional electroporation, the transduction efficiency of transposon system based on Sleeping Beauty system or PiggyBac transposon was significantly improved. The combination of nucleofector transfection instrument and SB Sleeping Beauty transposon system has been reported [Davies J K., et al. Combining CD19 redirection and alloanergization to generate tumor-specific human T cells for allogeneic cell therapy of B-cell malignancies. Cancer Res, 2010, 70(10): OF1-10.], and high transduction efficiency and site-directed integration of target genes can be achieved by this method. In one embodiment of the invention, the transduction method of a T lymphocyte modified by a chimeric antigen receptor gene is a transduction method based on a virus such as a retrovirus or a lentivirus. The method has the advantages of high transduction efficiency and stable expression of exogenous gene, and the time for in vitro culturing T lymphocytes to clinical level can be shorten. The transduced nucleic acid is expressed on the surface of the transgenic T lymphocytes by transcription, translation. In vitro cytotoxicity assay performed on various cultured tumor cells demonstrated that the immune effector cells of the present invention have highly specific tumor cell killing effects (also known as cytotoxicity). Therefore, the nucleic acid encoding a chimeric antigen receptor protein of the present invention, a plasmid comprising the nucleic acid, a virus comprising the plasmid, and a transgenic immune effector cells transfected with the nucleic acid, plasmid or virus described above can be effectively used in tumor immunotherapy.

The immune cells of the present invention may also carry exogenous encoding sequences for cytokines, including but not limited to IL-12, IL-15 or IL-21. These cytokines have immunomodulatory or antitumor activity, enhance the function of effector T cells and activated NK cells, or directly exert anti-tumor effects. Therefore, those skilled in the art will understand that the use of these cytokines will help the immune cells to function better.

In addition to the chimeric antigen receptor described above, the immune cells of the present invention may also express another chimeric antigen receptor, which does not contain CD3ζ, but contains intracellular signaling domain of CD28 and intracellular signal domain of CD137, or a combination of both.

The immune cells of the present invention may also express chemokine receptors; the chemokine receptors include, but are not limited to, CCR2. A skilled person will understand that the CCR2 chemokine receptor can competitively bind CCR2 in the body and is beneficial for blocking the metastasis of the tumor.

The immune cells of the present invention may also express siRNAs that can reduce PD-1 expression or PD-L1-blocking proteins. A skilled person will understand that competitive blocking of the interaction between PD-L1 and its receptor PD-1 will facilitate the recovery of anti-tumor T-cell responses, thereby inhibiting tumor growth.

The immune cells of the present invention may also express a safety switch; preferably, the safety switch includes iCaspase-9, Truancated EGFR or RQR8.

Immunoconjugate

In the present invention, a multifunctional immunoconjugate is also provided, comprising the antibodies described herein and further comprising at least one functional molecule of other type. The functional molecule is selected from, but not limited to, a molecule that targets a tumor surface marker, a tumor-suppressing molecule, a molecule that targets a surface marker of an immune cell, or a detectable label. The antibody and the functional molecule may form a conjugate by covalent attachment, coupling, attachment, cross-linking, or the like.

As a preferred mode, the immunoconjugate may comprise an antibody of the invention and at least one molecule that targets a tumor surface marker or a tumor-suppressing molecule. The tumor-suppressing molecule may be anti-tumor cytokines or anti-tumor toxins. Preferably, the cytokines include but are not limited to IL-12, IL-15, IFN-beta, TNF-alpha. The molecules that target tumor surface markers, for example, can act synergistically with the antibodies of the invention to more precisely target tumor cells.

As a preferred mode, the immunoconjugate may comprise an antibody of the present invention and a detectable label. Such detectable labels include, but are not limited to, fluorescent labels, chromogenic labels such as enzymes, prosthetic groups, fluorescent materials, luminescent materials, bioluminescent materials, radioactive materials, positron-emitting metals and non-radioactive paramagnetic metal ion. More than one marker can also be included. The label used to label the antibody for the purpose of detection and/or analysis and/or diagnosis depends on the used particular detection/analysis/diagnosis technique and/or method, eg, immunohistochemical staining (tissue) samples, flow cytometry, and the like. Suitable labels for detection/analysis/diagnosis techniques and/or methods known in the art are well known to those skilled in the art.

As a preferred mode, the immunoconjugate may comprise an antibody of the invention as well as a molecule that targets a surface marker of an immune cell. The molecule that targets surface markers of immune cells can recognize immune cells and carry the antibodies of the invention to the immune cells, so that the antibodies of the invention can target the immune cells to the tumor cells and thus trigger immunocyte for specifically killing tumor.

As a means of chemically generating an immunoconjugate by conjugation, either directly or indirectly (eg, by a linker), the immunoconjugate can be produced as a fusion protein comprising an antibody of the invention and other suitable proteins. The fusion protein can be produced by a method known in the art, for example recombinantly produced by constructing and subsequently expressing the nucleic acid molecule which comprises the nucleotide sequence encoding the antibody in frame with a nucleotide sequence encoding a suitable label.

In another aspect of the invention, a nucleic acid molecule encoding at least one antibody of the invention, a functional variant, or an immunoconjugate thereof is provided. Once obtaining the relevant sequence, the recombination method can be used to obtain the relevant sequence in large quantities. This is usually done by cloning it into a vector, transferring it to a cell, and then isolating the relevant sequence from the proliferating host cells by conventional methods.

The present invention also relates to vectors comprising the appropriate DNA sequences described above as well as appropriate promoters or control sequences. These vectors can be used to transform an appropriate host cell to enable expression of the protein. The host cell may be a prokaryotic cell, such as a bacterial cell; or a lower eukaryotic cell, such as a yeast cell; or a higher eukaryotic cell, such as a mammalian cell.

Pharmaceutical Composition

The antibodies, immunoconjugates comprising the antibodies, and genetically modified immune cells of the present invention can be used in the preparation of a pharmaceutical composition or diagnostic reagent. In addition to an effective amount of the antibody, immunological conjugate, or immune cell, the composition may further comprise a pharmaceutically acceptable carrier. The term "pharmaceutically acceptable" means that when the molecular entities and compositions are properly administered to animals or humans, they do not cause adverse, allergic or other untoward reactions.

Specific examples of some of the substances which may be used as pharmaceutically acceptable carriers or components thereof are sugars, such as lactose, dextrose and sucrose; starches, such as corn starch and potato starch; cellulose and its derivatives, such as carboxymethylcellulose sodium, ethylcellulose and methylcellulose; gum tragacanth; malt; gelatin; talc; solid lubricants such as stearic acid and magnesium stearate; calcium sulfate; vegetable oils, such as peanut oil, cottonseed oil, sesame oil, olive oil, corn oil and cocoa butter; polyhydric alcohols such as propylene glycol, glycerin, sorbitol, mannitol and polyethylene glycol; alginic acid; emulsifiers such as Tween®; wetting agents such as sodium lauryl sulfate; coloring agents; flavoring agents; tablets, stabilizers; antioxidants; preservatives; pyrogen-free water; isotonic saline solutions; and phosphate buffers and the like.

The composition of the present invention can be prepared into various dosage forms as needed, and the dosage to be administered to a patient can be determined by a physician according to factors, such as type, age, body weight, and general disease condition of a patient, mode of administration, and the like. For example, injection or other treatment may be used.

The present invention is further described below with reference to specific embodiments. It should be understood that these examples are only for illustrating the present invention and are not intended to limit the scope of the present invention. Experimental procedures in the following examples where no specific conditions are indicated are generally carried out in accordance with the conditions described in customary conditions such as those compiled by J. Sambrook et al., Molecular Cloning Experiments Guide, Third Edition, Science Press, 2002, or according to the manufacturer Suggested conditions.

Example 1. Construction of Cell Lines Stably Expressing Mesothelin 1.1 Construction of Plasmid Vector The vector system used in this example belongs to the third generation of self-inactivating lentiviral vector system. The system has three plasmids, packaging plasmid psPAX2 encoding protein Gag/Pol, encoding Rev protein; envelope plasmid PMD2.G encoding VSV-G protein; and recombinant plasmid pWPT-MSLN encoding the extracellular and transmembrane region of the target gene human mesothelin based on empty vector pWPT (purchased from Addgene).

According to GenBank Accession No. NM_005823, the target gene fragment (SEQ ID NO: 1 (nucleotide), 2 (amino acid)) containing signal peptide, Flag tag, extracellular domain and transmembrane region of human mesothelin was synthesized using a gene synthesis method based on bridge-PCR. PCR amplification was performed by primer pairs pWmslnF (SEQ ID NO: 3, GCTTACGCGTC-CTAGCGCTACCGGTCGCCACCATGAGGGCCTG-GATC) and pWmslnR (SEQ ID NO: 4, CGAGGTCGAC CTAGGCCAGGGTGGAGGCTAGGAGCAGTGCCAG-GACGG) under the following conditions: pre-denaturation: 94° C. for 4 min; denaturation: 94° C. for 30 s; annealing: 58° C. for 30 s; extension: 68° C. for 80 s; 30 cycles. The theoretical size of the obtained fragment was 1113 bp. The amplification product was confirmed by agarose electrophoresis and consistent with the theoretical size. MluI and SalI restriction sites were introduced upstream and downstream to the open reading frame. The target gene obtained above was double-digested with MluI and SalI and ligated into the same double-digested pWPT vector to construct a successful lentiviral vector pWPT-MSLN. The constructed vector was identified by MluI and SalI digestion and sequenced correctly, which was ready for lentivirus packaging.

1.2 Plasmid Transfecting 293T Cells for Packaging Lentivirus 293T cells (ATCC: CRL-11268) cultured at passage 6 to passage 10 were seeded at a density of $6 \times 10^6$ in 10 cm dishes and cultured overnight at 37° C. in 5% $CO_2$ for transfection. The medium was DMEM (Invitrogen) containing 10% fetal bovine serum (Sigma). And the next day, the medium was changed to serum-free DMEM about 2 hours prior to transfection.

Transfection steps were as follows:

1) 5 μg of target gene plasmid pWPT-MSLN was solved into 500 μl of MillQ water with 7.5 μg of packaging plasmid PAX2 and 2.5 μg of envelope plasmid pMD2.G, respectively, and mixed, 2) 62 μL of 2.5 M $CaCl_2$ (Sigma) was added dropwise and mixed at 1200 rpm/min vortex, 3) Finally, 500 μL of 2×HBS (280 mM NaCl, 10 mM KCl, 1.5 mM $Na_2HPO_4$, 12 mM glucose, 50 mM Hepes (Sigma), pH 7.05, and sterilized through 0.22 μM filter) was added dropwise and mixed by shaking at 1200 rpm/min for 10 s, 4) Immediately added to the culture dish, gently shake at 37° C., 5% $CO_2$, cultured for 4~6 h, replaced with DMEM containing 10% fetal bovine serum.

After 48 or 72 hours of transfection, cell debris was removed by centrifugation and the virus was collected by filtration through a 0.45 μm filter (Millipore).

1.3 Recombinant Lentivirus Infecting PANC-1 Cells

The collected virus solution was concentrated and titrated, and cells PANC-1 (purchased from the ATCC) plated in 6 cm plate were infected. Three days after infection, cells were harvested, part of mixed clones were taken, and lysed with cell lysis liquid. And then, 40 μg of cell protein was subjected to SDS-PAGE gel electrophoresis followed by immunoblotting and staining with mouse anti-Flag-tag antibody. After washing with PBS, the protein was incubated with horseradish peroxidase-labeled goat anti-mouse antibody, washed and finally developed with ECL reagent. Western blot results showed that a band with a molecular weight of about 38 kDa was detected in PANC-1 cells infected with human mesothelin MSLN (i.e., PANC-1-MSLN), while no corresponding band was detected in uninfected empty cells. Remaining cells were expanded, frozen and stored for later experiments.

Example 2. Preparation of Human Mesothelin Antigen

According to GenBank Accession No. NM_005823, the gene fragment of human mesothelin (positions 88-942 of SEQ ID NO: 1 (nucleotide), positions 30-314 of SEQ ID NO: 12 (amino acid)) were synthesized using a gene synthesis method based on bridge-PCR, and PCR amplification was performed. The amplified product was inserted into plasmid vector pCMV-V5 (the vector has 6×His tag fused and expressed downstream to the multiple cloning site, purchased from Shanghai Rui Jin Biotechnology Co., Ltd.) by NheI/BglII, and transformed into host strain TOP10. Positive clones were picked out, identified by PCR and confirmed by sequencing to obtain recombinant expression plasmid V5-MSLN.

The above expression plasmids were transfected into well-growing HEK-293F cells and cultured continuously at 37° C., 5% $CO_2$, 12.5 rpm on a shaker for 7 days and centrifuged at 4000 rpm for 10 min, the pellets were removed, the supernatant was collected and filtered through a 0.45 μm membrane filter, the processes sample was purified with HisTrap (from GE) affinity chromatography column to finally obtain purified human mesothelin protein, and the identification results are shown in FIG. 1.

Example 3. Screening of Single Chain Antibody Against Human Mesothelin 3.1 Screening of Human Mesothelin-Specific Binding Antibodies Based on Phage Display Using phage display technology, human mesothelin specific antibody was screened from the all-human natural antibodies library. For this purpose, glycerol bacteria (purchased from Shanghai Rui Jin Biotechnology Co., Ltd.) from the natural library of phage-displayed all-human single-chain antibody were inoculated in 400 ml of 2×YT/ampicillin medium so that the cell density reached $OD_{600}$=0.1, and incubated at 37° C. and 200 rpm until cell density reached $OD_{600}$=0.5. Cells were infected with $10^{12}$ pfu of M13KO7 helper phage (purchased from Invitrogen) and incubated at 30° C. and 50 rpm for 30 minutes. After 50 mg/L kanamycin was added and shaking-culture was performed at 37° C. and 200 rpm for 30 minutes, the pellet was separated by centrifugation (15 minutes, 1600×g, 4° C.) and resuspended in 400 ml of 2×YT/Penicillin/kanamycin medium and shaken for 16 hours at 37° C. and 200 rpm. Finally, the pellet was separated by centrifugation (5000 rpm, 4° C. for 20 minutes) and discarded. The supernatant was filtered through a 0.45 μm filter and ¼ volume of 20% (w/v) PEG 8000, 2.5 M NaCl solution was added and incubated in an ice bath for 1 hour to precipitate bacteriophage pellets. The pellet was then precipitated by centrifugation (20 min, 8000×g, 4° C.) and the supernatant discarded. The phage were resuspended in 25 ml of prechilled PBS (137 mM NaCl, 2.7 mM KCl, 8 mM $Na_2HPO_4$, 2 mM $KH_2PO_4$) and centrifuged (5 minutes, 20000×g, 4° C.). ¼ volume of 20% (w/v) PEG8000, 2.5 M NaCl solution was added to the supernatant and incubated in an ice bath for 30 minutes to precipitate phage particles again. The pellets were centrifuged (30 min, 20000×g, 4° C.) and the phage pellets were resuspended in 2 ml of prechilled PBS again, kept on ice for 30 min and centrifuged (30 min, 17000×g, 4° C.). Supernatants were mixed with 4% (w/v) BSA in PBS at 1:1, placed on a rotary mixer and incubated for 30 minutes at room temperature before being directly used for screening.

Using the above phage antibody library, four rounds of directional screening were performed on biotinylated human mesothelin recombinant protein with the following scheme: The phage antibody library was incubated with biotin-labeled antigen mesothelin at room temperature for 2 hours and then incubated with streptavidin magnetic beads MyOne C1 (from Invitrogen) blocked with 2% (w/v) BSA (bovine serum albumin) at room temperature for 30 minutes. The beads were then washed with PBST (containing 0.1% Tween-20) buffer to remove phages which were not specifically bound or with weak binding capacities. Strongly-binding phages were then eluted from magnetic beads with glycine-HCl (pH 2.2), neutralized with Tris neutralizing solution (pH 9.1), and used to infect *E. coli* ER2738 in the mid-logarithmic growth phase and for the next round of screening. In the four rounds of screening, the beads were used in an amount of 50 μl, 20 μl, 10 μl and 10 μl, and the concentrations of biotin-labeled human mesothelin were 100 nM, 10 nM, 5 nM and 1 nM, respectively, and the time for PBST-washing was 10, 10, 15 and 20, respectively.

3.2 Identification of Human Mesothelin-Specific Binding Antibodies 96 clones were randomly selected in the clones obtained from the fourth round of screening and their binding capability to human mesothelin was analyzed by single phage ELISA (enzyme-linked immunosorbent assay). For this purpose, each single colony was inoculated in 300 μl of 2×YT/ampicillin medium (containing 2% glucose) in a 96-well deep-well plate and cultured with shaking at 37° C. and 250 rpm for 16 hours. 20 μl of culture was inoculated into 500 μl of 2×YT/ampicillin medium (containing 0.1% glucose) and shaken at 37° C. and 250 rpm for 1.5 hours. To prepare the helper phage solution, 75 μl of M13KO7 (titer of $3\times10^{12}$ pfu/ml) was taken and mixed into 15 ml of 2×YT medium and added into a culture plate at 50 μl/well, and incubated at 37° C. and 150 rpm for 30 minutes. And then prepared kanamycin solution (180 μl of 50 mg/ml kanamycin was taken and added into 15 ml of 2×YT medium) was added at 50 μl/well and incubated with shaking for 16 hours at 37° C. and 250 rpm. Finally, cells were precipitated by centrifugation (30 mins, 5000×g, 4° C.) and the supernatant was transferred to a new 96-well deep-well plate.

Figure 2:
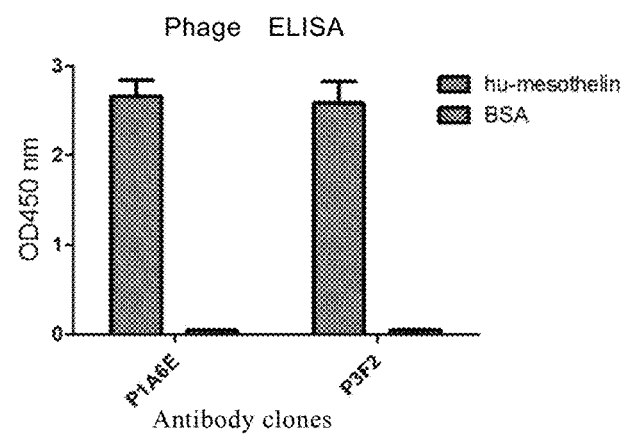
FIG. 2. Binding of two different single chain antibodies P1A6E and P3F2 to human mesothelin and BSA detected by ELISA.

For single phage ELISA, 100 ng/well of antigen human mesothelin and negative control protein BSA (100 μl/well) were used in a 96-well MediSorp ELISA plate (purchased from Nunc) and coated overnight at 4° C. Each well was blocked with PBST containing 2% BSA (w/v). The wells were then washed with PBST for three times and PBST was discarded. Then, each phage solution prepared above was added into each well of the plate at 100 µl/well. After incubated at 37° C. for 2 hours, the plate was washed for three times with PBST. To detect bound phage, anti-M13 antibody peroxide dismutase conjugate (purchased from GE Healthcare) was diluted at 1:5000 in PBST and 100 µl was taken and added into each well. After incubated at 37° C. for 1 hour, the wells were rinsed for three times with PBST and then rinsed for three times with PBS. Finally, 50 µl of TMB substrate was pipetted into the wells and developed for 10 minutes at room temperature, followed by addition of 50 µl of 2M $H_2SO_4$ per well to quench the color reaction. Extinction values were measured at 450 nm with an enzyme-linked immunosorbent (Bio-Rad). Two different single chain antibodies P1A6E (SEQ ID NO: 5 (nucleotide), 6 (amino acid)) and P3F2 (SEQ ID NO: 7 (nucleotide), 8 (amino acid)) were observed with sequencing analysis, which exhibited significantly stronger binding signal to human mesothelin (hu-mesothelin) in ELISA assay, while not binding to BSA (FIG. 2).

(nucleotide)
SEQ ID NO: 5
caggtacagctggaacagtcaggtctaggactggtgaagccctcgcag accctctctctcacctgtgccatctccggggacactgtctctagcgac agtgctgcttggaactggatcaggcagtccccatcgagaggccttgag tggctgggaaggacatactacaggtccaagtggtttaatgattatgca gtatctgtgaaaggtcgaataaccatcaactcagacacatccaagaac cagttctccctgcagttgaactctgtgactcccgaggacacggctgtg tattattgtgcaagaagtaatagttactactactacgctatggacgtc tggggccaaggcaccctggtcaccgtctcgagtggtggaggcggttca ggcggaggtggtctggcggtggcggatcgcaggctgtgctgactcag ccgtcttccctctctgcatctcctggagcatcagccagtctcacctgc accttgcgcagtggcatcaatgttggtatctacaggatatactggtac caacagaggccagggagtcctccccagattctcctgacttacaaatca gactcagataagtaccagggctctggagtccccagtcgcttctctgga tccaaagatgcttcggccaatgcagggattttactcatctctgggctc cagtctgaagatgaggctgactattactgcatgatttggcacagcggc ggttgggtgttcggcggagggaccaaggtcaccgtcctaggt (amino acid)
SEQ ID NO: 6
QVQLEQSGLGLVKPSQTLSLTCAISGDTVSSDSAAWNWIRQSPSRGLE

WLGRTYYRSKWFNDYAVSVKGRITINSDTSKNQFSLQLNSVTPEDTAV

YYCARSNSYYYYAMDVWGQGTLVTVSS GGGGS GGGGS GGGGS QAVLTQ

PSSLSASPGASASLTCTLRSGINVGIYRIYWYQQRPGSPPQILLTYKS

DSDKYQGSGVPSRFSGSKDASANAGILLISGLQSEDEADYYCMIWHSG

GWVFGGGTKVTLG

Wherein the amino acid sequence of the heavy chain variable region is shown in positions 1 to 123 of SEQ ID NO: 6 and the amino acid sequence of the light chain variable region is shown in positions 139 to 254 of SEQ ID NO: 6.

Wherein the amino acid sequence of light chain CDR1 is TLRSGINVGIYRIY (SEQ ID NO: 51), the amino acid sequence of light chain CDR2 is YKSDSDKYQGS (SEQ ID NO: 52), the amino acid sequence of light chain CDR3 is MIWHSGGWV (SEQ ID NO: 53); the amino acid sequence of heavy chain CDR1 is GDTVSSDSAAWN (SEQ ID NO: 54), the amino acid sequence of heavy chain CDR2 is RTYYRSKWFNDYAVSVKG (SEQ ID NO: 55), and the amino acid sequence of heavy chain CDR3 is SNSYYYYAMDV (SEQ ID NO: 56).

(nucleotide)
SEQ ID NO: 7
cagatgcagctagtgcagtctggggctgaggtgaagaagcctgggc ctcagtgaaggtttcctgcaaggcatctggatacaccttcaccagct actatatgcactgggtgcgacaggcccctggacaagggcttgagtgg atgggaataatcaaccctagtggtggtagcacaagctacgcacagaa gttccaggcagagtcaccatgaccagggacacgtccacgagcacag tctacatggagctgagcagcctgagatctgaggacacggccgtgtat tactgtgcgagtagtcggagtgggactacggtggtaaatcatgatgc ttttgatatctgggggaaagggaccacggtcaccgtctcgagtggtg gaggcggttcaggcggaggtggttctggcggtggcggatcggacatc cagttgacccagtctccatcctccctgtctgcgtctgtaggagacag agtcaccatcacttgccgggcaagccaggtcattagccgtgctttag cctggtatcaacaaacaccagggaaacctcctaaactcctgatctat gatgcctccaatttgcagagtggggtcccatcaaggttcagcggcag tggatctgggacagatttcactctcaccatcagccgcctgcagcctg aagatttttgcaacttattactgtcaacagtttaatagttaccctctc actttcggcggagggaccaagctggagatcaaacgt (amino acid)
SEQ ID NO: 8
QMQLVQSGAEVKKPGASVKVSCKASGYTFTSYYMHWVRQAPGQGLEW

MGIINPSGGSTSYAQKFQGRVTMTRDTSTSTVYMELSSLRSEDTAVY

YCASSRSGTTVVNHDAFDIWGKGTTVTVSS GGGGS GGGGS GGGGS DI

QLTQSPSSLSASVGDRVTITCRASQVISRALAWYQQTPGKPPKLLIY

DASNLQSGVPSRFSGSGSGTDFTLTISRLQPEDFATYYCQQFNSYPL

TFGGGTKLEIKR

Wherein, the amino acid sequence of the heavy chain variable region is shown in positions 1 to 124 of SEQ ID NO: 8; the amino acid sequence of the light chain variable region is shown in positions 140-247 of SEQ ID NO: 8.

Wherein the amino acid sequence of light chain CDR1 is RASQVISRALA (SEQ ID NO: 57), the amino acid sequence of light chain CDR2 is DASNLQS (SEQ ID NO: 58), the amino acid sequence of light chain CDR3 is QQFNSYPLT (SEQ ID NO: 59); the amino acid sequence of heavy chain CDR1 is GYTFTSYYMH (SEQ ID NO: 60), the amino acid sequence of heavy chain CDR2 is IINPSGGSTSYAQKFQG (SEQ ID NO: 61) and the amino acid sequence of heavy chain CDR3 is SRSGTTVVNH-DAFDI (SEQ ID NO: 62).

Example 4. Preparation of Single Chain Antibody and Monoclonal Antibody

4.1 Preparation of Single Chain Antibody Against Human Mesothelin scFv-P1A6E fragment was amplified from the resulting clones using primer pair V5-P1A6E-F (SEQ ID NO: 9) and V5-P1A6E-R (SEQ ID NO: 10); scFv-P3F2 fragment was amplified using primer pair V5-P3F2-F (SEQ ID NO: 11) and V5-P3F2-R (SEQ ID NO: 12), digested by NheI/BamHI restriction enzyme, connected to NheI/BamHI double-digested vector plasmid pCMV-V5-Fc (in the vector, Fc fragment of human antibody IgG1 was fused downstream to multiple cloning sites, hereinafter referred to as V5-Fc, purchased from Shanghai Rui Jin Biotech Co., Ltd.) with T4 DNA ligase, and transformed into host strain TOP10. Clones were picked up, and positive clones were identified by PCR and confirmed by sequencing to obtain eukaryotic expression plasmids, V5-scFv-P1A6E-Fc and V5-scFv-P3F2-Fc, respectively.

```
SEQ ID NO: 9:
ACAGTGCTAGCACAGGTACAGCTGGAACAG;

SEQ ID NO: 10:
TTGTCGGATCCACCTAGGACGGTGACC;

SEQ ID NO: 11:
ACAGTGCTAGCACAGATGCAGCTAGTGC;

SEQ ID NO: 12:
TTGTCGGATCCACGTTTGATCTCCAGC.
```

Figure 3:
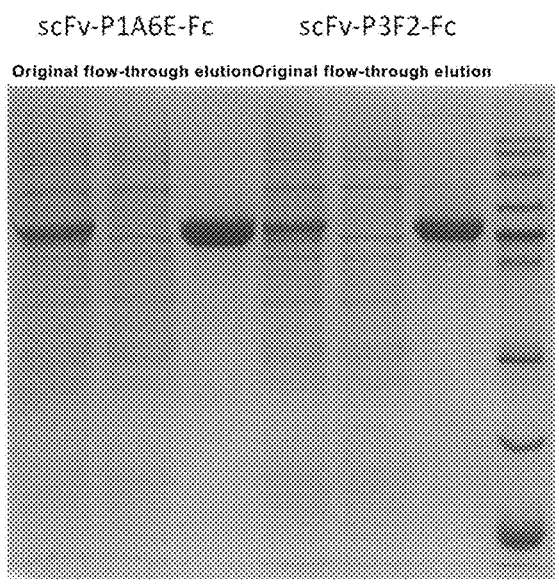
FIG. 3. Electrophoresis of purified SDS-PAGE of anti-human mesothelin antibodies.

The above expression plasmids were transfected into well-growing HEK-293F cells respectively, cultured at 37° C., 5% $CO_2$, 125 rpm on a shaker continuously for 7 days, centrifuged at 4000 rpm for 10 min. Pellets were removed, and the supernatant was collected and filtered with 0.45 μm membrane. The processed sample was affinity-purified with protein A (from GE) affinity column to finally obtain the purified antibody-Fc fusion proteins scFv-P1A6E-Fc and scFv-P3F2-Fc. The identification results are shown in FIG. 3.

4.2 Preparation of Monoclonal Antibody Against Human Mesothelin

In this example, the monoclonal antibody was expressed using a two-plasmid system. The gene of antibody heavy chain variable region shall be constructed into pIH plasmid containing human IgG1 CH gene, and the gene of antibody light chain variable region be constructed into PIK plasmid containing human IgG CL gene (plasmid purchased from Shanghai Rui Jin Biotechnology Co., Ltd.).

VH-P1A6E fragment was amplified from the template plasmid V5-scFv-P1A6E-Fc using primer pair P1A6E-HF (SEQ ID NO: 13, gcctttcctggtttcctgtctcaggtacagctgg aacagtc) and P1A6E-HR (SEQ ID NO: 14, GATGGGCCCTTG-GTGGAGGCACTCGAGACGGTGACCAG). HF1 fragment was amplified from the template plasmid pIH using primer pair HF1F (SEQ ID NO: 15, ggctaactagagaaccccactgc) and HF1R (SEQ ID NO: 16, AGACAGGAAAC-CAGGAAAGGC); and HF3 fragment was amplified from the template plasmid pIH primers HF3F (SEQ ID NO: 17, gcctccaccaagggcccatc) and HF3R (SEQ ID NO: 18, gacaatcttagcgcagaagtc). The three fragments were mixed at equimolar ratio, and then splicing-PCR was performed. Fragments were recovered by restriction endonuclease NheI/NotI double digestion and connected into NheI/NotI double-digested vector plasmid pIH with T4 DNA ligase and transformed into host strain TOP10. Clones were picked out and the positive clones were identified by PCR and confirmed by sequencing to obtain pIH-P1A6E eukaryotic expression plasmid. pIH-P3F2 eukaryotic expression plasmid was also obtained in the same manner.

To obtain pIK-P1A6E eukaryotic expression plasmid, VL1-P1A6E fragment was obtained from the template plasmid V5-scFv-P1A6E-Fc using the primer pair P1A6E-LF (SEQ ID NO: 19, ctttggtttccaggtgcaagatgtcaggctgtgct-gactcag) and P1A6E-LR (SEQ ID NO: 20, GAAGACA-GATGGTGCAGCCACCGTACCTAGGACGGTGAC-CTTG); LF1 fragment was amplified from the template plasmid pIK using the primer pair LF1F (SEQ ID NO: 21, ggctaactagagaacccactgc) and LF1R (SEQ ID NO: 22, ACATCTTGCACCTGGAAACCAAAG); LF3 fragment was amplified from the template plasmid pIK using the primer pair LF3F (SEQ ID NO: 23, acggtggctgcaccatct-gtcttc) and LF3R (SEQ ID NO: 24, GACAATCT-TAGCGCAGAAGTC). The three fragments were mixed in equimolar ratio for splicing PCR. After the fragments were recovered, the fragments were digested with EcoRV/NotI restriction endonucleases and ligated in EcoRI/NotI double-digested vector plasmid pIK with T4 DNA ligase, and transformed into host strain TOP10. Clones were picked out and positive clones were identified by PCR and confirmed by sequencing. pIK-P3F2 eukaryotic expression plasmid was also obtained in the same manner.

Figure 4:
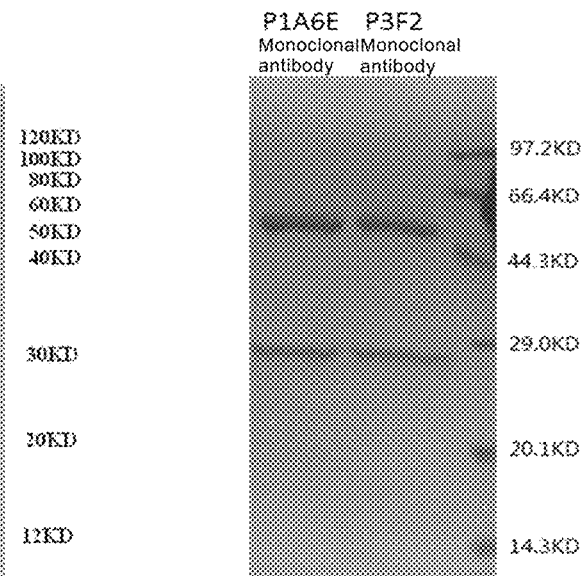
FIG. 4. SDS-PAGE electrophoresis of the monoclonal antibodies P1A6E and P3F2.

Expression plasmids pIH-P1A6E and pIK-P1A6E were equimolarly mixed, pIH-P3F2 and pIK-P3F2 were equimolarly mixed and transfected into well-growing HEK-293F cells respectively. The cells were cultured at 37° C., 5% $CO_2$, 125 rpm on a shaker continuously for 7 days, centrifuged at 4000 rpm for 10 min. Pellets were removed, and the supernatant was collected and filtered with 0.45 μm membrane. The processed sample was affinity-purified with protein A (from GE) affinity column to finally obtain the purified antibody P1A6E and P3F2. The identification results are shown in FIG. 4.

Example 5. Affinity of Antibody Against Human Mesothelin

To quantitatively analyze the binding of an antibody to human mesothelin, the affinity and kinetic parameters of single-chain antibody and monoclonal antibody of P1A6E and P3F2 were measured by capture method using Biacore T200 system (from GE). An anti-human IgG (Fc) antibody (purchased from GE) was coupled to carboxymethyl dextran surface of sensor chip CMS through primary amino with NHS/EDC coupling according to the manufacturer's instructions. Measurements were performed in 1×HBS-EP+ working buffer at 25° C., 30 μl/min, and regeneration condition was 3 M MgCl2, 10 μl/min for 30 seconds. In each round of the testing cycle, the antibody to be tested is firstly captured onto the chip. Analyte (human mesothelin) of a certain concentration flowed over the chip surface. Due to the produced SPR signal, the interaction between human mesothelin and the captured antibody can be detected. The detected signal is defined as resonance unit (RU), which was plotted vs time (second) to obtain the corresponding binding curve and dissociation curve. In different test cycles, concentrations of human mesothelin were 10 nM, 20 nM, 40 nM, 80 nM and 160 nM, respectively. The resulting curves were evaluated using Biacore T200 evaluation software and the affinity KD values were calculated. FIG. 5 and FIG. 6 show kinetic curves of the monoclonal antibodies P1A6E and P3F2, in a Biacore Affinity Assay, respectively. The binding data for single-chain antibody and monoclonal antibody of P1A6E and P3F2 to human mesothelin are summarized in Table 1.

TABLE 1

Affinity parameters of single chain antibodies and monoclonal antibodies of P1A6E and P3F2 to human mesothelin

| Sample of antibody | ka (1/Ms) | kd (1/s) | KD (M) |
|---|---|---|---|
| P1A6E monoclonal antibody | 2.88E+05 | 1.16E−03 | 4.04E−09 |
| P3F2 monoclonal antibody | 1.10E+05 | 7.89E−04 | 7.17E−09 |
| P1A6E single chain antibody | 8.25E+04 | 1.56E−03 | 1.89E−08 |
| P3F2 single chain antibod | 5.77E+04 | 9.35E−04 | 1.62E−08 |

Example 6. Cell-Binding Properties of Antibody to Human Mesothelin (Single-Chain Antibody and Monoclonal Antibody)

Each of antibodies scFv-P1A6E-Fc and scFv-P3F2-Fc was analyzed for binding ability to mesothelin at cell surface by Fluorescence Activated Cell Sorter (FACS) (Guava 8HT, supplied by Millipore).

Specific methods are as follows:

1) inoculating PANC-1-MSLN and PANC-1 in logarithmic growth phase into a 6 cm dish respectively at inoculation cell density of about 90%, and incubating overnight at 37° C. in an incubator.

2) digesting cells with 10 mM EDTA, collecting cells through centrifugation at 200 g×5 mins, and resuspending cells in 1% phosphate buffered saline (NBS PBS) containing calf serum at 1×10⁶ to 1×10⁷/mL into a flow-specific tube in an amount of 100 μl per tube.

3) centrifuging at 200 g×5 min, and discarding the supernatant.

4) antibodies P1A6E and P3F2 to be tested were added into the two experimental groups, respectively, adding antibodies ss and C10 (purchased from Shanghai Rui Jin Biotechnology Co., Ltd.) were added into two positive control groups added as positive controls, and another control group is PBS blank control without antibody. The final concentration of each antibody was 20 μg/ml. 100 μl was added to each tube, and incubated in an ice bath for 45 minutes.

5). Adding 2 ml of 1% NBS PBS to each tube and centrifuging at 200 g×5 min for two times.

6) Discarding the supernatant and adding goat anti-human antibody-FITC (Shanghai Karrie Biotech Co., Ltd.) at a dilution of 1:100 with 100 ul being added to each tube, incubating in an ice bath for 45 minutes.

7). Adding 2 ml of 1% NBS PBS into each tube, centrifuging at 200 g×5 min for two times.

8) Discarding the supernatant, resuspending in 300 ul of 1% NBS PBS and detecting by flow cytometry.

9) Analyzing the data using flow cytometry data analysis software Flowjo7.6.

Flow cytometry results showed that four antibodies, P1A6E and P3F2, as well as control antibodies SS and C10, either in single-chain antibody format (FIG. 7) or in monoclonal full antibody format (FIG. 8, fluorescence peak of PANC-1-MSLN cells was significantly different from that of blank control (PBS) (FIG. 7B, FIG. 8B), while no significant difference from PANC-1 cells (FIG. 7A, FIG. 8A)), can specifically recognize PANC-1-MSLN cells stably expressing human mesothelin, but do not bind to human mesothelin-negative PANC-1 cells, indicating that the four antibodies could specifically recognize human mesothelin. The fluorescence peaks of antibodies P1A6E and P3F2 were significantly stronger than those of control antibodies SS and C10, indicating that the binding efficiencies of P1A6E and P3F2 to PANC-1-MSLN cells are higher than those of SS and C10.

Example 7. Preparation of CAR T Containing Antibody to Human Mesothelin

To construct a chimeric antigen receptor, the connection order of the parts of the chimeric antigen receptor exemplified in the present invention is shown in Table 2.

TABLE 2

| Chimeric antigen receptor | Extracellular binding region - transmembrane region - intracellular signal region 1 - intracellular signal region 2 and the like | Description |
|---|---|---|
| P1A6E-δZ | scFv(MSLN)-CD8-CD3δzeta | Negative control |
| P1A6E-Z | scFv(MSLN)-CD8-CD3 zeta | $1^{st}$ generation |
| P1A6E-BBZ | scFv(MSLN)-CD8-CD137-CD3 zeta | $2^{nd}$ generation |
| P1A6E-28Z | scFv(MSLN)-CD28a-CD28b-CD3 zeta | $2^{nd}$ generation |
| P1A6E-28BBZ | scFv(MSLN)-CD28a-CD28b-CD137-CD3 zeta | $3^{rd}$ generation |
| P3F2-δZ | scFv(MSLN)-CD8-CD3δzeta | Negative control |
| P3F2-Z | scFv(MSLN)-CD8-CD3 zeta | $1^{st}$ generation |
| P3F2-BBZ | scFv(MSLN)-CD8-CD137-CD3 zeta | $2^{nd}$ generation |
| P3F2-28Z | scFv(MSLN)-CD28a-CD28b-CD3 zeta | $2^{nd}$ generation |
| P3F2-28BBZ | scFv(MSLN)-CD28a-CD28b-CD137-CD3 zeta | $3^{rd}$ generation |

Note:
CD28a represents the transmembrane region of CD28 molecule and CD28b represents the intracellular signaling region of CD28 molecule.

The lentiviral plasmid vector system used in the present example belongs to lentiviral 4-plasmid system of the third generation, which has 4 plasmids, namely, envelope plasmid pCMV-VSV-G encoding VSV-G protein (from addgene), packaging plasmid pRSV-REV encoding Rev protein (from addgene); pMDLg/pRRE encoding Gal and Pol (from addgene) and the recombinant expression vector encoding the gene of interest CAR based on empty vector pRRLSIN-cPPT.PGK-GFP.WPRE (from addgene). For the promoter in all vectors of CAR gene, elongation factor-1α (EF-1α) of the vector disclosed in 201310164725.X was used. Specific construction method is as follows:

(1) Obtaining Promoter Fragment: a fragment with the promoter EF-1α was amplified by PCR using the vector pWPT-eGFP-F2A-CAR, primers pwpxlF (SEQ ID NO: 25, 5'-gcaggggaaagaatagtaga ca-3') and pWPT-MluIR (SEQ ID NO: 26, 5'-aggccagcggcaggagcaaggcggtcactggta aggccatg-gtggcgaccggtagc-3').

(2) Obtaining fragment of target CAR: P1A6E part and P3F2 part of the target CAR fragment was amplified using the above obtained V5-scFv-P1A6E-Fc and V5-scFv-P3F2-Fc as templates and using primers P1A6E-F (SEQ ID NO: 27, 5'-ctcctgccgctggccttgctgctccacgccgccaggccgcaggtacagc tggaaca-3') and primer P1A6E-R (SEQ ID NO: 28, 5'-gcg-gcgctggcgtcgtggtacctaggacggtgacc-3'), primer P3F2-F (SEQ ID NO: 29, 5'ctcctgccgctggccttgctgctccacgccgccaggc-cgcagatgcagctagt gca-3') and P3F2-R (SEQ ID NO: 30, 5'gcggcgctggcgtcgtggtacgtttgatctccag-3').

(3) The first, second, third generation of consensus sequence and negative control sequence of CAR were obtained by PCR: fragments CD8-CD3δ zeta(δZ), CD8-CD3 zeta (Z), CD28a-CD28b-CD3 zeta (28Z) and CD28a-CD28b-CD137-CD3 zeta (28BBZ) sequences were obtained by using pWPT-eGFP-F2A-GPC3-δZ, pWPT-eGFP-F2A-GPC3-Z, pWPT-eGFP-F2A-GPC3-28Z and pWPT-eGFP-F2A-GPC3-28BBZ in 201310164725.X as templates and primer HF (SEQ ID NO: 63, 5'accacgacgccagcgccgcgaccac) and primer pwpxlR (SEQ ID NO: 64, 5'-tagcgtaaaaggag-caacatag), respectively.

(4) fragments of consensus sequence CD8-CD137-CD3 zeta (BBZ) were synthesized using a gene synthesis method based on bridge-PCR with reference to BBZ sequence in U.S. Pat. No. 8,911,993 B2 (COMPOSITIONS FOR TREATMENT OF CANCER).

(5) After the above obtained promoter fragment, target CAR fragments and fragments of consensus sequence CD8-CD3δ zeta(δZ), CD8-CD3 zeta(Z), CD8-CD137-CD3 zeta (BBZ), CD28a-CD28b-CD3 zeta(28Z) and CD28a-CD28b-CD137-CD3 zeta(28BBZ) were respectively routinely bridged, primers pwpxlF and pwpxlR were used for amplification to obtain fragments containing the EF-1α and target gene CAR and respectively referred to as:

P1A6E-δZ (SEQ ID NO: 31);
P1A6E-Z (SEQ ID NO: 32);
P1A6E-BBZ (SEQ ID NO: 33);
P1A6E-28Z (SEQ ID NO: 34);
P1A6E-28BBZ (SEQ ID NO: 35).
P3F2-δZ (SEQ ID NO: 36);
P3F2-Z (SEQ ID NO: 37);
P3F2-BBZ (SEQ ID NO: 38);
P3F2-28Z (SEQ ID NO: 39);
P3F2-28BBZ (SEQ ID NO: 40).

(6) The CAR fragment with the promoter and the target gene CAR obtained in the above step was double-digested with ClaI and SalI and ligated into the same digested vector pRRLSIN.cPPT.PGK-GFP.WPRE to construct a lentiviral vector expressing each chimeric antigen receptor. The successfully constructed vector was identified by Mlu and Sal digestion and confirmed by sequencing for lentivirus packaging.

The resulting vectors containing each target CAR are as follows:
pRRLSIN-EF1α-P1A6E-δZ;
pRRLSIN-EF1α-P1A6E-Z;
pRRLSIN-EF1α-P1A6E-BBZ;
pRRLSIN-EF1α-P1A6E-28Z;
pRRLSIN-EF1α-P1A6E-28BBZ;
pRRLSIN-EF1α-P3F2-δZ;
pRRLSIN-EF1α-P3F2-Z;
pRRLSIN-EF1α-P3F2-BBZ;
pRRLSIN-EF1α-P3F2-28Z;
pRRLSIN-EF1α-P3F2-28BB.

Through the above construction, 10 CAR polypeptide sequences can be obtained respectively, which are referred to as:

P1A6E-δZ (SEQ ID NO: 41);
P1A6E-Z (SEQ ID NO: 42);
P1A6E-BBZ (SEQ ID NO: 43);
P1A6E-28Z (SEQ ID NO: 44);
P1A6E-28BBZ (SEQ ID NO: 45).
P3F2-δZ (SEQ ID NO: 46);
P3F2-Z (SEQ ID NO: 47);
P3F2-BBZ (SEQ ID NO: 48);
P3F2-28Z (SEQ ID NO: 49);
P3F2-28BBZ (SEQ ID NO: 50).

Transfection of 293T by Plasmid for Packaging Lentivirus

HEK-293T cells (ATCC: CRL-11268) cultured at passage 6 to passage 10 were seeded at a density of $6 \times 10^6$ in 10 cm dishes and cultured overnight at 37° C. in 5% $CO_2$ for transfection. The medium was DMEM containing 10% fetal bovine serum.

Transfection steps are as follows:

Preparation of liquid A: dissolving 10 μg of desired gene plasmids pRRLSIN-cPPT.EF-1α-CAR (selected from pRRLSIN-EF1α-P1A6E-δZ, pRRLSIN-EF1α-P1A6E-Z, pRRLSIN-EF1α-P1A6E-BBZ, pRRLSIN-EF1α-P1A6E-28Z, pRRLSIN-EF1α-P1A6E-28BBZ, pRRLSIN-EF1α-P3F2-Z, pRRLSIN-EF1α-P3F2-BBZ, pRRLSIN-EF1α-P3F2-28Z, pRRLSIN-EF1α-P3F2-28BBZ) with 7.5 μg of packaging plasmid pMDLg RRE and pRSV-REV and 3 μg of envelope plasmid pCMV-VSV-G into 800 μL of serum-free DMEM medium and mixing well.

Preparation of liquid B: dissolving 60 μg PEI (polyethylenimine 1 μg/μl, purchased from Polysciences) in 800 μL serum-free DMEM medium, mixing gently and incubating at room temperature for 5 min.

Formation of transfection complex: adding liquid A into liquid B and gently mixing, vortexing or gently mixing immediately after addition, incubating at room temperature for 20 min.

Adding 1.6 ml of the transfection complex into HEK-293T cells dropwise, and after 4-5 h, changing to DMEM with 2% FBS for transfected 293T cells.

After 72 h of transfection, the virus was collected by filtration using a 0.45 μm filter and centrifuged at 28,000 rpm using a Beckman Optima L-100XP ultracentrifuge for 2 hours at 4° C. The supernatant was discarded and the resulting pellet was centrifuged at ⅒~1/50 stock solution of AIM-V medium (purchased from Invitrogen) and resuspend at 100 μL/tube in −80° C. for virus titration or infection of T lymphocytes.

Example 8. Infection of CTL Cells by Recombinant Lentivirus

Human peripheral blood mononuclear cells were obtained from healthy human peripheral blood by density gradient centrifugation (supplied by Shanghai Blood Center), and CTLs were obtained from peripheral blood mononuclear cells by negative sorting method using CTL magnetic beads (purchased from Stem Cell Technologies). Sorted CTL cells were subjected to flow cytometry to detect the purity of CTL cells. The positive rate of CTL cells ≥95% was appropriate for the next step. Cells were added in Quantum 007 lymphocyte medium (purchased from PAA) at a density of about $1 \times 10^6$/mL. Magnetic beads coated with anti-CD3 and CD28 antibodies (Invitrogen) were added in a 1:1 ratio of cells to magnetic beads, and recombinant human IL-2 (purchased from Shanghai Huaxin Biotechnology Co., Ltd.) at a final concentration of 300 U/mL was added for stimulation and culture for 24 h. And then CTL cells were infected with the above recombinant lentivirus at MOI≈5. The infected cells were passaged every other day at a density of 5×10$^5$/mL and recombinant human IL-2 at a final concentration of 300 U/mL was supplemented in the lymphocyte culture medium.

Infected CTL cells were detected by flow cytometry on day 8 of culture for the expression of different chimeric antigen receptors. Firstly, the infected CAR T cells were incubated with biotinylated human mesothelin recombinant protein for 1 h at 37° C., washed in D-PBS twice and then incubated with PE-labeled streptavidin for 40 min at 37° C. After washed with D-PBS for 3 times, the ratio of positive cells was determined by flow cytometry. Uninfected T lymphocytes was used as a negative control, the positive rates of virus-infected T cells expressing different chimeric antigen receptors are shown in Table 3. The positive rate results show that a certain positive rate of CAR$^+$T cells can be obtained by lentivirus infection.

TABLE 3

| CTL cells transfected by following CARs | Positive rate of CTL cells transfection |
|---|---|
| P1A6E-δZ (negative control) | 75% |
| P1A6E-Z | 58% |
| P1A6E-BBZ | 85% |
| P1A6E-28Z | 73% |
| P1A6E-28BBZ | 69% |
| P3F2-δZ (negative control) | 71% |
| P3F2-Z | 68% |
| P3F2-BBZ | 83% |
| P3F2-28Z | 86% |
| P3F2-28BBZ | 77% |

CTL cells were infected with viruses that had different chimeric antigen receptors packaged, respectively, and then subcultured at a cell density of 5×10$^5$/ml quaque die alterna, counted, and supplemented with IL-2 (final concentration of 300 U/ml). On the 11th day of culture, about 20~40 times of amplification was obtained, indicating that the CTL cells expressing different chimeric antigen receptors can be expanded in a certain amount in vitro, which ensures subsequent in vitro toxicity tests and in vivo experiments.

Example 9. In Vitro Toxicity Test of T Lymphocytes Expressing Chimeric Antigen Receptors In vitro toxicity experiments used the following materials:
Mesothelin-negative pancreatic cancer cell line (PANC-1) and PANC-1 (PANC-1-MSLN) cell line transfected with mesothelin gene as shown in Table 4 were used as target cells and effector cells were CTL cultured for 12 days in vitro, which were verified in Example 4 and detected chimeric antigen receptor-expression positive by FACS. Effective target ratios were 3:1, 1:1 and 1:3, respectively. The number of target cells was 10000/well, and effector cells corresponded to different effective target ratio. Each group had 5 replicate wells, average of 5 wells was calculated, and detection time was 18 h.

Each experimental group and each control group are listed as follows:

Each experimental group: each target cell+CTL expressing different chimeric antigen receptors;
Control group 1: target cells with maxium LDH release;
Control group 2: target cells with spontaneous LDH release;
Control group 3: effector cells with spontaneous LDH release.

Detection method: CytoTox 96® Non-Radioactive Cytotoxicity Assay (Promega) is used, which is a colorimetric based assay that can replace 51Cr release assay. CytoTox 96® Assay measures lactate dehydrogenase (LDH) quantitatively. LDH is a stable cytosolic enzyme that is released upon lysis of cells and is released in the same way as radioactive 51Cr is released. The supernatant with released LDH medium can be detected by a 30-minute coupled enzyme reaction in which LDH converts a tetrazolium salt (INT) to a red formazan. The amount of red product produced is proportional to the number of lysed cells. Details can be found in instructions of CytoTox 96 non-radioactive cytotoxicity detection kit.

Cytotoxicity is calculated as:

Cytotoxicity %=[(experiment group−control group 2−control group 3)/(control group 1−control group 2)]×100

Specifically, as shown in Table 4, the CARs of anti-mesothelin single chain antibody (P1A6E, P3F2) of the present invention exhibited significant killing activity on mesothelin-positive pancreatic cancer cells, and the second and third generations of anti-mesothelin CAR T cells were slightly more potent than the antitumor activity of the first generation. There was no significant killing effects in mock group. In addition, all CAR T cells showed no cytotoxic activity on mesothelin-negative PANC-1 pancreatic cancer cells. These results indicate that anti-mesothelin CAR T cells of the invention (including 1$^{st}$, 2$^{nd}$, and 3$^{rd}$ generation of CAR T) can selectively target mesothelin-positive pancreatic cancer cells and kill them effectively. In addition, the first, second and third generation of anti-mesothelin CAR T of the present invention exhibited a effector target ratio gradient dependency, that is, the higher the effector target ratio, the stronger the cytotoxic effects.

TABLE 4

In vitro anti-tumor activity of CAR T cells having single chain antibody fused and expressed

| CYTOTOXICITY (%) | P1A6E-28BBZ Different effector target ratio | | | P1A6E-BBZ Different effector target ratio | | | P1A6E-28Z Different effector target ratio | | | P1A6E-Z Different effector target ratio | | | P1A6E-δZ (mock) Different effector target ratio | | |
|---|---|---|---|---|---|---|---|---|---|---|---|---|---|---|---|
| | 3:1 | 1:1 | 1:3 | 3:1 | 1:1 | 1:3 | 3:1 | 1:1 | 1:3 | 3:1 | 1:1 | 1:3 | 3:1 | 1:1 | 1:3 |
| PANC-1-MSLN | 95.3 | 63.8 | 32.5 | 86.5 | 56.7 | 25.3 | 89.4 | 58.1 | 23.9 | 63 | 33.1 | 13.7 | 2.5 | 1.8 | 3.6 |
| PANC-1 | 3.5 | 4.3 | 2.2 | 1.8 | 2.3 | 3.4 | 2.3 | 3.9 | 2.8 | 1.7 | 2.7 | 3.5 | 2.1 | 2.4 | 2.8 |

TABLE 4-continued

In vitro anti-tumor activity of CAR T cells having single chain antibody fused and expressed

| CYTOTOXICITY (%) | P3F2-28BBZ Different effector target ratio | | | P3F2-BBZ Different effector target ratio | | | P3F2-28Z Different effector target ratio | | | P3F2-Z Different effector target ratio | | | P3F2-δZ (mock) Different effector target ratio | | |
|---|---|---|---|---|---|---|---|---|---|---|---|---|---|---|---|
| | 3:1 | 1:1 | 1:3 | 3:1 | 1:1 | 1:3 | 3:1 | 1:1 | 1:3 | 3:1 | 1:1 | 1:3 | 3:1 | 1:1 | 1:3 |
| PANC-1-MSLN | 85.6 | 62.9 | 30.7 | 89.3 | 60.2 | 31.9 | 92. | 59.3 | 28.7 | 58.4 | 29.9 | 15.7 | 3.1 | 1.5 | 2.8 |
| PANC-1 | 2.8 | 3.1 | 2.5 | 4.8 | 1.8 | 3.6 | 4.1 | 1.7 | 2.8 | 3 | 3.9 | 2.2 | 1.8 | 3.3 | 3.5 |

Example 10. Epitope Analysis of Antibody to Human Mesothelin

Figure 9:
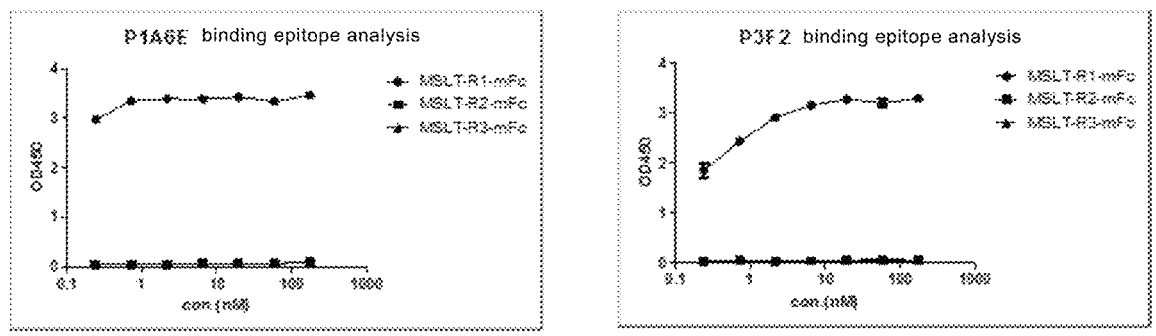
FIG. 9. ELISA showing binding of the antibodies scFv-P1A6E-Fc and scFv-P3F2-Fc to regions R1, R2, R3.
Figure 10:
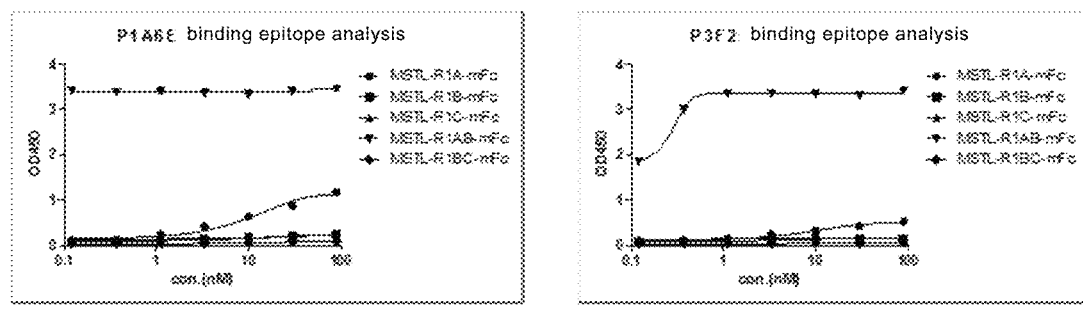
FIG. 10. ELISA showing binding of the antibodies scFv-P1A6E-Fc and scFv-P3F2-Fc to regions R1A, R1B, R1C, R1AB, R1BC.

Human mesothelin gene fragment was amplified by PCR from SEQ ID NO: 1 and ligated into eukaryotic expression vector pCMV-V5-muFc containing mouse Fc fragment by NheI/BamHI double-digestion. HEK-293F cells were transiently transfected according to Example 4 and the culture supernatant of cells was processed and affinity-purified through protein G (from GE) affinity column to finally obtain purified human mesothelin fragment-muFc fusion protein, and the binding of antibodies scFv-P1A6E-Fc and scFv-P3F2-Fc was identified through ELISA. The mature human mesothelin is divided into three regions, region R1 (E296-T390, SEQ ID NO: 66), region R2 (S391-Q486, SEQ ID NO: 67), region R3 (N487-G581, SEQ ID NO: 68) according to Genbank Accession No. NP_001170826.1 (SEQ ID NO: 65). ELISA results showed that both of antibodies scFv-P1A6E-Fc and scFv-P3F2-Fc only bind to region 1 (E296-T390). Region 1 was further divided into 5 small fragments, and fused and expressed with muFc, respectively. Region R1A (296E-337D, SEQ ID NO: 69), Region R1B (328D-369I, SEQ ID NO: 70), Region R1C (360Y-405T, SEQ ID NO: 71), Region R1AB (296E-359L, ID NO: 72), R1BC (328D-405T, SEQ ID NO: 73). The results from ELISA are shown in FIG. 9 and FIG. 10, in which the antibodies scFv-P1A6E-Fc and scFv-P3F2-Fc significantly bound to region R1AB while weakly bound to region R1A and not bound to region R1B. Therefore, the binding sites for the antibodies scFv-P1A6E-Fc and scFv-P3F2-Fc should be located around the sites where R1A and R1B overlap. This region contains 10 amino acids "DAAL-LATQMD", based on which 10 amino acids or 5 amino acids were extended to both ends to form two peptides R1J10: "YKKWELEACVDAALLATQMDRVNAIPFTYE (SEQ ID NO: 74)" and R1J5: "LEACVDAALLATQM-DRVNAI (SEQ ID NO: 75)" and fused and expressed with muFc, respectively. ELISA results showed that antibodies scFv-P1A6E-Fc and scFv-P3F2-Fc did not bind to R1J10 or R1J5. Based on the above results, the epitopes of the antibodies scFv-P1A6E-Fc and scFv-P3F2-Fc should be a conformational epitope located in region R1AB (SEQ ID NO: 72).

All references mentioned in the present invention are incorporated herein by reference, as if each reference was individually incorporated by reference. In addition, it should be understood that after reading the above teachings of the present invention, those skilled in the art can make various modifications or changes to the present invention, and these equivalent forms also fall within the scope of the appended claims of the present application.

The invention claimed is:

1. An antibody that specifically binds to mesothelin, wherein the antibody is at least one selected from the group consisting of:
    (a) an antibody comprising:
        a heavy chain variable region having VH CDR1 comprising the amino acid sequence of SEQ ID NO: 54, VH CDR2 comprising the amino acid sequence of SEQ ID NO: 55, and VH CDR3 comprising the amino acid sequence of SEQ ID NO: 56; and
        a light chain variable region having VL CDR1 comprising the amino acid sequence of SEQ ID NO: 51, VL CDR2 comprising the amino acid sequence of SEQ ID NO: 52, and VL CDR3 comprising the amino acid sequence of SEQ ID NO: 53,
    (b) an antibody comprising:
        a heavy chain variable region having VH CDR1 comprising the amino acid sequence of SEQ ID NO: 60, VH CDR2 comprising the amino acid sequence of SEQ ID NO: 61, and VH CDR3 of the amino acid sequence of SEQ ID NO: 62; and
        a light chain variable region having VL CDR1 comprising the amino acid sequence of SEQ ID NO: 57, VL CDR2 comprising the amino acid sequence of SEQ ID NO: 58 and VL CDR3 of the amino acid of ID NO: 59,
    (c) an antibody comprising:
        a heavy chain variable region comprising the amino acid sequence shown in positions 1 to 123 of SEQ ID NO: 6; and
        a light chain variable region comprising the amino acid sequence shown in positions 139-254 of SEQ ID NO: 6, and
    (d) an antibody comprising:
        a heavy chain variable region comprising the amino acid sequence shown in positions 1 to 124 of SEQ ID NO: 8; and
        a light chain variable region comprising the amino acid sequence shown in positions 140-247 of SEQ ID NO: 8.

2. A nucleic acid encoding the antibody of claim 1.

3. An expression vector comprising the nucleic acid of claim 2.

4. An isolated host cell, comprising the expression vector comprising the nucleic acid encoding the antibody of claim 1 or having the nucleic acid encoding the antibody of claim 1 integrated into the genome.

5. A method, comprising a step of preparing a targeted drug, antibody-drug conjugate, or a polyfunctional antibody that specifically targets tumor cells expressing mesothelin, or preparing a reagent for diagnosing a tumor expressing mesothelin, or preparing a chimeric antigen receptor-modified immune cell by using the antibody of claim 1.

6. A pharmaceutical composition, comprising:
    (a) the antibody of claim 1 or a nucleic acid encoding the antibody of claim 1;
    (b) an immunoconjugate comprising the antibody of claim 1 and a functional molecule linked thereto or a nucleic acid encoding the immunoconjugate,
        wherein the functional molecule includes at least one selected from the group consisting of a molecule that targets a tumor surface marker, a tumor-suppressing molecule, a molecule that targets a surface marker of an immune cell, and a detectable label;
    (c) a chimeric antigen receptor comprising in sequential order: the antibody of claim 1, a transmembrane region, and an intracellular signal region;
    (d) a nucleic acid encoding the chimeric antigen receptor; or
    (e) a genetically modified immune cell, wherein the genetically modified immune cell is transduced with a nucleic acid encoding a chimeric antigen receptor, or an expression vector comprising the nucleic acid, or a virus comprising the expression vector,
        wherein the chimeric antigen receptor comprises in sequential order: the antibody of claim 1, a transmembrane region, and an intracellular signal region, and the genetically modified immune cell expresses the chimeric antigen receptor on a surface thereof.

7. A chimeric antigen receptor, wherein the chimeric antigen receptor comprises
    (a) sequentially linked: the antibody of claim 1; a transmembrane region; and an intracellular signal region, or
    (b) the following sequentially linked antibody, transmembrane region, and intracellular signal region:
        (i) the antibody of claim 1, CD8 and CD3ζ;
        (ii) the antibody of claim 1, CD8, CD137 and CD3ζ;
        (iii) the antibody of claim 1, the transmembrane region of CD28 molecule, the intracellular signal region of CD28 molecule and CD3ζ; or
        (iv) the antibody of claim 1, the transmembrane region of CD28 molecule, the intracellular signal region of CD28 molecule, CD137 and CD3ζ.

8. The chimeric antigen receptor of claim 7, wherein the antibody is a single chain antibody.

9. The chimeric antigen receptor of claim 7, wherein the chimeric antigen receptor has:
    SEQ ID NO: 41 or the amino acid sequence shown in positions 22-353 thereof;
    SEQ ID NO: 42 or the amino acid sequence shown in positions 22-454 thereof;
    SEQ ID NO: 43 or the amino acid sequence shown in positions 22-498 thereof;
    SEQ ID NO: 44 or the amino acid sequence shown in positions 22-501 thereof;
    SEQ ID NO: 45 or the amino acid sequence shown in positions 22-543 thereof;
    SEQ ID NO: 46 or the amino acid sequence shown in positions 22-346 thereof;
    SEQ ID NO: 47 or the amino acid sequence shown in positions 22-447 thereof;
    SEQ ID NO: 48 or the amino acid sequence shown in positions 22-491 thereof;
    SEQ ID NO: 49 or the amino acid sequence shown in positions 22-494 thereof; or
    SEQ ID NO: 50 or the amino acid sequence shown in positions 22-536 thereof.

10. A nucleic acid encoding the chimeric antigen receptor of claim 7.

11. An expression vector comprising the nucleic acid of claim 10.

12. A virus, wherein the virus comprises the expression vector of claim 11.

13. A method for a preparation of genetically modified immune cell targeting a mesothelin-expressing tumor, comprising a step of obtaining a nucleic acid encoding an chimeric antigen receptor, or an expression vector comprising the nucleic acid, or a virus comprising the expression vector,
    wherein the chimeric antigen receptor comprises sequentially linked: the antibody of claim 1, a transmembrane region, and an intracellular signal region.

14. The method of claim 13, wherein the mesothelin-expressing tumor includes at least one selected from the group consisting of pancreatic cancer, ovarian cancer and thymus mesothelioma.

15. The chimeric antigen receptor of claim 7, wherein the intracellular signal region includes at least one selected from the group consisting of intracellular signal region sequences of CD3ζ, FcεRIγ, CD27, CD28, CD137, CD134, MyD88, CD40, and a combination thereof.

16. A genetically modified immune cell, wherein the genetically modified immune cell is transduced with a nucleic acid encoding a chimeric antigen receptor, or an expression vector comprising the nucleic acid, or a virus comprising the expression vector,
   wherein the chimeric antigen receptor comprises sequentially linked: the antibody of claim 1; a transmembrane region; and an intracellular signal region,
   the chimeric antigen receptor is expressed on a surface of the genetically modified immune cell.

17. The genetically modified immune cell of claim 16, wherein the genetically modified immune cell further contains an encoding sequence of an exogenous cytokine;
   the genetically modified immune cell further expresses another chimeric antigen receptor that does not contain CD3ζ but contains the intracellular signaling domain of CD28, the intracellular signaling domain of CD137, or a combination thereof;
   the genetically modified immune cell further expresses a chemokine receptor;
   the genetically modified immune cell further expresses siRNA capable of reducing expression of PD-1 or a protein which blocks PD-L1;
   the genetically modified immune cell further expresses a safety switch; or
   the genetically modified illumine cell are genetically modified T lymphocyte, NK cell, or NKT cell.

18. The genetically modified immune cell of claim 17, wherein the exogenous cytokine includes IL-12, IL-15, or IL-21, or
   the chemokine receptor includes CCR2, or
   the safety switch includes iCaspase-9, truncated EGFR, or RQR8.

19. A multi-functional immunoconjugate, wherein the multi-functional immunoconjugate comprises:
   the antibody of claim 1; and
   a functional molecule linked thereto,
   wherein the functional molecule includes at least one selected from the group consisting of a molecule that targets a tumor surface marker, a tumor-suppressing molecule, a molecule that targets a surface marker of an immune cell, and a detectable label.

20. A nucleic acid encoding the multi-functional immunoconjugate of claim 19.

21. A method, comprising a step of preparing an antineoplastic agent or an agent for diagnosis of tumors that express mesothelin, or a
   chimeric antigen receptor modified immune cell by using the multi-functional immunoconjugate of claim 19.

22. The multi-functional immunoconjugate of claim 19, wherein the molecule that targets the tumor surface marker is an antibody or ligand that binds to a tumor surface marker; or the tumor-suppressing molecule is an anti-tumor cytokine or an anti-tumor toxin; or
   the detectable label includes a fluorescent label or a chromogenic label.

23. The multi-functional immunoconjugate of claim 22, wherein the anti-tumor cytokine includes IL-12, IL-15, IFN-beta, ear TNF-alpha, and
   the antibody that binds to a tumor surface marker refers to an antibody that recognizes an antigen other than mesothelin, and the antigen other than mesotheline includes EGFR, EGFRvIII, mesothelin, HER2, EphA2, Her3, EpCAM, MUC1, MUC16, CEA, Claudin 18.2, folate receptor, Claudin 6, CD3, WT1, NY-ESO-1, MAGE 3, ASGPR1, or CDH16.

24. The method of claim 21, wherein the chimeric antigen receptor modified immune cell is modified from an immune cell, and the immune cell includes T lymphocyte, NK cell, or NKT lymphocyte.

25. A multi-functional immunoconjugate comprising:
   the antibody of claim 1; and
   a functional molecule linked thereto,
   wherein the functional molecule includes at least one selected from the group consisting of a molecule that targets a tumor surface marker, a tumor-suppressing molecule, a molecule that targets a surface marker of an immune cell, and a detectable label;
   the molecule that targets the surface marker of the immune cell is an antibody that binds to a T cell surface marker and forms a T-cell engaging bifunctional antibody with the antibody of claim 1.

26. The multi-functional immunoconjugate of claim 25, wherein the molecule that targets the tumor surface marker is an antibody or ligand that binds to a tumor surface marker; or
   the tumor-suppressing molecule is an anti-tumor cytokine or an anti-tumor toxin; or
   the detectable label includes a fluorescent label or a chromogenic label.

27. The multi-functional immunoconjugate of claim 26, wherein the anti-tumor cytokine includes IL-12, IL-15, IFN-beta, or TNT-alpha.

28. The multi-functional immunoconjugate of claim 26, wherein the antibody that binds to a tumor surface marker refers to an antibody that recognizes an antigen other than mesothelin, and the antigen other than mesothelin includes EGFR EGFRvIII, mesothelin, HE2, EphA2, Her3, EpCAM, MUC1, MUC16, CEA, Claudin 18.2, folate receptor, Claudin 6, CD3, WT1, NY-ESO-1, MAGE 3, ASGPR1, or CDH16.

29. The multi-functional immunoconjugate of claim 25, wherein the antibody that binds to a T cell surface marker is an anti-CD3 antibody.

30. The multi-functional immunoconjugate of claim 25, wherein the multi-functional immunoconjugate is a fusion polypeptide and further comprises a linker peptide between the antibody of claim 1 and the functional molecule linked thereto.

* * * * *